US 6,613,769 B1

(12) United States Patent
Bode et al.

(10) Patent No.: US 6,613,769 B1
(45) Date of Patent: Sep. 2, 2003

(54) TRYPTASE INHIBITORS

(75) Inventors: Wolfram Bode, Gauting (DE); Luis Moroder, Martinsried (DE); Pedro Jose Barbosa Pereira, Krailling (DE); Andreas Bergner, Neuried (DE); Robert Huber, Germering (DE); Christian Sommerhoff, München (DE); Norbert Schaschke, München (DE); Thomas Bär, Constance (DE); Thomas Martin, Constance (DE); Josef Stadlwieser, Constance (DE); Wolf-Rüdiger Ulrich, Constance (DE); Andreas Dominik, Allensbach (DE); Ulrich Thibaut, Constance (DE); Daniela Bundschuh, Constance (DE); Rolf Beume, Constance (DE); Karl-Josef Goebel, Radolfzell (DE)

(73) Assignees: Max-Planck-Gesellschaft zur Föderung der Wissenschaften. e.V., München (DE); Altana Pharma AG, Constance (DE)

( * ) Notice: Subject to any disclaimer, the term of this patent is extended or adjusted under 35 U.S.C. 154(b) by 0 days.

(21) Appl. No.: 09/601,318
(22) PCT Filed: Feb. 4, 1999
(86) PCT No.: PCT/EP99/00727
§ 371 (c)(1), (2), (4) Date: Jan. 22, 2001
(87) PCT Pub. No.: WO99/40073
PCT Pub. Date: Aug. 12, 1999

(30) Foreign Application Priority Data

Feb. 6, 1998 (DE) .......................................... 198 04 761
Nov. 6, 1998 (DE) .......................................... 198 51 300

(51) Int. Cl.⁷ .................... A61K 31/495; A61K 31/445; C07D 241/04; C07D 401/00; C07D 211/00
(52) U.S. Cl. ........................... 514/252.12; 514/255.01; 514/255.05; 514/316; 514/318; 514/330; 514/331; 514/332; 544/358; 544/359; 544/383; 544/386; 544/399; 544/402; 546/186; 546/189; 546/190; 546/191; 546/246; 546/248; 435/217
(58) Field of Search ................................ 544/358, 359, 544/384, 398, 402, 383, 386, 399; 514/252.12, 255.01, 255.05, 318, 330, 331, 332; 435/212; 546/186, 189, 190, 191, 246, 248

(56) References Cited

U.S. PATENT DOCUMENTS 6,489,327 B1 * 12/2002 Bar et al. .............. 514/253.11

FOREIGN PATENT DOCUMENTS

| EP | 0 893 437 | 1/1999 |
| WO | 9532945 | * 12/1995 |
| WO | 96 09297 | 3/1996 |
| WO | 97 37969 | 10/1997 |
| WO | 9804537 | * 2/1998 |

OTHER PUBLICATIONS

CAS Abstr. 113:128421–1990:528421: Dietze et al; "A new highly sensitive . . . assay for hunam tryptase . . . ".*
PUbMed Abstr. 10092484:Chan et al:"Expression & Characterization of . . . Tryptase";Protein Expr Purif 15/3, 251–7(1999).*

* cited by examiner

Primary Examiner—Mukund J. Shah
Assistant Examiner—Sudhaker B. Patel
(74) Attorney, Agent, or Firm—Rothwell, Figg, Ernst & Manbeck

(57) ABSTRACT

The invention relates to bifunctional tryptase inhibitors of formula (I)

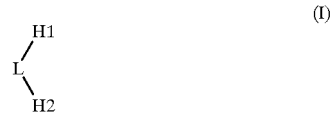

wherein H1 and H2 comprise a Q group and L is a linker of formula

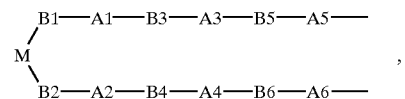

and the conformation of the H1, H2 and L groups is such that the groups are separated by a distance of from 20 to 45 Å. Pharmaceutical compositions and crystal forms of the compounds are described in addition to methods for producing and identifying such compounds, as well as the use of such compounds in methods of treating allergic and inflammatory diseases.

4 Claims, 22 Drawing Sheets

Fig.20

```
HEADER     HUMAN BETA TRYPTASE
COMPND     HUMAN LUNG MASTCELL BETA TRYPTASE
AUTHOR     W.BODE, A.BERGNER, C.SOMMERHOFF, P.J. PEREIRA
SEQRES     1   244   ILE VAL GLY GLY GLN GLU ALA PRO ARG SER LYS TRP PRO
SEQRES     2   244   TRP GLN VAL SER LEU ARG VAL HIS GLY PRO TYR TRP MET
SEQRES     3   244   HIS PHE CYS GLY GLY SER LEU ILE HIS PRO GLN TRP VAL
SEQRES     4   244   LEU THR ALA ALA HIS CYS VAL GLY PRO ASP VAL LYS ASP
SEQRES     5   244   LEU ALA ALA LEU ARG VAL GLN LEU ARG GLU GLN HIS LEU
SEQRES     6   244   TYR TYR GLN ASP GLN LEU LEU PRO VAL SER ARG ILE ILE
SEQRES     7   244   VAL HIS PRO GLN PHE TYR THR ALA GLN ILE GLY ALA ASP
SEQRES     8   244   ILE ALA LEU LEU GLU LEU GLU GLU PRO VAL LYS VAL SER
SEQRES     9   244   SER HIS VAL HIS THR VAL THR LEU PRO PRO ALA SER GLU
SEQRES    10   244   THR PHE PRO PRO GLY MET PRO CYS TRP VAL THR GLY TRP
SEQRES    11   244   GLY ASP VAL ASP ASN ASP GLU ARG LEU PRO PRO PRO PHE
SEQRES    12   244   PRO LEU LYS GLN VAL LYS VAL PRO ILE MET GLU ASN HIS
SEQRES    13   244   ILE CYS ASP ALA LYS TYR HIS LEU GLY ALA TYR THR GLY
SEQRES    14   244   ASP ASP VAL ARG ILE VAL ARG ASP ASP MET LEU CYS ALA
SEQRES    15   244   GLf ASN THR ARG ARG ASP SER CYS GLN GLY ASP SER GLY
SEQRES    16   244   GLY PRO LEU VAL CYS LYS VAL ASN GLY THR TRP LEU GLN
SEQRES    17   244   ALA GLY VAL VAL SER TRP GLY GLU GLY CYS ALA GLN PRO
SEQRES    18   244   ASN ARG PRO GLY ILE TYR THR ARG VAL THR TYR TYR LEU
SEQRES    19   244   ASP TRP ILE HIS HIS TYR VAL PRO LYS LYS
SEQRES     1   244   ILE VAL GLY GLY GLN GLU ALA PRO ARG SER LYS TRP PRO
SEQRES     2   244   TRP GLN VAL SER LEU ARG VAL HIS GLY PRO TYR TRP MET
SEQRES     3   244   HIS PHE CYS GLY GLY SER LEU ILE HIS PRO GLN TRP VAL
SEQRES     4   244   LEU THR ALA ALA HIS CYS VAL GLY PRO ASP VAL LYS ASP
SEQRES     5   244   LEU ALA ALA LEU ARG VAL GLN LEU ARG GLU GLN HIS LEU
SEQRES     6   244   TYR TYR GLN ASP GLN LEU LEU PRO VAL SER ARG ILE ILE
SEQRES     7   244   VAL HIS PRO GLN PHE TYR THR ALA GLN ILE GLY ALA ASP
SEQRES     8   244   ILE ALA LEU LEU GLU LEU GLU GLU PRO VAL LYS VAL SER
SEQRES     9   244   SER HIS VAL HIS THR VAL THR LEU PRO PRO ALA SER GLU
SEQRES    10   244   THR PHE PRO PRO GLY MET PRO CYS TRP VAL THR GLY TRP
SEQRES    11   244   GLY ASP VAL ASP ASN ASP GLU ARG LSE PRO PRO PRO PHE
SEQRES    12   244   PRO LEU LYS GLN VAL LYS VAL PRO ILE MET GLU ASN HIS
SEQRES    13   244   ILE CYS ASP ALA LYS TYR HIS LEU GLY ALA TYR THR GLY
SEQRES    14   244   ASP ASP VAL ARG ILE VAL ARG ASP ASP MET LEU CYS ALA
SEQRES    15   244   GLY ASN THR ARG ARG ASP SER CYS GLN GLY ASP SER GLY
SEQRES    16   244   GLY PRO LEU VAL CYS LYS VAL ASN GLY THR TRP LEU GLN
SEQRES    17   244   ALA GLY VAL VAL SER TRP GLY GLU GLY CYS ALA GLN PRO
SEQRES    18   244   ASN ARG PRO GLY ILE TYR THR ARG VAL THR TYR TYR LEU
SEQRES    19   244   ASP TRP ILE HIS HIS TYR VAL PRO LYS LYS
SEQRES     1   244   ILE VAL GLY GLY GLN GLU ALA PRO ARG SER LYS TRP PRO
SEQRES     2   244   TRP GLN VAL SER LEU ARG VAL HIS GLY PRO TYR TRP MET
SEQRES     3   244   HIS PHE CYS GLY GLY SER LEU ILE HIS PRO GLN TRP VAL
SEQRES     4   244   LEU THR ALA ALA HIS CYS VAL GLY PRO ASP VAL LYS ASP
SEQRES     5   244   LEU ALA ALA LEU ARG VAL GLN LEU ARG GLU GLN HIS LEU
SEQRES     6   244   TYR TYR GLN ASP GLN LEU LEU PRO VAL SER ARG ILE ILE
SEQRES     7   244   VAL HIS PRO GLN PHE TYR THR ALA GLN ILE GLY ALA ASP
SEQRES     8   244   ILE ALA LEU LEU GLU LEU GLU GLU PRO VAL LYS VAL SER
SEQRES     9   244   SER HIS VAL HIS THR VAL THR LEU PRO PRO ALA SER GLU
SEQRES    10   244   THR PHE PRO PRO GLY MET PRO CYS TRP VAL THR GLY TRP
SEQRES    11   244   GLY ASP VAL ASP ASN ASP GLU ARG LEU PRO PRO PRO PHE
SEQRES    12   244   PRO LEU LYS GLN VAL LYS VAL PRO ILE MET GLU ASN HIS
SEQRES    13   244   ILE CYS ASP ALA LYS TYR HIS LEU GLY ALA TYR THR GLY
SEQRES    14   244   ASP ASP VAL ARG ILE VAL ARG ASP ASP MET LEU CYS ALA
SEQRES    15   244   GLY ASN THR ARG ARG ASP SER CYS GLN GLY ASP SER GLY
SEQRES    16   244   GLY PRO LEU VAL CYS LYS VAL ASN GLY THR TRP LEU GLN
SEQRES    17   244   ALA GLY VAL VAL SER TRP GLY GLU GLY CYS ALA GLN PRO
SEQRES    18   244   ASN ARG PRO GLY ILE TYR THR ARG VAL THR TYR TYR LEU
SEQRES    19   244   ASP TRP ILE HIS HIS TYR VAL PRO LYS LYS
SEQRES     1   244   ILE VAL GLY GLY GLN GLU ALA PRO ARG SER LYS TRP PRO
SEQRES     2   244   TRP GLN VAL SER LEU ARG VAL HIS GLY PRO TYR TRP MET
SEQRES     3   244   HIS PHE CYS GLY GLY SER LEU ILE HIS PRO GLN TRP VAL
```

TRYPTASE INHIBITORS

The invention relates to bifunctional inhibitors of human tryptase, to human tryptase in crystallized form, to a process for preparing human tryptase in crystallized form, to pharmaceutical compositions which comprise a bifunctional inhibitor of human tryptase, and to a process for developing and identifying tryptase inhibitors.

Human tryptase is a serine proteinase which is the predominant protein present in human mast cells. The term tryptase covers four closely related enzymes (α, I, II/β, III; possessing 90 to 98% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815). With the exception of α-tryptase (Schwartz et al., J. Clin. Invest. 96 (1995) 2702–2710; Sakai et al., J. Clin. Invest. 97 (1996) 988–995), the enzymes are activated intracellularly and stored in catalytically active form in secretory granules.

As compared with other known serine proteinases, such as trypsin or chymotrypsin, tryptase exhibits some exceptional properties (Schwartz et al., Methods Enzymol. 244, (1994), 88–100; G. H. Caughey, "Mast cell proteases in immunology and biology." Marcel Dekker, Inc., New York, 1995). Tryptase obtained from human tissue has a noncovalently linked tetrameric structure which has to be stabilized by heparin or other proteoglycans in order to be proteolytically active. Furthermore, the serum is not so far known to contain any factor which inhibits tryptase. Attempts to find an endogenous inhibitor of tryptase have so far been unsuccessful. With the exception of the atypical inhibitor LDTI (leech-derived tryptase inhibitor) (Sommerhoff et al., Biol. Chem. Hoppe-Seyler 375 (1994) 685–694), tryptase is not inhibited by naturally occurring proteinase inhibitors either.

In addition, tryptase exhibits an unusual, very narrow substrate specificity, with a number of peptide substrates (Tam et al., Am. J. Respir. Cell Mol. Biol. 3 (1990) 27–32), but only a few selected proteins, being cleaved in vitro. For example, fibrinogen, fibronectin and high molecular weight kininogen are inactivated (Schwartz et al., J. Immunol., 135(4) (1985), 2762–2767; Lohi et al., J. Cell. Biochem. 50, (1992), 337–349; Little et al., Biochem. J. 307 (1995) 341–346), and the zymogens of stromelysin (proMMP-3) and the plasminogen activator of the urokinase type (pro-uPA) are activated (Gruger et al., J. Clin. Invest. 84 (1989), 1657–1662; Lees et al., Eur. J. Biochem. 223 (1994), 171–177; Stack et al., J. Biol. Chem. 269 (1994), 9416–9419). Furthermore, it has been discovered that tryptase exhibits mitogenic effects (Ruoss et al., J. Clin. Invest. 88 (1991), 493–499; Hartmann et al., Am. J. Physiol. 262 (1992), L528–L534; Brown et al., Am. J. Respir. Cell Mol. Biol. 13 (1995), 227–236).

Tryptase is released, together with other inflammation mediators, such as histamine and proteoglycans, when human mast cells are activated. It is therefore assumed that tryptase is involved in a number of diseases, in particular in allergic and inflammatory diseases, on the one hand because of the importance of mast cells in such diseases and, on the other hand, since an elevated content of tryptase has been observed in several such diseases. Thus, tryptase is thought to be linked with the following diseases, inter alia: acute and chronic (in particular inflammatory and allergenically induced) respiratory diseases of varying origin (e.g. bronchitis, allergic bronchitis, bronchial asthma and COPD); interstitial pulmonary diseases; diseases which are based on allergic reactions of the upper airways (pharynx and nose) and of the adjacent regions (e.g. paranasal sinuses and conjuctivas), such as allergic conjunctivitis and allergic rhinitis; diseases which belong to the complex of arthritic diseases (e.g. rheumatoid arthritis); autoimmune diseases such as multiple sclerosis; and, in addition, periodontitis, anaphylaxis, interstitital cystitis, dermatitis, psoriasis, dermatosclerosis/systemic sclerosis, inflammatory intestinal diseases (Crohn's disease and inflammatory bowel disease) and others. Tryptase appears, in particular, to be directly associated with the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, chapter 3.3.1-3.3.23).

However, in order to be able to investigate the precise function of tryptase, in particular in allergic and inflammatory diseases, it is necessary to develop selective tryptase inhibitors. To date, tryptase inhibitors have been designed and synthesized on the basis of the activity and specificity of tryptase, which are similar to those of trypsin, starting, for the most part, from a benzamidine group as substrate residue. Inhibitors of varying quality were found by the method of trial and error, with benzamidine and similar structures, in particular, being derivatized with groups which were to a greater or lesser degree rigid and hydrophobic. An example of this is 4-amidinophenylpyruvic acid (APPA; Stürzebecher et al., Biol. Chem. Hoppe-Seyler 373 (1992), $_{1025-1030}$). However, such benzamidine-based inhibitors are not selective for tryptase, but also inhibit other physiologically important enzymes such as thrombin, factor Xa and urokinase. They cannot, therefore, be used for investigating the function of tryptase selectively.

A peptide inhibitor of tryptase, namely N-(1-hydroxy-2-naphthoyl)-L-arginyl-L-prolineamide, has also been described in the state of the art (R. Tanaka, Protease Inhibitors, IBC Series 1997, chapter 3.3; Clark et al., Drugs of the future 21(8) (1996), 811–816; WO 94/20527). However, this inhibitor is not selective for tryptase either, but also inhibits other proteinases such as trypsin and thrombin, so that it is not possible to establish unambiguously whether observed effects are being achieved due to a specific inhibition of tryptase or, rather, due to other occurrences.

Another inhibitor of tryptase which is described in the state of the art is LDTI, which is an inhibitor of the Kazal type and was isolated from leeches (LDTI, leech-derived tryptase inhibitor) (WO95/03333; Stubbs et al., J. Biol. Chem. 272 (32) (1979), 19931–19937; WO97/22626). LDTI is a proteinaceous inhibitor whose structure was determined with the aid of NMR data and using LDTI and trypsin crystals. In this connection, it was ascertained that the basic aminoterminus of LDTI probably makes an electrostatic contribution to the interaction with tryptase. While LDTI is an inhibitor which has a high affinity for tryptase ($K_i$ of 1.4 nM), it also inhibits trypsin and chymotrypsin in the nanomolar range.

SLPI (secretory leukocyte protease inhibitor) has been suggested as being another inhibitor of tryptase (WO96/08275 A1). This inhibitor is also proteinaceous. Finally, WO95/32945, WO96/09297 and WO98/04537 describe low molecular weight compounds which are tryptase inhibitors. At their ends, these compounds predominantly exhibit amino, guanidino or amidino groups. The activity of these compounds is likewise determined by trial and error.

One object of the present invention was therefore to provide highly specific inhibitors of human tryptase, the activity of which inhibitors can be reliably predicted using structural parameters. According to the invention, this object is achieved by means of a bifunctional inhibitor of human tryptase wherein the inhibitor comprises two head groups, H1 and H2, which are connected by a linker L, with H1 and H2 being identical or different and in each case comprising a Q group which can enter into interactions with a carboxylate group, with the linker L being able to assume such a conformation that the Q groups of the two head groups are present at a distance of from 20 to 45 Å, and with the sizes of the head groups and of the linker permitting the inhibitor to penetrate into a cavity having the dimensions 52 Å×32 Å×40 Å. In this present document, embodiments of the Q group are also designated group X1, X2 and group Y1, Y2, respectively, and are defined in more detail below.

Success has surprisingly been achieved in obtaining crystals of human β-tryptase from mast cells and carrying out an X-ray crystal structure analysis. This has made it possible to determine precisely the spatial, three-dimensional geometry of the tryptase tetramer resulting in important insights being obtained with regard to the development of tryptase inhibitors.

It has been found that, in the crystals, flat, square, frame-like tetramers having the dimensions 82×80×40 Å are stacked on top of each other along a $4_1$ screw axis. Along its four edges, each tetramer is in close contact with symmetry-related neighbors such that extended layers are formed. Within a tetramer, a tryptase unit is present at each corner of the tetramer, i.e. each of the four, chemically identical monomers occupies a corner of the flat frame having a virtually square shape. The four tryptase units of the tetramer form the boundary of a central, oval channel, or a central pore, having the approximate dimensions 52×32×40 (depth) Å. The two entrances to this pore are partially obstructed by a peptide loop protruding from each of the monomers (147 loop). This results in the pore widening internally into a larger cavity.

The flat, frame-shaped structure of the tryptase tetramer which has been found is surprising and differs fundamentally from the previously published, diagrammatic tryptase models, in which a compact, "quasi-tetrahedral" structure has been specified (Johnson et al., Protein Sci. 1, (1992), 370–377; Matsumoto et al., J. Biol. Chem. 270 (1995), 19524–19531; G. H. Caughey, Am. J. Respir. Cell Mol. Biol. 16 (1997), 621–628).

All the tryptase units of the tetramer are virtually identical in their structure and only differ from each other in their relative orientation and in the contacts with their neighbors. The tetramer therefore possesses a quasi-2 2 2-symmetry, with the four (quasi) equivalent units being arranged in a rectangular, flat ring. Of the four monomers, which are designated A, B, C and D clockwise below (cf. FIG. 1), A is identical to C and B is identical to D. The tryptase monomer A touches its neighbors B and D by way of two different areas of contact, of about 500 and 1100 Å$^2$, respectively. The tryptase units A and D (exactly like B and C), which can be interconverted by way of dyadic axes of rotation, are linked to each other by way of a long peripheral bridge, with polar interactions as well as hydrophobic interactions contributing to the linkage. At the peripheral surface of the A–D (and of the corresponding B–C) homodimer, positive charges are counterbalanced by negative charges, resulting in a relatively weak electrostatic potential.

In contrast to this, the dyadic symmetry between monomers A and B (just as between monomers C and D) is disrupted locally and the two monomers are in touch with each other over a comparatively small, and therefore relatively unstable, hydrophobic area of contact. This central, circular area of contact consists exclusively of hydrophobic interactions. Under physiological conditions, the A–B (as well as the C–D) homodimer is held together by heparin chains which attach to the positively charged peripheral areas. Thus, the A–B homodimer (as well as the equivalent C–D homodimer) carries a number of positively charged residues on its peripheral surface, which residues form a positive electrostatic potential.

Each tryptase monomer consists of 246 amino acids (cf. FIG. 4) and, depending on the degree of glycosylation, has a molecular weight of from 31 to 34 kDa. In a similar way to that of all other trypsin-like serine proteinases, the core structure of each monomer consists of two 6-stranded β-barrels (cf. FIG. 3). These β-barrels are held together by three trans-domain segments and additionally contain, at their surface, two helices and a number of peptide loops. The catalytic residues Ser195, His57 and Asp102 (the residues are designated in accordance with the so-called chymotrypsinogen numbering, which is defined on the basis of the topological similarity to bovine chymotrypsinogen A, cf. FIG. 4) are arranged in the contact line between the two barrels, while the active center cleft runs perpendicularly to the two barrels.

The tryptase core, consisting of about 165 residues, is topologically similar to the core regions of the reference proteinases trypsin and chymotrypsin. However, the additional residues of the tryptase (15 and 22, respectively) possess marked conformational differences, in particular different loop structures. Thus, drastic differences are evident with regard to length and geometry in six superficial peptide loops which surround the active center (the 70 to 80 loop, the 147 loop with the attached 152 spur, the 37 loop, the 60 loop, the 170 loop and the 97 loop). In this context, monomers A and B come to touch each other by way of the first three loops mentioned, while monomers A and D are in contact with each other by way of the last three loops mentioned. The 60 loop, which contains five inserted residues, runs abruptly away from the cleft in the northerly direction (the relative directions given relate to the orientation shown in FIG. 2), where it bends at cisPro 60 A, in order to slowly approach the general main-chain course of other serine proteinases. Position 69, which is strictly reserved for a Gly in all the other homologous proteinases, has an Arg residue in tryptase. The following 70 to 80 loop, which in the calcium-binding serine proteinases winds around a stabilizing calcium ion (Bode et al., J. Mol. Biol. 98 (1975) 693–717), is more compact in tryptase and three amino acids shorter. It is probably not used for calcium binding, despite topologically similar ligand groups (Glu70, Asp80 and carbonyls 72 and 75). The 97 loop, which forms the northern edge of the cleft, comprises the same number of residues which have, however, a different arrangement: Ala97 takes the position normally occupied by residue 99. In addition, the loop exhibits an unusual helical turn leading to Asp102. The 147 loop (designated "autolytic loop" in pancreatic proteinases), which forms the southern wall of the active cleft together with Gln192, is one residue shorter up to Leu151. The following unusual Pro152-Pro152A-cisPro152B-Phe153-Pro154 sequence, which comprises two insertion residues, forms a hydrophobic 152 "spur". The largest insertion, consisting of nine residues, occurs in the 173 loop, which follows the unusually long 3-turn "intermediate helix" (helix α1, cf. FIG. 4). The ten residues from His173 to Val173I form an extended open 173 bend, which is arranged about the imidazole side chain of His173.

In the tryptase monomer, the structure of the active center and its environment is very similar to that in trypsin. The so-called S1 specificity pocket (in that which follows, the peptide positions N-terminally and C-terminally, respectively, of the peptide bond, of a bound peptide substrate, which is to be cleaved are designated P1, P2, etc. and P1', P2', etc., respectively, and the corresponding binding sites on the enzyme are designated S1, S2, etc., and S1', S2', etc., respectively), which opens to the left (with regard to the so-called standard orientation, defined by a horizontally running active center cleft facing the observer, in which cleft bound peptide substrates would run from left to right; cf. FIG. 3) of the reactive Ser195, is practically identical to that in trypsin with regard to the conformation of the surrounding main chains, with its "entrance frame" Val213-Ser214-Trp215-Gly216-Glu217-Gly219-Cys220 (with Glu217 representing an exception), its "inner wall" Gly226-Ile227 (instead of Val)-Tyr228, its "floor" Asp189-Ser190-Cys191-Gln192-Gly193-Asp194-Ser195 and the concluding disulfide bridge Cys191 to Cys220, and is suitable for receiving P1-lysine side chains or arginine side chains.

The amidinophenyl group of amidinophenylpyruvic acid (APPA) protrudes into this pocket in the same way as in APPA-trypsin (Walter and Bode et al., Hoppe-Seylers Z. Physiol. Chem. 364 (1983), 949–959) and in APPA-thrombin (Chen et al., Arch. Biochem. Biophys. 322 (1995), 198–203), with the amidino group facing the carboxylate group of Asp189 (on the floor of the pocket) and forming additional hydrogen bonds with the carbonyl group of Gly219 and the Oγ of Ser190, and the phenyl group being enclosed by the peptide planes 215 to 216 and 190 to 192. The APPA pyruvate group projects out of the pocket, with the carbonyl group attaching to the Ser195 Oγ with the formation of a tetrahedral transition state (hemiketal). The Asp143 side chain and (slightly displaced to the left) the Asp147 side chain project, somewhat separated by the Gln192 side chain, out of the surface of the molecule below the S1 pocket (standard orientation). The resulting negative charge is a possible second anchorage point for the basic synthetic tryptase inhibitors such as bis-benzamidines (Stürzebecher et al., Biol. Chem. Hoppe-Seyler 373 (1992) 1025–1030; Caughey et al., J. Pharmacol. Exp. Ther. 264 (1993), 676–682; Stubbs et al., J. Biol. Chem. 272 (1997), 19931–19937).

The S2 binding region, which is bounded toward the top by the flat side of the His57 imidazole group and the Ala97 side chain, and also (further outward) by the Pro60A, is somewhat larger than in trypsin. On the other hand, the size of the S3/S4 region, which rests on the indole group of the Trp215 and the Glu217 side chain, is greatly restricted toward the top by the Gln98 side chain of the same monomer and the Tyr95 phenol group of the neighboring monomer (D). The side chains of the Pro60A and the Asp60B of the neighboring monomer (D) form the left border of the S6 region. The S1' and S2' regions are very similar to those in trypsin. On the other hand, the S3' region is restricted to a greater extent on the right hand side by the protruding Pro37A, and a peptide chain which is bonded with an extended conformation would push against residues of the neighboring monomer (B) shortly after the P5' residue. The subregions S2 to S6 of monomers and D (and also of monomers B and C) lie in a large common hollow, which is overarched by a continuous "canopy", which is formed from the projecting 95, 170 and 60 peptide loops of the two monomers, and in which the S1 to S4 binding regions of monomers A and D face each other. This geometry, i.e. the spatial proximity of the active centers of the A and D subunits (and also of the B and C subunits) in the tetramer makes it possible to develop bifunctional inhibitors which possess two functional inhibitor groups which are spatially separated in a corresponding manner and which bind to two different, in particular neighboring, active sites in different monomer subunits of the tetramer. The connecting line between the two Ser195 Oγ atoms, which are at a distance of approximately 23 Å from each other (and also between the respective S1, S2, S3, S4 or S1' subregions), runs through the free space of the strongly negatively charged cavity. Correspondingly constructed bifunctional inhibitors can therefore connect the two catalytic centers with each other through this free space.

The insights gained from the X-ray structural analysis are very useful for developing specific tryptase inhibitors whose geometry is optimized.

The inhibitors according to the invention are bifunctional inhibitors, i.e. inhibitors which possess two functional groups which are capable of binding. These groups are constructed in such a way that they are able to bind specifically to tryptase active sites. The two functional groups of the inhibitor preferably bind to active sites in different monomer subunits of the tryptase tetramer.

The inhibitors according to the invention are suitable for inhibiting human tryptase. Human tryptase is understood, in particular, as being the human β-tryptase enzyme having the EC No. 3.4.21.59.

The bifunctional inhibitors according to the invention are characterized by the fact that they comprise two head groups, which are termed H1 and H2 in this present document and which are connected by a linker L. The head groups H1 and H2 can be identical or different and in each case comprise a Q-group which is able to enter into interactions with a carboxylate group. It is fundamental to the invention that the linker L is able to assume a conformation which is such that the Q groups of the two head groups are present at a distance of from 20 to 45 Å. This spatial requirement ensues from the spatial structure of the active centers of the tryptase tetramer, as ascertained by the X-ray structure of the tryptase.

Furthermore, the sizes of the head groups and of the linker of the bifunctional inhibitors must enable the inhibitors to penetrate into a cavity having the dimensions 52 Å×32 Å×40 Å (depth). The narrow opening of the central channel, which, as explained above, is additionally constricted by peptide loops, prevents bulky inhibitors from penetrating in. It is for this reason that proteinaceous inhibitors which are known for other serine proteinases are not effective in the case of tryptase. To be effective, inhibitors of tryptase must therefore possess, as a fundamental requirement, a spatial structure which allows the inhibitors to penetrate into the central cavity which is enclosed by the four tryptase subunits. It was ascertained, surprisingly, that the spatial restriction with regard to the pore which is formed by the 4 subunits and further constricted by peptide loops, as well as the immediate environment of the specificity pocket, are of importance for the structure of the inhibitor.

The inhibitors according to the invention have the formula I

The head groups, H1 and H2, of the inhibitors according to the invention preferably comprise Q groups which are able to enter into interactions with the carboxylate groups of tryptase Asp189. Asp189 is the amino acid aspartic acid in position 189 of the individual amino acid sequences of the monomeric subunits of the tryptase when using a method of counting which is analogous to the method of counting known for the amino acid sequence of chymotrypsin (cf. FIG. 4). The distance between the carboxyl groups of the Asp189 residues is measured, in the tryptase X-ray structure, as being the shortest distance between the respective centroids by way of the two terminal oxygen atoms of the carboxylate groups. The distances between the carboxylate groups of the Asp189 residues in the respective subunits are, between A and B 45 Å±1 Å, between A and C 45 Å±1 Å, between A and D 33 Å±1 Å, between B and C 33 Å±1 Å, between B and D 45 Å±1 Å and between C and D 45 Å±1 Å.

The Asp189 residues are constituents of the specificity pockets of the active centers of the respective subunits. A tryptase inhibitor which is preferred in accordance with the invention consequently comprises two identical or different head groups H1 and H2, each of which comprises a Q group which is able to enter into interactions with a carboxylate group, with the head groups being connected by a linker L, with the linker L being able to assume a conformation which enables the two Q groups of the head groups H1 and H2 to enter into an interaction with the carboxylate groups of the Asp189 residues in the specificity pockets of two different subunits of the tryptase, with the dimensions of the linker being such that it fits into the central cavity which is enclosed by the four subunits. Preferably, the linker L is able to assume a conformation which is such that the Q groups of the two head groups are present at a distance of from 20 to 45 Å, so that it is possible for the Q groups to interact with the carboxylate groups of the Asp189 residues of the A and D subunits, or of the B and C subunits, respectively.

There is no restriction on the nature of the interaction between the Q groups and the carboxylate groups. The bifunctionality of the inhibitor results in its binding affinity, and consequently its specificity in relation to tryptase, being high even when these interactions are slight. Preference is given to using Q groups which are able to enter into ionic interactions and/or hydrogen bond interactions with carboxylate groups, in particular with the carboxylate groups of the Asp189 residues in the A and D subunits or in the B and C subunits, respectively, of the tryptase. In this context, the interactions can also be mediated by way of one or more water molecules, with the water molecule(s) coming to lie between the head group and the carboxylate group, in particular the carboxylate group of the Asp189 residue. In order to develop the interactions effectively, where appropriate while including one or more water molecules, the Q groups are preferably located at a distance of from about 2.5 to 5 Å from one or both of the carboxylate oxygen atoms, in particular the carboxylate oxygen atoms of Asp189 in the S1 pocket.

The linker L preferably comprises aromatic, heterocyclic, alicyclic or aliphatic groups. In principle, the total size of the linker or of the bifunctional inhibitor is not restricted. However, what is essential for the function as a tryptase inhibitor is that the sizes of the head groups and of the linker part which is connected to them enable the functional Q groups to enter into interaction with the active sites of the tryptase. This is ensured when the dimensions of the head groups and of the linker enable the inhibitors to penetrate into the cavity or channel which is formed by the four tryptase monomer units in the tetramer. In this connection, account has also, in particular, to be taken of the restriction of the entrance of the channel to about 52 Å×32 Å. An inhibitor which is preferred in accordance with the invention therefore comprises head groups and a linker which permit the inhibitors to penetrate through an entrance having the dimensions 52 Å×32 Å, preferably 50 Å×30 Å and particularly preferably 40 Å×25 Å. Such a penetration is ensured when the dimensions of the head groups and of the linker are the same as, or smaller than, the abovementioned dimensions. However, it is also possible to use an inhibitor whose head groups and linker are in themselves larger and which nevertheless permit penetration due to conformational changes in the inhibitor and/or in the channel of the tetrameric tryptase.

The bifunctional inhibitors according to the invention are characterized in that they are able to bind simultaneously to two catalytic centers, in particular belonging to two different tryptase monomer units. All groups which are able to enter into interactions with a carboxylate group can be used as a Q group in this context. Preferably, the Q group is a basic group, in particular a proton donor. Particular preference is given to a Q group which is selected from

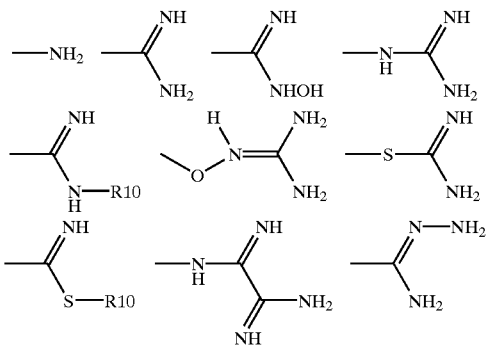

where R10 is 1–4 C-alkyl. According to the invention, the functional Q groups, which can be part of a head group or themselves constitute a head group, are connected by suitable linkers such that the geometry requirements claimed in accordance with the invention are met. In this context, the linker L can be a rigid structural component such that the Q groups are in principle present at the desired distance of from 20 to 45 Å from each other. However, the linker can also be a flexible structural component as long as it is only possible for the linker L to assume a conformation in which the Q groups are present at the desired distance of from 20 to 45 Å from each other.

As has already been mentioned, the geometric arrangement of the functional groups is of fundamental importance for the ability of selected molecules to be effective bifunctional inhibitors of human tryptase.

A preferred bifunctional tryptase inhibitor according to the invention therefore has the formula I

(I)

with H1 and H2 being identical or different and in each case comprising a Q group which is able to enter into interactions with a carboxylate group, with the linker L being able to assume a conformation which is such that the Q groups of the two head groups are present at a distance of from 20 to 45 Å from each other, with the sizes of the head groups and of the linker permitting the inhibitor to penetrate into a cavity having the dimensions 52 Å×32 Å×40 Å, and with L being

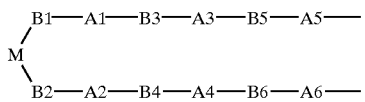

in which

A1 and A2 are identical or different and are —C(O)—, —NH—, —O— (oxygen), —S— (sulfur), —S(O)₂—, —S(O)₂—NH—, —NH—S(O)₂—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

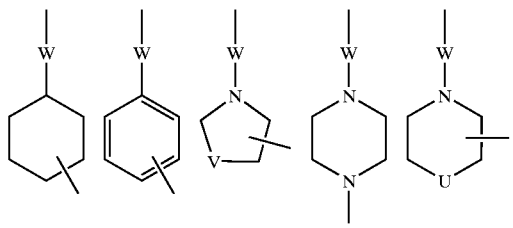

where

U is —O— (oxygen) or —CH₂— (methylene),

V is —O— (oxygen), —S— (sulfur) or —CH₂— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

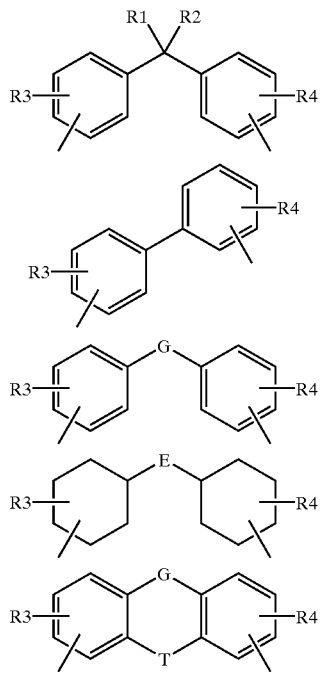

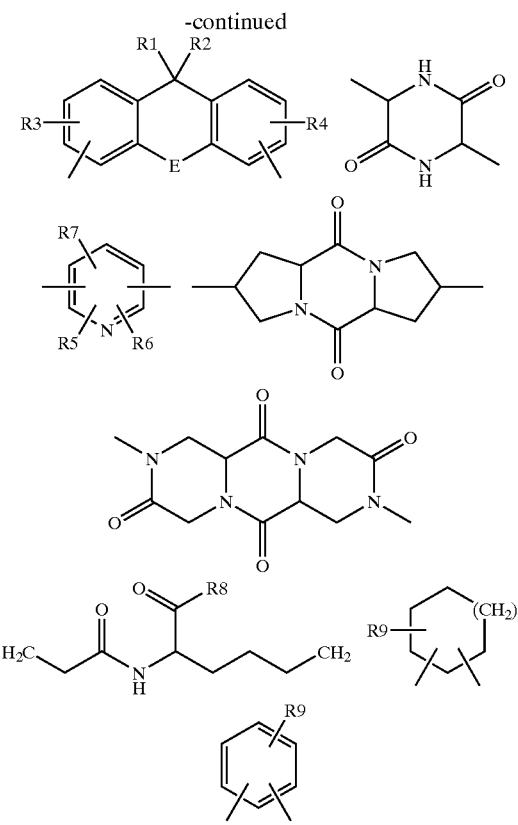

where

R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon, R3 and R4 are identical or different and are hydrogen or one, two or three identical or different 1–4C-alkyl radicals, E is —CH₂—, —O— or a bond, G is —S—, —O— or —S(O)₂—, T is —CH₂—, —O— or a bond, R5 and R6 are identical or different and are hydrogen or 1–4C-alkyl, R7 is hydrogen, 1–4C-alkyl, phenyl or pyridyl, R8 is 1–4C-alkoxy, N(R81)R82, piperidino or morpholino, R81 and R82 are identical or different and are hydrogen or 1–4C-alkyl, R9 is hydrogen or one, two or three identical or different 1–4C-alkyl radicals, n is 0, 1, 2 or 3, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and selected from the following groups

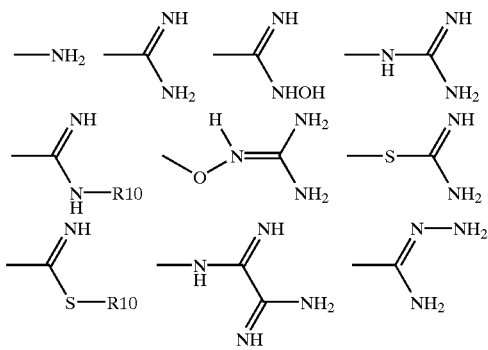

where

R10 is 1–4C-alkyl,

Y1 and Y2 are identical or different and are a 4–11C-heteroaryl or 2–7C-heterocycloalkyl radical which contains at least one ring nitrogen which can function as a proton acceptor or proton donor, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

1–4C-Alkyl represents straight-chain or branched alkyl radicals having from 1 to 4 carbon atoms. The butyl, the iso-butyl, the sec-butyl, the tert-butyl, the propyl, the isopropyl, the ethyl and the methyl radical may be mentioned by way of example.

Examples of 1–4C-alkyl which is entirely or partially substituted by fluorine which may be mentioned are the 2,2,3,3,3-pentafluoropropyl, the perfluoroethyl, the 1,2,2-trifluoroethyl, the 1,1,2,2-tetrafluoroethyl, the 2,2,2-trifluoroethyl, the trifluoromethyl and the difluoromethyl radicals.

Examples of a 5- or 6-membered cyclic hydrocarbon which may be mentioned are cyclopentane or cyclohexane.

1–4C-Alkoxy represents radicals which, in addition to the oxygen atom, contain a straight-chain or branched alkyl radical having from 1 to 4 carbon atoms. The butoxy, the iso-butoxy, the sec-butoxy, the tert-butoxy, the propoxy, the isopropoxy and, preferably, the ethoxy and the methoxy radical may be mentioned by way of example.

1–4C-Alkylene represents straight-chain or branched 1–4C-alkylene radicals, for example the methylene [—$CH_2$—], the ethylene [—$CH_2$—$CH_2$—], the trimethylene [—$CH_2$—$CH_2$—$CH_2$—], the tetramethylene [—$CH_2$—$CH_2$—$CH_2$—$CH_2$—], the 1,2-dimethylethylene [—CH($CH_3$)—CH($CH_3$)—], the 1,1-dimethylethylene [—C($CH_3$)$_2$—$CH_2$—], the 2,2-dimethylethylene [—$CH_2$—C($CH_3$)$_2$—], the isopropylidene [—C($CH_3$)$_2$—] or the 1-methylethylene [—CH($CH_3$)—$CH_2$—] radical.

1–3C-Alkylene represents straight-chain or branched 1–3C-alkylene radicals, for example the methylene [—$CH_2$—], the ethylene [—$CH_2$—$CH_2$—], the trimethylene [—$CH_2$—$CH_2$—$CH_2$—], the isopropylidene [—C($CH_3$)$_2$—] or the 1-methylethylene [—CH($CH_3$)—$CH_2$—] radical.

If m has the meaning 0, the group —(C(O))$_m$— is then a bond.

If p has the meaning 0, the group —(C(O))$_p$— is then a bond.

If n has the meaning 0, the group —($CH_2$)$_n$— is then a bond.

4–11C-Heteroaryl is an optionally substituted monocyclic or bicyclic aromatic hydrocarbon which contains from 4 to 11 C atoms and at least one ring nitrogen atom; in addition, one or more of the carbon atoms can be replaced by ring heteroatoms selected from the group O, N or S. In bicycles, at least one of the rings is aromatic. Pyrid-4-yl, pyrid-3-yl, pyrimidin-5-yl, imidazol-1-yl and benzimidazol-5-yl may be mentioned by way of example.

2–7C-Heterocycloalkyl is an optionally substituted monocyclic saturated or partially saturated hydrocarbon which contains from 2 to 7 C atoms and at least one ring nitrogen atom; in addition, one or more carbon atoms can be replaced by ring heteroatoms selected from the group O, N or S. Piperid-4-yl, piperazin-1-yl, pyrrolidin-2-yl, pyrrolidin-3-yl, imidazolidin-1-yl, imidazolidin-2-yl, imidazolidin-4-yl and morpholin-2-yl may be mentioned by way of example.

5–12C-Arylene is an optionally substituted divalent monocyclic or bicyclic aromatic hydrocarbon radical which possesses from 5 to 12 C atoms, with at least one of the rings being aromatic in the case of the bicyclic aromatic hydrocarbon radicals. The free valencies can both be located on the aromatic ring or on the nonaromatic ring, or one can be located on the aromatic ring and one on the nonaromatic ring. 1,4-Phenylene, 1,3-phenylene, 1,4-naphthylene and 2,6-naphthylene may be mentioned by way of example.

5–12C-Heteroarylene is an arylene radical, as previously defined, in which from 1 to 4 C atoms are replaced by heteroatoms selected from the group O, N and S. 2,5-Furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,5-benzofuranylene, 2,6-quinolinylene and 4,2-thiazolylene may be mentioned by way of example.

3–8C-Cycloalkylene is an, optionally substituted, divalent monocyclic saturated or partially saturated hydrocarbon radical which possesses from 3 to 8 C atoms. The 1,3-cyclopentylene, the 1,3-cyclohexylene and, preferably, the 1,4-cyclohexylene radical may be mentioned by way of example.

3–8C-Heterocycloalkylene is a cycloalkylene radical, as previously defined, in which from 1 to 3 C atoms are replaced by heteroatoms selected from the group O, N and S. The 1,4-piperidinylene, the 1,4-piperazinylene, the 2,5-pyrrolidinylene, the 4,2-imidazolidinylene and, preferably, the 4,1-piperidinylene radical may be mentioned by way of example.

1–4C-Alkoxycarbonyl is a carbonyl group to which one of the abovementioned 1–4C-alkoxy radicals is bonded. The methoxycarbonyl ($CH_3O$—C(O)—) and the ethoxycarbonyl ($CH_3CH_2O$—C(O)—) radical may be mentioned by way of example.

1–4C-Alkylcarbonyloxy is a carbonyloxy group to which one of the abovementioned 1–4C-alkyl radicals is bonded. The acetoxy radical ($CH_3C(O)$—O—) may be mentioned by way of example.

Several of the groups listed under M possess, either in themselves or due to their substitution, one or more chiral centers. The invention therefore encompasses both all the pure enantiomers and all the pure diastereomers and also their mixtures in any mixing ratio.

The groups Z1 and Z2, respectively, are located, by definition, between the groups B9 and B11 (-B9-Z1-B11-) and B10 and B12 (-B10-Z2-B12-), resepctively. Correspondingly, in the divalent groups (e.g. 2,6-indolylene) which are mentioned by way of example, the first number is that of the site for linkage to the B9 or B10 group, respectively, and the second number is that of the site for linkage to the B11 or B12 group, respectively.

Depending on substitution, all acid addition salts or all salts with bases are suitable salts for compounds of the formula I. Those which may in particular be mentioned are the pharmacologically tolerated salts of the inorganic and organic acids which are customarily used in pharmacy. Suitable salts of this nature are, on the one hand, water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluene-sulfonic acid, methanesulfonic acid or 3-hydroxy-2-naphthoic acid, with the acids being employed, when preparing the salt, in an equimolar quantity ratio or in a quantity ratio which differs from this depending on whether the acid is a monobasic or polybasic acid and on which salt is desired.

On the other hand, salts with bases are also suitable. Examples of salts with bases which may be mentioned are alkali (lithium, sodium or potassium) or calcium, aluminum, magnesium, titanium, ammonium, meglumin or guanidinium salts, with the bases also in this case being employed, when preparing the salt, in an equimolar quantity ratio, or in a quantity ratio which differs from this.

Salts which are not pharmacologically tolerated and which can, for example, initially arise as process products when producing the compounds according to the invention on an industrial scale, are converted into pharmacologically tolerated salts using methods known to the skilled person.

The skilled person knows that the compounds according to the invention, and also their salts, when they are isolated in crystalline form, for example, can contain varying quantities of solvents. The invention therefore also encompasses all solvates and, in particular, all hydrates of the compounds of the formula I, as well as all solvates and, in particular, all hydrates of the salts of the compounds of the formula I.

One embodiment (embodiment a) of the compounds according to the invention of the formula I is that in which L is

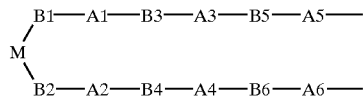

and

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

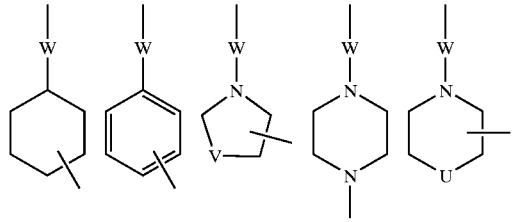

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

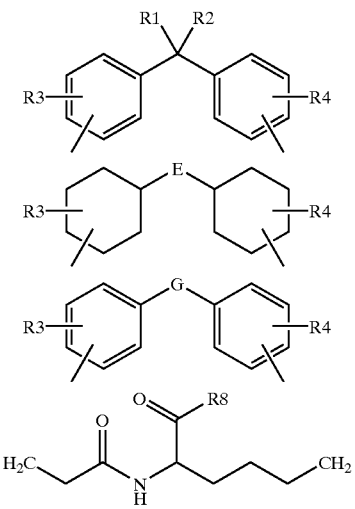

where

R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S—, —O— or —S(O)$_2$—, R8 is 1–4C-alkoxy, N(81)R82, piperidino or morpholino, R81 and R82 are identical or different and are hydrogen or 1–4C-alkyl, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

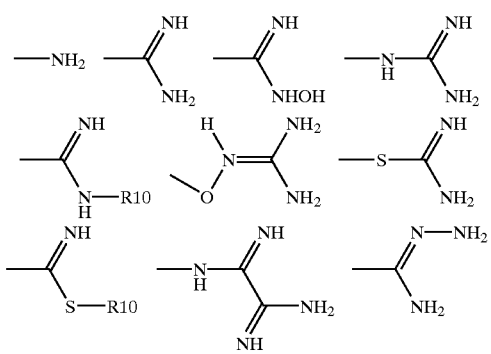

where

R10 is 1–4C-alkyl,

Y1 and Y2 are identical or different and are a 4–11C-heteroaryl or 2–7C-heterocycloalkyl radical which contains at least one ring nitrogen which can function as a proton acceptor or proton donor, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment a which are to be emphasized are those in which

A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

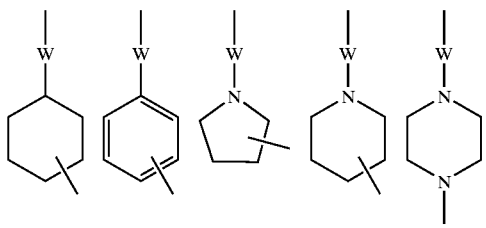

where

W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

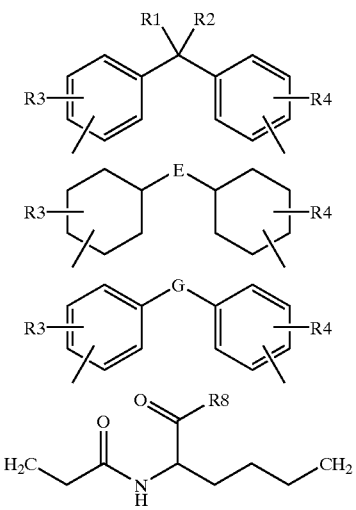

where

R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S—, —O— or —S(O)$_2$—, R8 is 1–4C-alkoxy, N(R81)R82, piperidino or morpholino, R81 and R82 are identical or different and are hydrogen or 1–4C-alkyl, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8— (C(O))$_p$-B10-Z2-B12-X2, B1, B2, B3, B4, B5 and B6 are identical or different and are a bond or straight-chain or branched 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

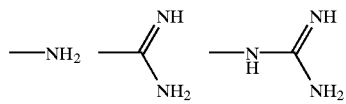

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazol-idin-4-yl, 2-imidazolin-3-yl, 2-imidazolin-2-yl, imidazol-1-yl, imidazol-2-yl, imidazol-4-yl, 5-methylimidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or carbonyl groups.

Compounds of embodiment a which are in particular to be emphasized are those in which A1 and A2 are identical or different and are —O— (oxygen) or —NH—C(O)—, A3 and A4 are identical or different and are —C(O)—NH— or are selected from the group

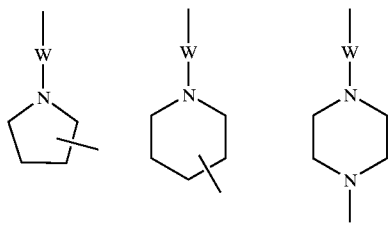

where W is the group —C(O)— or a bond,

A5 and A6 are identical or different and are —C(O)—, —C(O)—NH—, —NH—C(O)— or a bond, M is selected from one of the following groups

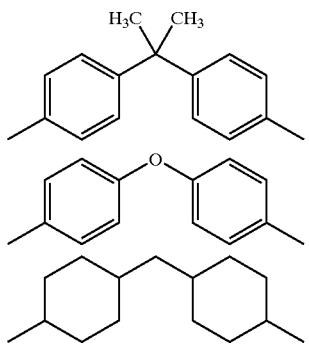

H1 is -B7-(C(O))$_m$-B9-X1 or -B7-(C(O))$_m$-B9-Z1-B11-X1,

H2 is -B8-(C(O))$_p$-B10-X2 or -B8-(C(O))$_p$-B10-Z2-B12-X2,

B1, B2, B3, B4, B5 and B6 are identical or different and are a bond or —CH$_2$— (methylene), B7, B8, B9, B10, B11 and B12 are identical or different and are a bond or 1–2C-alkylene, m is 0 or 1, p is 0 or 1, X1 and X2 are identical or different and are amino, amidino or guanidino, Z1 and Z2 are identical or different and are 1,4-phenylene, 1,3-phenylene, 1,4-cyclohexylene or 1,4-piperazinylene, the salts of these compounds, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Preferred compounds of embodiment a are those in which

A1 and A2 are identical or different and are —O— (oxygen) or —NH—C(O)—,

A3 and A4 are identical or different and are —C(O)—NH— or are selected from the group

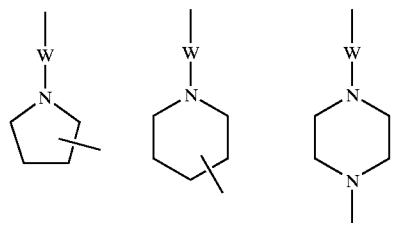

where W is the group —C(O)— or a bond,

A5 and A6 are identical or different and are —C(O)—, —NH—C(O)— or a bond,

M is selected from one of the following groups

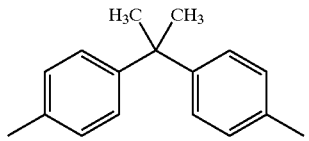

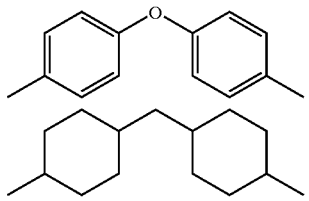

H1 is -B7-(C(O))$_m$-B9-Z1-B11-X1,

H2 is -B8-(C(O))$_p$-B10-Z2-B12-X2,

B1, B2, B3, B4, B5 and B6 are identical or different and are a bond or —CH$_2$— (methylene), B7, B8, B9, B10, B11 and B12 are identical or different and are a bond or —CH$_2$— (methylene), m is 0 or 1, p is 0 or 1, X1 and X2 are identical or different and are amino, amidino or guanidino, Z1 and Z2 are identical or different and are 1,4-phenylene, 1,3-phenylene, 1,4-cyclohexylene or 1,4-piperazinylene, the salts of these compounds, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Particularly preferred compounds of embodiment a are bis{4-[4-(4-aminomethylcyclohexanoyl)piperazin-1-yl]-carbonyl}-4,4'-diaminodiphenyl ether, bis{4-[(3-aminomethyl)benzoylpiperazin-1-yl]carbonyl}-4,4'-diaminodiphenyl ether, di{4-[4-(4-aminomethyl)cyclohexanoylamino]piperidin-1-ylcarbamoyl}cyclohexylmethane, 2,2-bis[4-(4-guanidinylbenzylamino)carbonylmethoxyphenyl]-propane, 2,2-bis[4-(10-amino-3,6-diaza-2,5-dioxodecyloxyphenyl]propane and 2,2-bis{4-[4-(4-aminomethylbenzylcarbamoyl)-1-piperazinylcarbonyloxy]phenyl}propane, and also the salts of these compounds.

Another embodiment (embodiment b) of the compounds according to the invention of the formula I is that in which L is

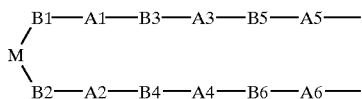

and

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

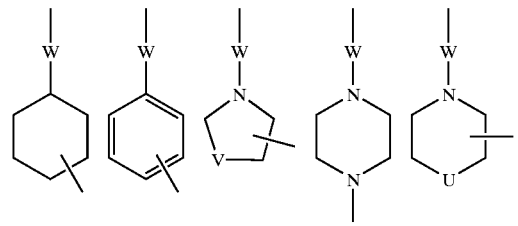

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

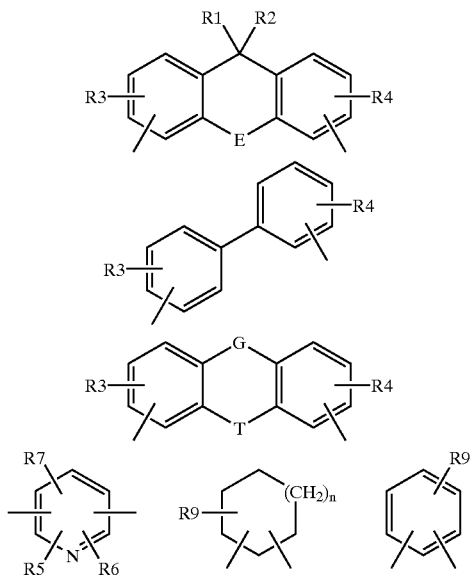

where

R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S—, —O— or —S(O)$_2$—, T is —CH$_2$—, —O— or a bond, R5 and R6 are identical or different and are hydrogen or 1–4C-alkyl, R7 is hydrogen, 1–4C-alkyl, phenyl or pyridyl, R9 is hydrogen or one, two or three identical or different 1–4C-alkyl radicals, n is 0, 1, 2 or 3, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and selected from the following groups where R10 is 1–4C-alkyl, Y1 and Y2 are identical or different and are a 4–11C-heteroaryl or 2–7C-heterocycloalkyl radical which contains at least one ring nitrogen which can function as a proton acceptor or proton donor, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment b which are to be emphasized are, on the one hand, those in which A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group where U is —O— (oxygen) or —CH$_2$— (methylene), V is —O— (oxygen), —S— (sulfur) or —CH$_2$— (methylene), and W is the group —C(O)— or a bond, A5 and A6 are identical or different and are —C(O)—, —NH—, —O—, —S—, —C(O)—NH—, —NH—C(O)—, —O—C(O)—, —C(O)—C— or a bond, M is selected from one of the following groups where R1 and R2 are identical or different and are 1–4C-alkyl which is wholly or partially substituted by fluorine, or R1 and R2 together, and including the carbon atom to which they are bonded, are a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S(O)$_2$—, T is —CH$_2$—, —O— or a bond, R5 and R6 are identical or different and are hydrogen or 1–4C-alkyl, R7 is pyridyl, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

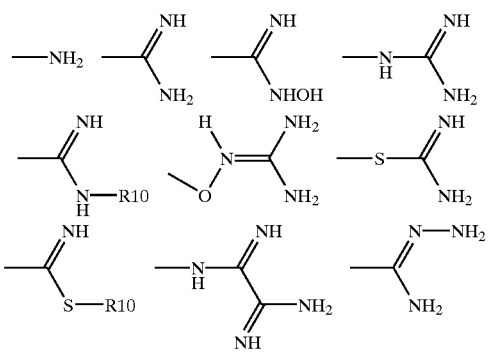

where

R10 is 1–4C-alkyl,

Y1 and Y2 are identical or different and are a 4–11C-heteroaryl or 2–7C-heterocycloalkyl radical which contains at least one ring nitrogen which can function as a proton acceptor or proton donor, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

On the other hand, compounds of embodiment b which are to be emphasized are those in which A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

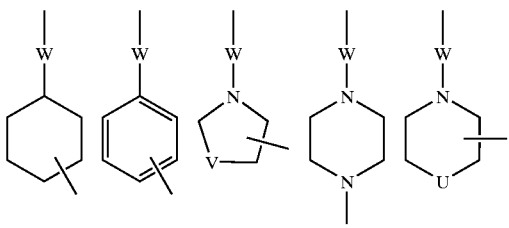

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

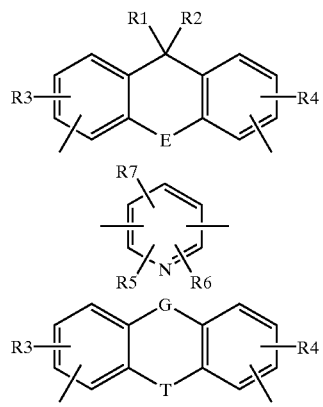

where

R1 and R2 are identical or different and are 1–4C-alkyl or together, and including the carbon atom to which they are bonded, are carbonyl, R3 and R4 are identical or different and are hydrogen or one, two or three identical or different 1–4C-alkyl radicals, E is —CH$_2$—, —O— or a bond, G is —O— (oxygen) or —S— (sulfur), T is —CH$_2$—, —O— or a bond, R5 and R6 are identical or different and are hydrogen or 1–4C-alkyl, R7 is hydrogen, 1–4C-alkyl or phenyl, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

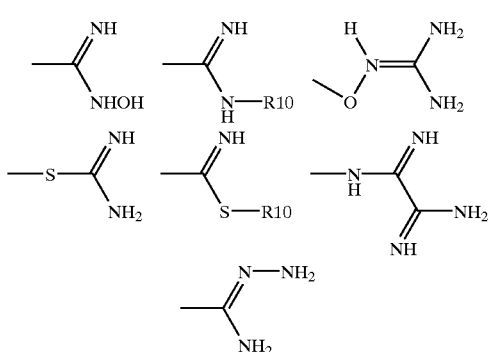

where

R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 114 4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment b which are furthermore to be emphasized are those in which A1 and A2 are identical or different and are —C(O)—, —NH—, —O— (oxygen), —S— (sulfur)—, —S(O)$_2$—, —NH—S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

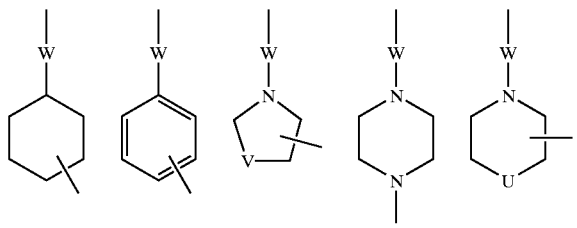

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

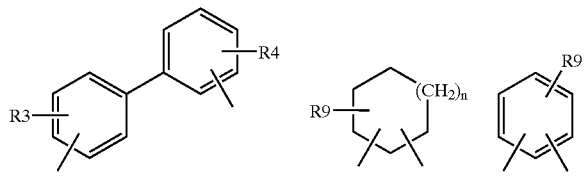

where

R3 and R4 are identical or different and are hydrogen or one, two or three identical or different 1–4C-alkyl radicals, R9 is hydrogen or one, two or three identical or different 1–4C-alkyl radicals, n is 0, 1, 2 or 3, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

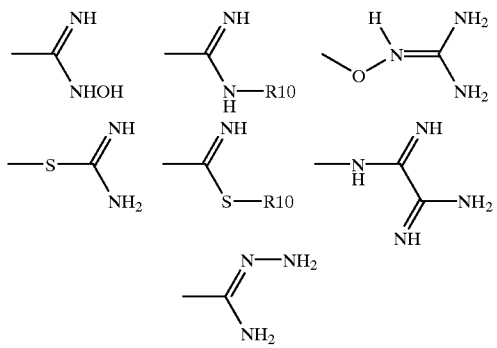

where

R10 is 1–4C-alkyl

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thioncarbonyl group.

Compounds of embodiment b which are in particular to be emphasized are, on the one hand, those in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

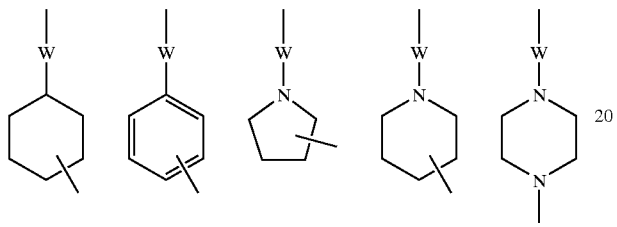

where w is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

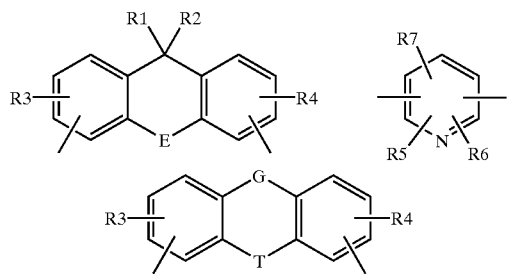

where

R1 and R2 are identical or different and are 1–4C-alkyl which is wholly or partially substituted by fluorine, or R1 and R2 together, and including the carbon atom to which they are bonded, are a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S(O)$_2$—, T is —CH$_2$—, —O— or a bond, R5 and R6 are identical or different and are hydrogen or 1–4C-alkyl, R7 is pyridyl, H1 is -B7-(C(O))$_m$-B9-X1, -B7-(C(O))$_m$-B9-Y1 or -B7-(C(O))$_m$-B9-Z1-B11-X1, H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

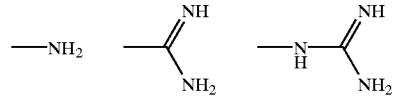

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazolidin-4-yl, 2-imidazolin-3-yl, 2-imidazolin-2-yl, imidazol-1-yl, imidazol-2-yl, imidazol-4-yl, 5-methylimidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Compounds of embodiment b which are in particular to be emphasized are, on the other hand, compounds of the formula I in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

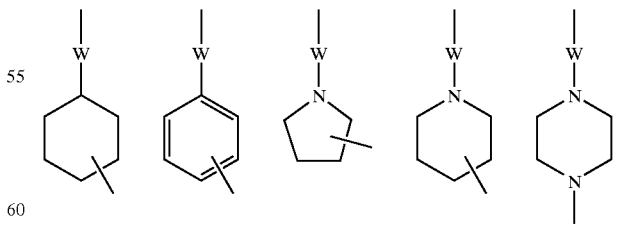

where

W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

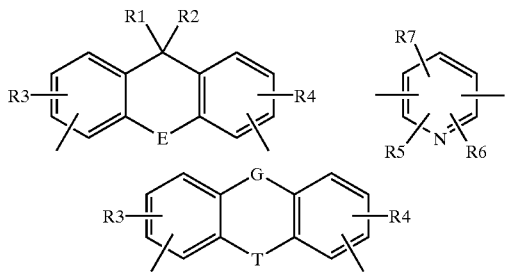

where
R1 and R2 are identical or different and are 1–4C-alkyl or together, and including the carbon atom to which they are bonded, are carbonyl,
R3 and R4 are identical or different and are hydrogen or one, two or three identical or different 1–4C-alkyl radicals,
E is —CH$_2$—, —O— or a bond,
G is —O— (oxygen) or —S— (sulfur),
T is —CH$_2$—, —O— or a bond,
R5 and R6 are identical or different and are hydrogen or 1–4C-alkyl,
R7 is hydrogen, 1–4C-alkyl or phenyl,
H1 is -B7-(C(O))$_m$-B9-X1, -B7-(C(O))$_m$-B9-Y1 or -B7-(C(O))$_m$-B9-Z1-B11-X1,
H2 is -B8-(C(O))$_p$-B10-X2, -B8-(C(O))$_p$-B10-Y2 or -B8-(C(O))$_p$-B10-Z2-B12-X2,
B1, B2, B3, B4, B5 and B6 are identical or different and are a bond or 1–4C-alkylene,
B7, B8, B9, B10, B11 and B12 are identical or different and are a bond or 1–3C-alkylene,
m is 0 or 1,
p is 0 or 1,
X1 and X2 are identical or different and are selected from the following groups

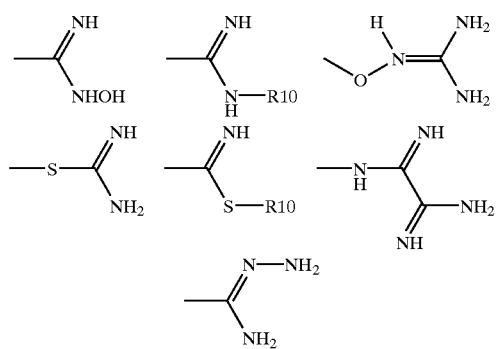

where
R10 is 1–4C-alkyl,
Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl,
Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene,
the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Compounds of embodiment b which are in particular to be emphasized are furthermore those in which
A1 and A2 are identical or different and are —C(O)—, —NH—, —O— (oxygen), —C(O)—NH—, —NH—C(O)—, —O—C(O)—, —C(O)—O— or a bond,
A3 and A4 are identical or different and are —C(O)—, —O—, —NH—, —O—C(O)—, —C(O)—O—, —C(O)—NH—, —NH—C(O)— or a bond, or are selected from the group

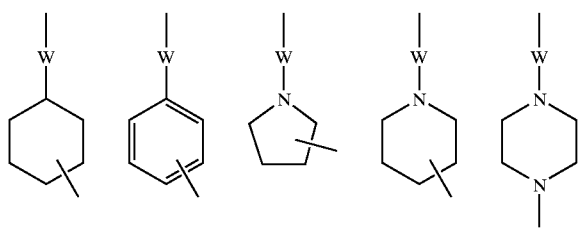

where
W is the group —C(O)— or a bond,
A5 and A6 are identical or different and are —C(O)—, —NH—, —O—, —C(O)—NH—, —NH—C(O)—, —O—C(O)—, —C(O)—O— or a bond,
M is selected from one of the following groups

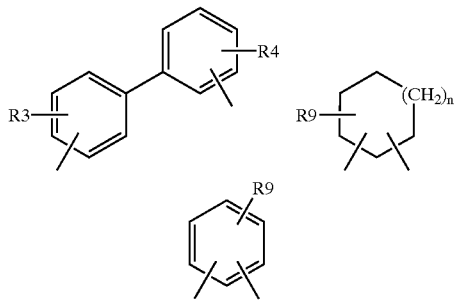

where
R3 and R4 are identical or different and are hydrogen or one, two or three identical or different 1–4C-alkyl radicals,
R9 is hydrogen or one, two or three identical or different 1–4C-alkyl radicals,
n is 0, 1, 2 or 3,
H1 is -B7-(C(O))$_m$-B9-X1, -B7-(C(O))$_m$-B9-Y1 or -B7-(C(O))$_m$-B9-Z1-B11-X1,
H2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

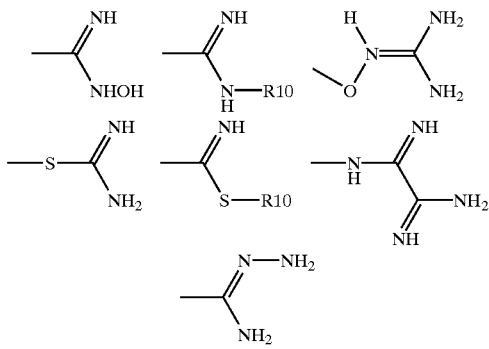

where

R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Compounds of embodiment b which are in particular to be emphasized are, in addition, pyridine-2,6-dicarbobis[4-(3-aminomethylbenzoyl)-1-piperazide], pyridine-2,6-dicarbobis[4-(trans-4-aminomethylcyclohexanoyl)-1-piperazide], 2,6-dimethyl-4-phenylpyridine-3,5-dicarbobis[4-(3-aminomethylbenzoyl)-1-piperazide], pyridine-2,6-dicarbobis[4-(3-aminomethylbenzoylamino)-1-piperidide] and pyridine-2,6-dicarbobis[4-(4-aminomethylcyclohexylcarbonylamino)-1-piperidide], and also the salts of these compounds.

A further embodiment (embodiment c) of the compounds of the formula I is that in which L is

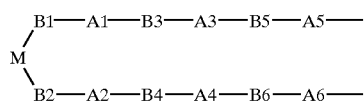

and

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

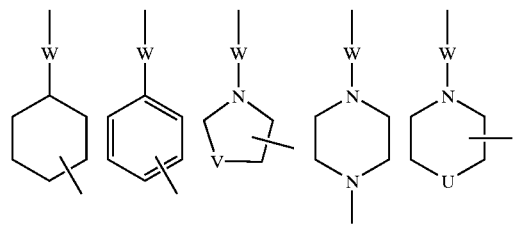

where

U is —O— (oxygen) or CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

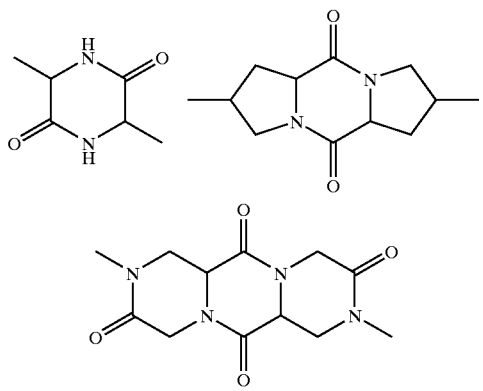

H1 is -B7-(C(O))$_m$-B9-X1, -B7-(C(O)),-B9-Y1 or -B7-(C(O))$_m$-B9-Z1-B11-X1,

H2 is -B8-(C(O))$_p$-B10-X2, -B8-(C(O))$_p$-B10-Y2 or -B8-(C(O))$_p$-B10-Z2-B12-X2,

B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

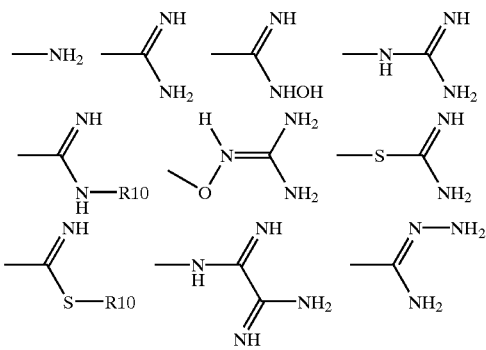

where

R10 is 1–4C-alkyl,

Y1 and Y2 are identical or different and are a 4–11C-heteroaryl or 2–7C-heterocycloalkyl radical which contains at least one ring nitrogen which can function as a proton acceptor or proton donor, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment c which are to be emphasized are those in which

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

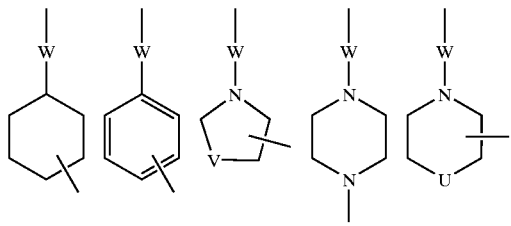

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

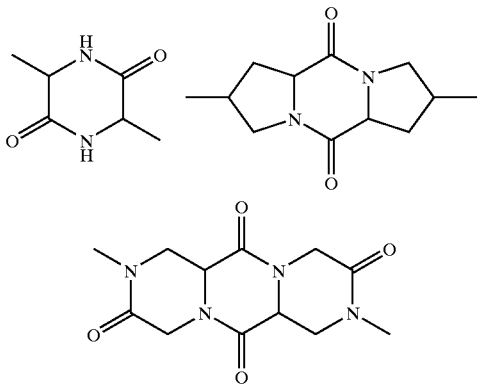

H1 is -B7-(C(O))$_m$-B9-X1, -B7-(C(O))$_m$-B9-Y1 or -B7-(C(O))$_m$-B9-Z1-B11-X1,

H2 is -B8-(C(O))$_p$-B10-X2, -B8-(C(O))$_p$-B10-Y2 or -B8-(C(O))$_p$-B10-Z2-B12-X2,

B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

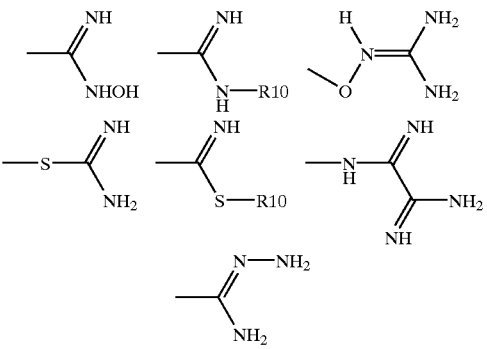

where

R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, 84, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment c which are in particular to be emphasized are those in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

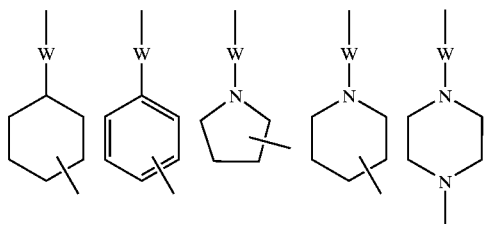

where
W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

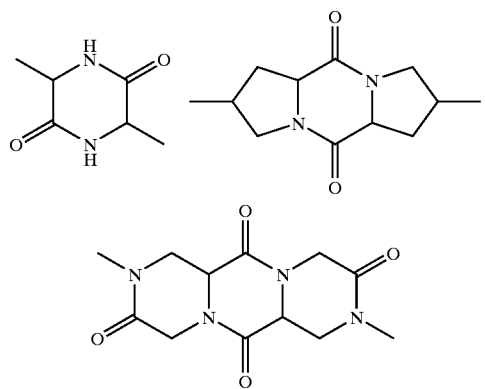

H1 is -B7-(C(O))$_m$-B9-X1, -B7-(C(O))$_m$-B9-Y1 or -B7-(C(O))$_m$-B9-Z1-B11-X1,

H2 is -B8-(C(O))$_p$-B10-X2, -B8-(C(O))$_p$-B10-Y2 or -B8-(C(O))$_p$-B10-Z2-B12-X2,

B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

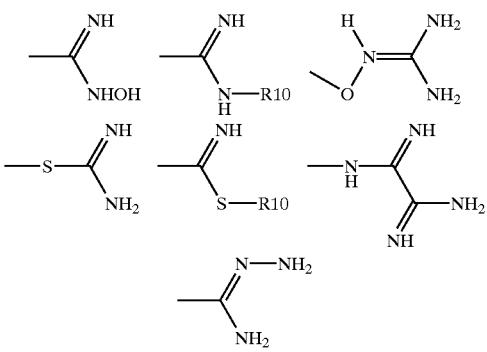

where
R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

In addition to the interaction with Asp189, the Q groups can also enter into interactions with the functional groups of one or more of the amino acids carbonyl-Gly219, carbonyl-Ser190 and/or Tyr228 of the respective tryptase subunit, either directly or with the mediation of water molecules.

The head groups H1 and/or H2 can possess additional functional groups which, directly or with the mediation of water molecules, exhibit interactions with respect to functional groups of one or more of the amino acids Ser195 Oγ, Ser190 Oγ, carbonyl-Ser190, carbonyl-Gly216, carbonyl-Gly219, NH-Gly219 and/or Ser214 of the respective tryptase subunit. The precise distances between the binding sites of the groups of a tryptase subunit can be ascertained from the crystal structure data.

In addition, the head groups H1 and/or H2 can preferably comprise a charged group which is able to enter into hydrogen bond interactions with Gln192 and also electrostatic interactions with the carboxylate groups of Asp143 and/or Asp147 of the tryptase.

Furthermore, the bifunctional inhibitor according to the invention can possess a group, in the head groups H1 and/or H2, which is able to enter into interactions with the S2 region.

The head groups H1 and/or H2 can furthermore possess a group, preferably a short group, which is able to enter into an interaction with the polar or nonpolar side chains of Thr96, Ala97 and Gln98 and with Tyr95 and Thr96 and Gln98 of the neighboring subunits (A and D or B and C, respectively) of the tryptase in the S3/S4 region.

Besides this, the head groups H1 and/or H2 can also comprise positively charged groups which are able to enter into electrostatic interactions with the carboxylate group of Glu 217 of the tryptase in the S3/S4 pocket. A further improvement of the overall binding can be achieved by means of head groups H1 and/or H2 which are able to enter into electrostatic interactions with the electronegative field around S3/S4 and S6 of the tryptase units.

The invention also encompasses a bifunctional inhibitor, as described above, in which the Q groups of the two head groups are held, by the linker L, at a distance from each other of from 34 to 56 Å, such that they are able to enter into interactions with the carboxylate groups of Asp189 of the tryptase subunits A and B or A and C or B and D or C and D.

The invention encompasses both symmetrical and asymmetrical bifunctional inhibitors. What is essential is that the head groups are present at a distance from each other which enables them to interact with the substrate specificity pocket of the individual tryptase subunits.

The inhibitors according to the invention preferably have a Ki value <100 $\mu$mol, in particular <1 $\mu$mol, particularly preferably <100 nmol and most preferably <10 nmol.

The invention also encompasses a bifunctional inhibitor, as described above, which comprises one or two additional functional Q groups which are arranged such that they are able to enter into interactions with additional substrate specificity pockets belonging to additional tryptase monomers in the tryptase tetramer. A multifunctional inhibitor of this nature has to be constructed geometrically in such a way that it fulfills the basic geometric conditions, specified in FIG. 1, for the functional Q groups and for the total size of the molecule.

The compounds of the formula I are composed of a large number of divalent building blocks (M, A1, A2, A3, A4, A5, A6, B1, B2, B3, B4, B5, B6, B7, B8, B9, B10, B11, B12, Z1 and Z2). In principle, they can be synthesized starting from any one of these building blocks. In the case of compounds of the formula I which are constructed to a large extent symmetrically, preference is given to starting the synthesis with the central building block M; by contrast, it can be advantageous to synthesize compounds of the formula I which are predominantly asymmetrical starting with one of the end groups H1 or H2.

In this connection, the building blocks are always linked together in accordance with the same pattern, which is known per se to the skilled person.

The skilled person knows that the compounds of the formula I can be synthesized building block by building block; alternatively, relatively large fragments, consisting of several individual building blocks, can first of all be constructed, with these fragments then being assembled into the whole molecule.

Amino [—NH—], ether [—O—], thioether [—S—], keto [—C(O)—], thioketo [—C(S)—], sulfonyl [—S(O)$_2$—], ester [—O—C(O)—, —C(O)—O—], amide [—C(O)—NH—, —NH—C(O)—], sulfonamide [—SO$_2$—NH—, —NH—SO$_2$—], carbamate [—NH—C(O)—O—, —O—C(O)—NH—], carbamide (—NH—C(O)—NH—) or carbonate [—O—C(O)—O—] bridges occur in the compounds of the formula I as a result of the meanings which the individual building blocks of the compounds of the formula I can assume.

The manner in which such bridges are prepared is known per se to the skilled person, and suitable methods, and starting compounds for preparing them, are described, for example, in March, Advanced Organic Chemistry, Reactions, Mechanisms and Structure, Third Edition, 1985, John Wiley & Sons.

For example, ether and thioether bridges can be prepared by the method of Williamson.

Keto or thioketo bridges can, for example, be introduced as components of larger building blocks, such as 1,3-dichloroacetone.

Sulfonyl bridges can be obtained, for example, by oxidizing thioether bridges.

A large number of methods are known for synthesizing ester bridges. Mention may be made here, by way of example, of the reaction of acids with alcohols, preferably using $H_2SO_4$ or p-toluenesulfonic acid as catalyst; or with the addition of a water-extracting agent, such as a molecular sieve or a carbodiimide. The reaction of acid chlorides with alcohols may also be mentioned at this point.

There is also a large number of known methods for preparing amide bridges. The reaction of acid chlorides with primary or secondary amines may be mentioned here as an example. In addition, reference may also be made to all the methods which have been developed for peptide chemistry. Correspondingly, sulfonamide bridges can be synthesized from sulfonyl chlorides and primary or secondary amines.

Carbamate bridges can be prepared, for example, by reacting chlorocarbonic esters with amines. The chlorocarbonic esters can, for their part, be synthesized from alcohols and phosgene. The addition of alcohols to isocyanates constitutes another variant for synthesizing carbamate bridges.

In a similar way to carbamate bridges, carbonate bridges can be prepared from chlorocarbonic esters by reacting them with alcohols (instead of amines).

Carbamide bridges can be prepared, for example, by reacting isocyanates with amines.

The N oxidation is effected in a manner with which the skilled person is also familiar, for example using m-chloroperoxybenzoic acid in dichloromethane at room temperature. The skilled person is familiar, on the basis of his specialist knowledge, with the detailed reaction conditions which are required for carrying out the method.

The substances according to the invention are isolated and purified in a manner known per se, for example by the solvent being distilled off in vacuo and the resulting residue being recrystallized from a suitable solvent or being subjected to one of the customary purification methods such as column chromatography on a suitable support material.

Salts are obtained by dissolving the free compound in a suitable solvent, for example in a chlorinated hydrocarbon, such as methylene chloride or chloroform, or a low molecular weight aliphatic alcohol (ethanol, isopropanol), which contains the desired acid or base, or to which the desired acid or base is subsequently added. The salts are isolated by filtering, reprecipitation or precipitation with a substance which does not dissolve the addition salt, or by evaporating off the solvent. Resulting salts can be converted, by alkalizing or acidifying, into the free compounds, which can be converted into salts once again. In this way, salts which are not tolerated pharmacologically can be converted into salts which are tolerated pharmacologically.

The preparation of compounds of the formula I may be demonstrated, by way of example, with the aid of the following Examples 4–14 and FIGS. 8–19. Other compounds of the formula I can be prepared analogously or using the methods which are cited above and which are known per se to the skilled person.

The invention furthermore relates to human tryptase in crystallized form. While such a crystallized tryptase was not previously known in the state of the art, it is of help for developing tryptase inhibitors. Such a crystallized human tryptase is characterized, in particular, by the tetragonal space group $P4_1$ and the cell coordinates a=b=83 Å±5 Å and c=127 Å±5 Å, preferably a=b=83 Å±2 Å and c=127 Å±2 Å and, particularly preferably, a=b=83 Å±1 Å and c=127 Å±1 Å. The crystals contain one tryptase tetramer per asymmetric unit.

The invention furthermore relates to a method for preparing human tryptase in crystallized form, wherein the crystals are obtained by vapor diffusion or dialysis. It is also possible to use another crystallization method which is customary and known to the skilled person. For crystallizing, the protein is preferably first of all inhibited, for example using an excess of 4-amidinophenylpyruvic acid (APPA). After concentrating, preferably to the order of magnitude of from 1 to 10 mg/ml, in particular from 3 to 5 mg/ml, for example in an 8 mM 2-(N-morpholino) ethanesulfonic acid buffer, the protein is, for example, equilibrated against 0.2M 3-(N-morpholino) propanesulfonic acid in ammonium sulfate. Suitable crystals are obtained by drop vapor diffusion (preferably by hanging or sitting drop vapor diffusion). The geometry of tryptase crystals can, in particular, be analyzed by means of X-ray structural analysis. The data which are obtained thereby can be used directly for developing suitable tryptase inhibitors. The invention therefore also encompasses a method for developing and/or identifying tryptase inhibitors, wherein the structure of the inhibitor is determined with the aid of the crystal structure data obtained from crystallized tryptase. This means, in particular, that the structure of possible inhibitors is modeled with the aid of the crystal structure data obtained from crystallized tryptase. In this way, it is possible, in particular, to develop bifunctional or polyfunctional inhibitors which exhibit a high efficacy and a high specificity for tryptase. However, it is also possible to develop monofunctional inhibitors. The method according to the invention can be used to develop compounds which inhibit tryptase without having to rely on elaborate trial and error experiments.

The invention furthermore relates to a pharmaceutical composition which comprises a tryptase inhibitor as described above. Such a pharmaceutical composition can, where appropriate, comprise customary pharmaceutical excipients and/or adjuvants. The pharmaceutical compositions according to the invention are of wide applicability because of the connection between tryptase and a large number of allergic and inflammatory diseases, such as, in particular, asthma, psoriasis, arthritis, gingivitis, peridontitis, rhinitis, conjunctivitis, dermatitis, anaphylaxis, rheumatoid arthritis, ARDS (adult respiratory distress syndrome), inflammations in the gastrointestinal region (Crohn's disease, inflammatory bowel disease), and others. In this connection, the tryptase inhibitor is present in a therapeutically effective quantity. The pharmaceutical composition can be used in all the application forms which are customary. It is preferably present in an application form for topical use. Examples of this are use as an aerosol or use as an ointment. However, it is also possible to prepare the pharmaceutical compositions according to the invention for oral or subcutaneous administration. Excipients which are suitable for this purpose are known to the skilled person and comprise, for example, customary tableting adjuvants or physiological salt solutions.

In systemic therapy (p.o. or i.v.), the dose of the active compounds is between 0.1 and 10 mg per kilogram and day.

Because of the high specificity which can be achieved using the bifunctional inhibitors according to the invention, the latter are also suitable for diagnosing diseases which are connected with tryptase. The invention therefore also relates to the use of a tryptase inhibitor according to the invention for diagnosing allergic and inflammatory diseases, in particular. Besides this, it is also possible to use the tryptase inhibitors according to the invention to investigate and elucidate the mechanism of action of tryptase in detail.

The invention will be further explained by means of the attached figures and the subsequent examples.

FIG. 1 shows a diagram of the tetrameric structure of tryptase in the form of a section (11).

The tryptase (11) has a frame-shaped form in which four structurally identical subunits (monomers) A (7), B (9), C (10) and D (8) occupy the corners and jointly enclose a central cavity (12). The subunits form specificity pockets (6) in their active centers. Asp189 residues (5) are one of the components of the specificity pockets (6) in the respective subunits. The distances [(13)–(18)] between the carboxyl groups of the Asp189 residues (5) in the respective subunits are between A (7) and B (9) 45 Å±1 Å (13), between A (7) and C (10) 45 Å±1 Å (14), between A (7) and D (8) 33 Å±1 Å (15), between B (9) and C (10) 33 Å±1 Å (16), between B (9) and D (8) 45 Å±1 Å (17), and between C (10) and D (8) 45 Å±1 Å (18).

The diagram also shows a tryptase inhibitor 1 whose head groups H1 (2) and H2 (3) interact with the carboxyl groups of the Asp189 residues (5) in the specificity pockets (6) of subunits A (7) and D (8) of the tryptase (11). The linker L (4) lies in the cavity (12) which is enclosed by the four subunits.

FIG. 2a shows a frontal view of a surface representation of a solid tryptase tetramer.

The four subunits (designated A to D) are related to each other by means of three twofold axes of symmetry: two axes which are perpendicular to each other along the boundary surfaces A-B/C-D and A-D/B-C, which lie in the plane of the paper, with the third being perpendicular to the other two, through the middle of the tetramer. The central, extended pore of tryptase is clearly visible. Small projections from each of the subunits partially conceal the entrance to this pore. The electrostatic potential of the surface is depicted by +(positively charged regions) and –(negatively charged regions) (in the attached illustration in color, blue depicts positively charged regions and red depicts negatively charged regions). The inhibitor 4-amidinophenylpyruvic acid (APPA), which lies on the active sites of each subunit, is designated I (yellow-green in color).

FIG. 2b shows the side view of the D and C units. An oblique, extended spot having a positive potential (+or blue) forms a possible, 108 Å long heparin binding site which spans the contact region between the two subunits. The length of this spot is compatible with the known stabilizing activity of heparin chains of 5.5 kDa (18 mer) in size and longer (Alter et al., Biochem. J. 248 (1987), 821–827). (The figure was generated using GRASP (Nichols et al., Biophys. J. 64 (1993) A166)).

FIG. 3 shows a stereotape representation of a tryptase monomer (A in the standard orientation) together with secondary structure elements and the APPA molecule. The residues of the active site are highlighted as are the unique surface loops of tryptase, namely (listed in the counterclockwise direction) the 37 loop, the 60 loop, the 97 loop, the 173 loop, the 147 loop and the 70 to 80 loop (the figure was produced using SETOR (S. V. Evans, J. Mol. Graphics 11 (1990), 134–138)).

FIG. 4 depicts an amino acid sequence comparison based on the structure of human mast cell tryptase II/β, bovine trypsin and bovine chymotrypsinogen A. Sequence identity and homology are depicted in yellow and green, respectively. A numbering based on the tryptase is given above the sequences and a numbering based on chymotrypsinogen (as was used above in this present document) is given below the sequences. The catalytic residues are marked by open triangles and the cysteines forming the disulfide bridges are marked by filled-in triangles. Secondary structure elements in the tryptase are shown diagrammatically (α1-α2 depict α-helices, and β1 to β12 depict β-strands). (The figure was produced using ALSCRIPT (G. J. Barton, Protein Eng. 6 (1993), 37–40)).

FIG. 20 shows the spatial coordinates, obtained from the X-ray structural analysis, of the atoms of human β-tryptase (EC 3.4.21.59) in the Brookhaven PDB format.

EXAMPLES

Example 1

Protein Purification and Crystallization

Tryptase was purified from human lung tissue up to the stage of evident homogeneity using known methods (Schwartz et al., J. Biol. Chem. 256 (1981), 11939–11943; Smith et al., J. Biol. Chem. 259 (1984), 11046 to 11051; Harvima et al., Biochim. Biophys. Acta 957 (1988), 71–80). The protein was inhibited with an excess of 4-amidinophenylpyruvic acid (APPA), concentrated to 4 mg/ml in 8 mM 2-(N-morpholino)ethanesulfonic acid buffer, pH 6.1, 1.7M sodium chloride and equilibrated at 4° C. against 0.2M 3-(N-morpholino)propanesulfonic acid buffer, pH 5.0 and 3M ammonium sulfate. Crystals suitable for the diffraction analysis were obtained by the vapor diffusion of a sitting drop. The crystals exhibit the tetragonal space group P4$_1$, have the cell coordinates a=b=83 Å, c=173 Å, in particular a=b=82.93 Å, c=172.86 Å, and contain one tetramer per asymmetric unit.

Example 2

Crystallographic Methods and Data

Data having a resolution of 2.7 Å were collected on a 300 mm MAR Research image plate detector using monochromatic CuK$_\alpha$ radiation from a rotating anode X-ray generator (Rigaku). The -data were integrated and the intensities reduced using DENZO/SCALEPACK (Otwinowski et al., "DENZO: a film processing for macromolecular crystallography, Yale University, New Haven (1993)), and conversion to structure factor amplitudes was carried out using TRUNCATE (French et al., Acta Cryst. 21 (1978), 517–525). The structure was solved by molecular replacement methods using AMoRe (Navaza, Acty Cryst. A50 (1994), 157–163), while employing a reduced model of swine pancreatic elastase as a search model. Construction of the model was carried out on an SGI-Graphic workstation using TurboFRODO (Roussel et al., TurboFRODO in Silicon Graphics geometry, Silicon Graphics, Mountain View, Calif. (1989)). Crystallographic refinement and calculations of electron density were carried out using X-PLOR and CCP4 (A. T. Brünger, XPLOR Manual, Version 3.1, Yale University, New Haven, Conn. (1992); Collaborative Computational Project No. 4 (1994), Acta Cryst. D50, 760–763). The final model had an R factor of 19.6% (Rfree=28.6%), with an r.m.s. divergence of the targeting data of 0.007 Å and 1.741° for bond lengths and angles, respectively.

Example 3

Amino Acid Sequence

Figure 1:
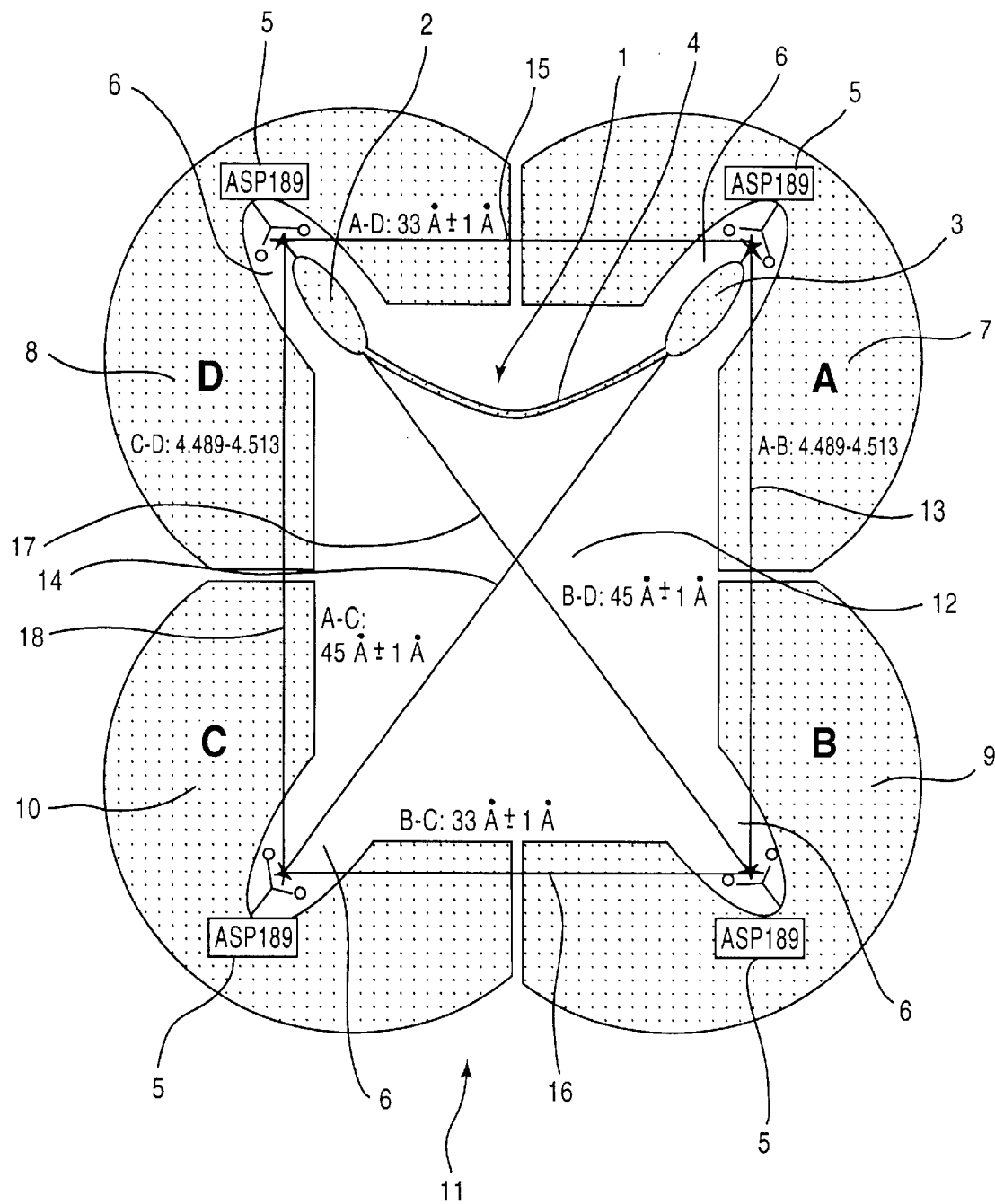
Figure 2A:
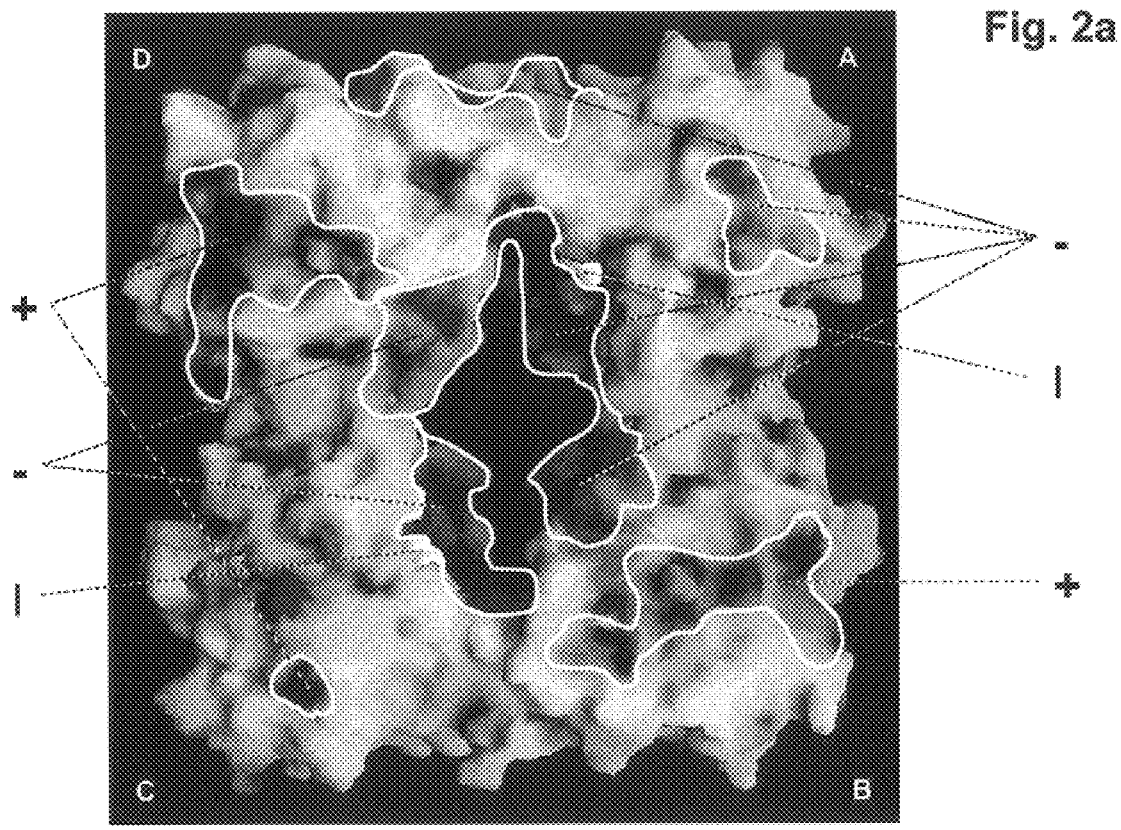
Figure 2B:
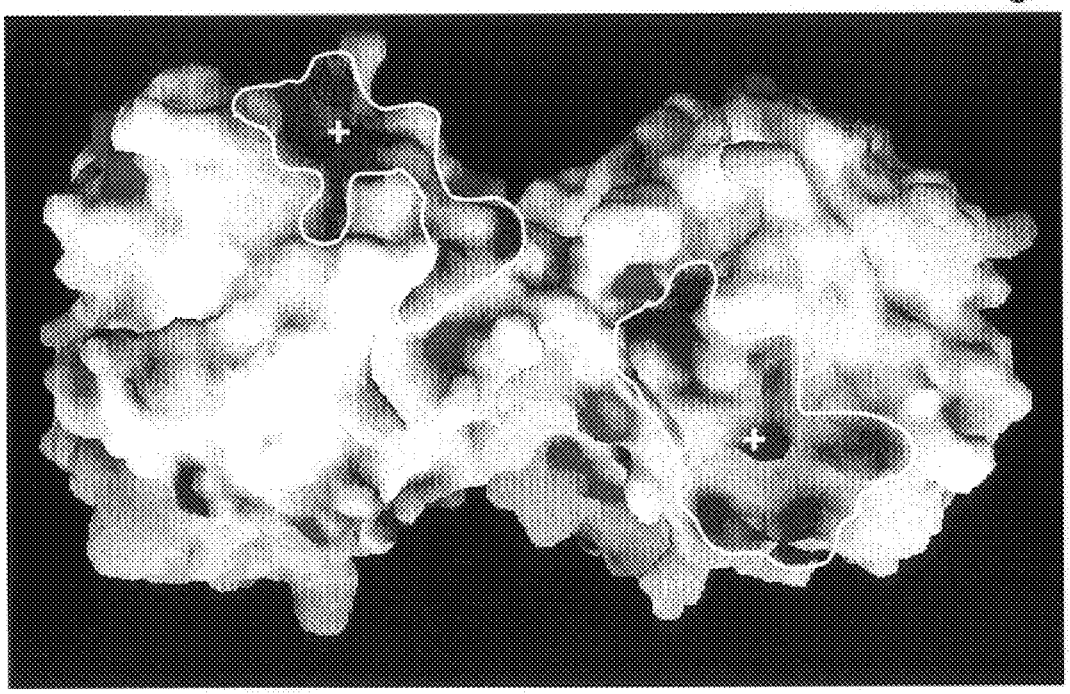
Figure 3:
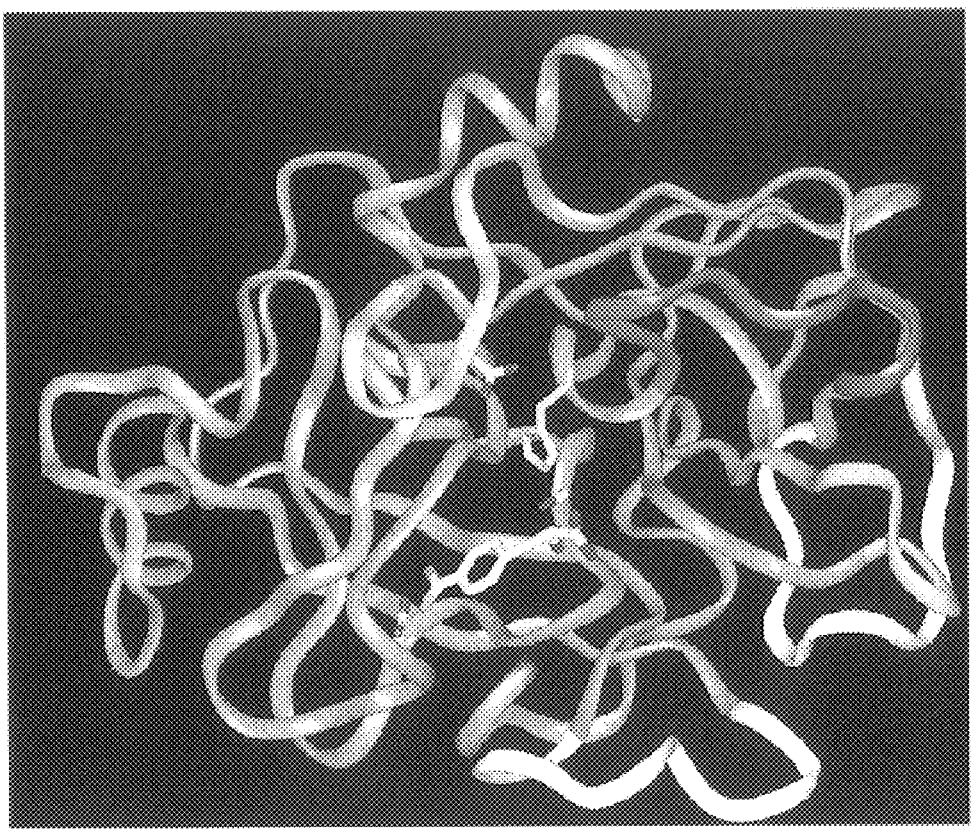
Figure 4:
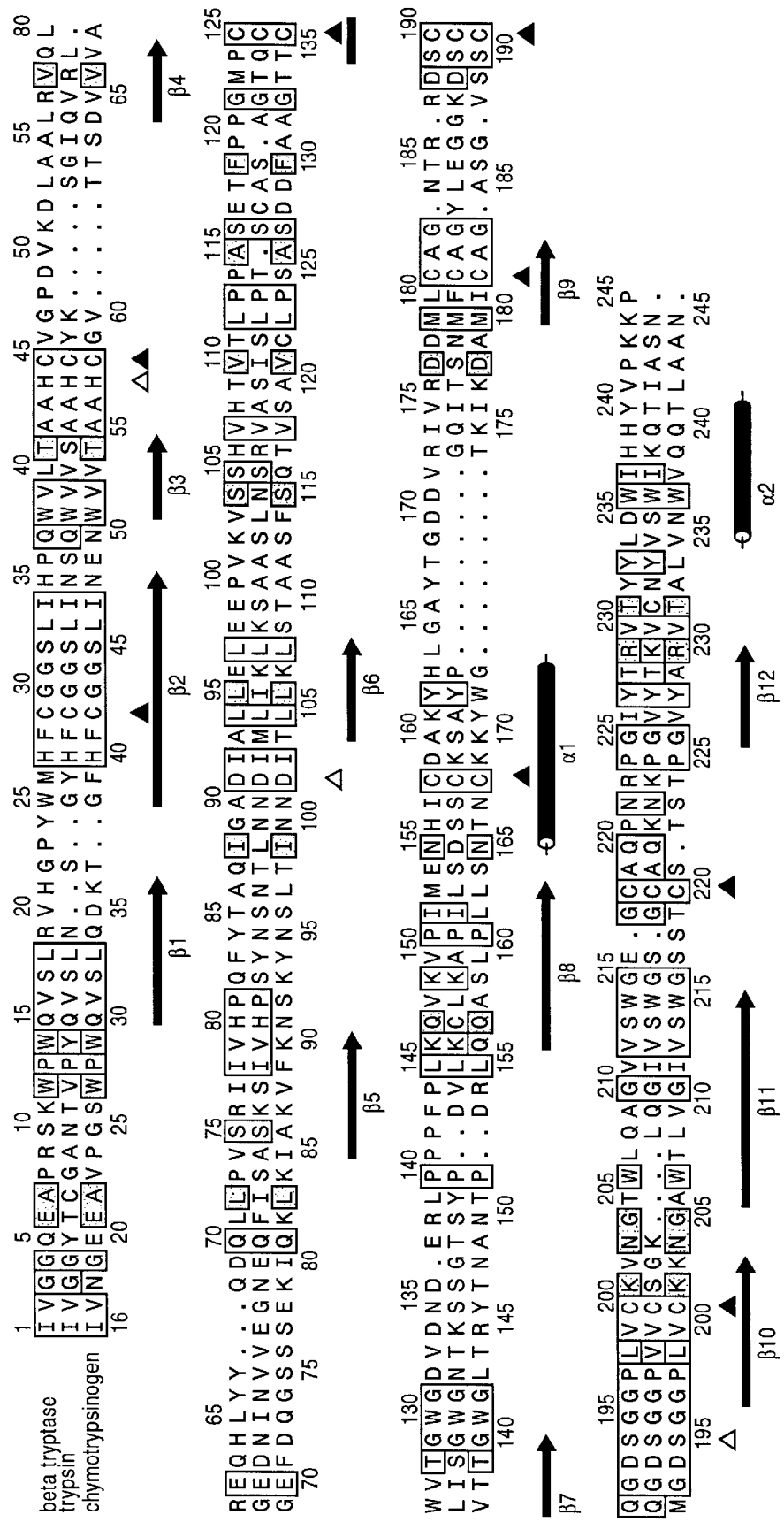
Figure 5A:
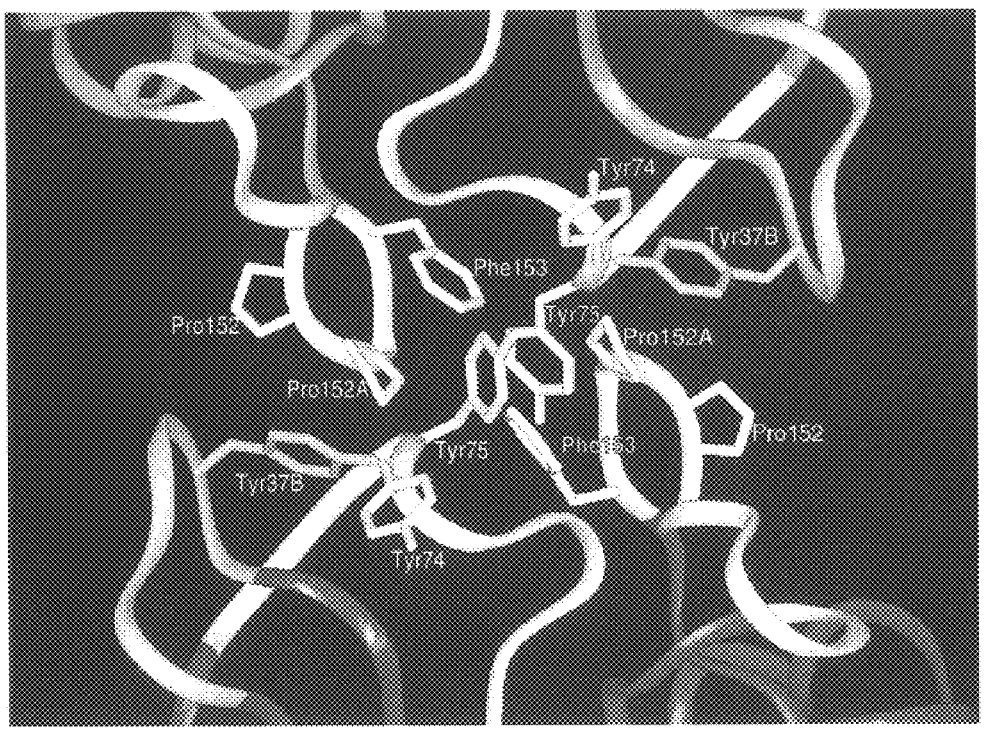
FIG. 5 depicts the contact regions between the A and B monomers (5a) and the A and C monomers (5b), respectively.
Figure 5B:
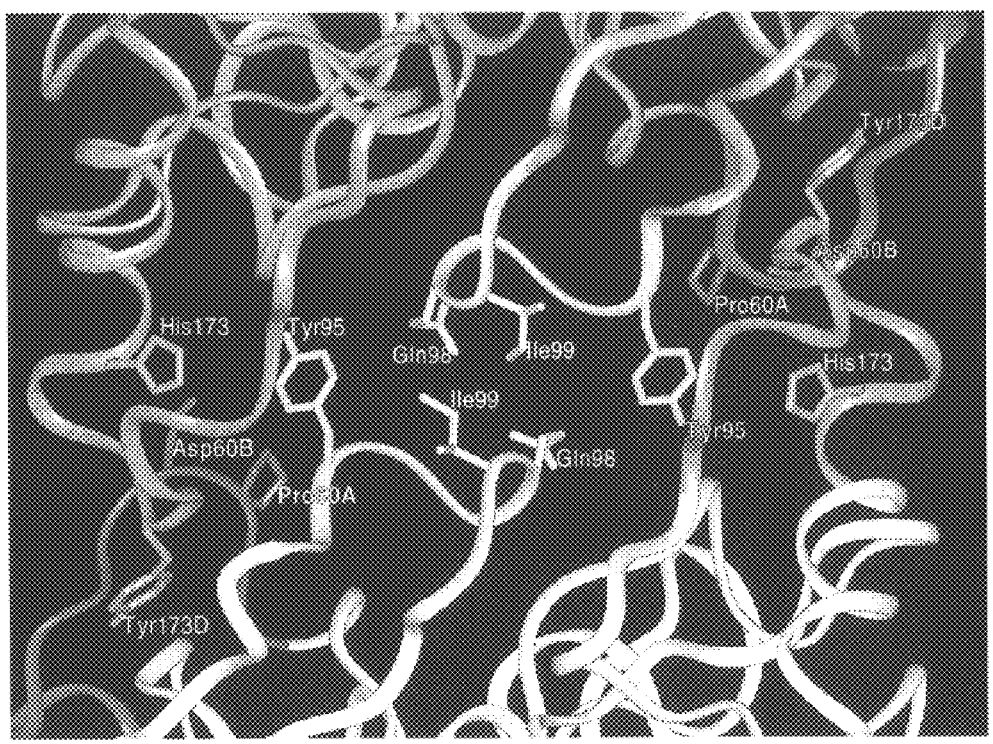
Figure 6:
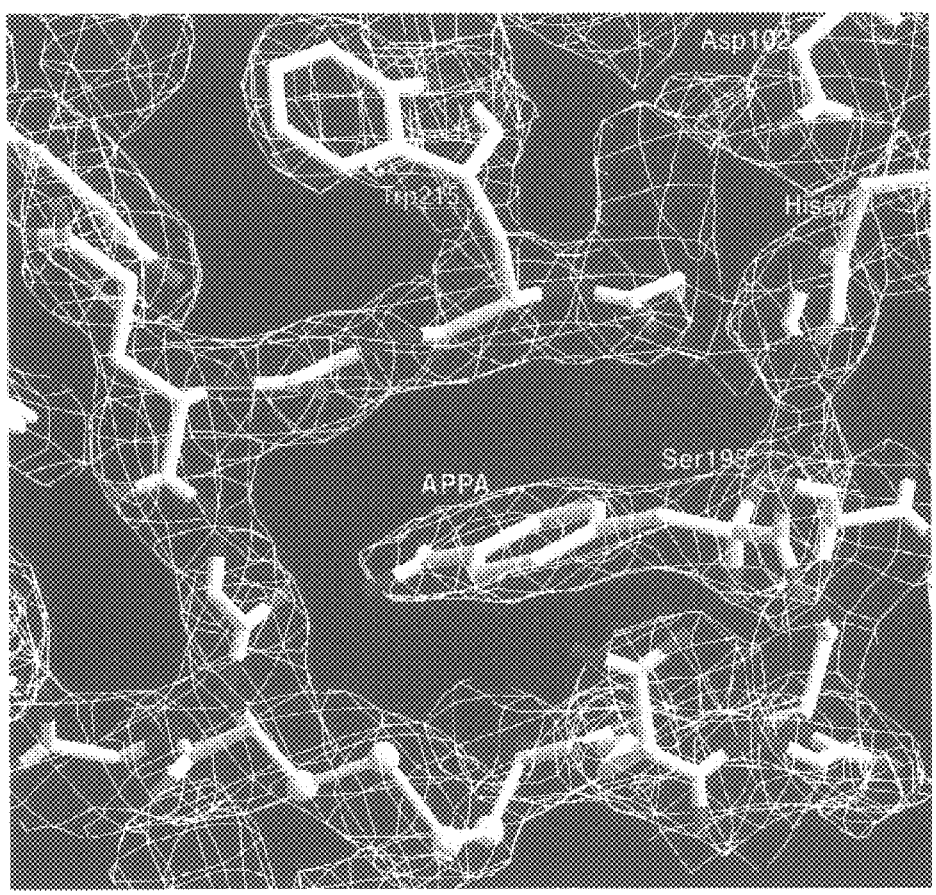
FIG. 6 shows the final 3 Å electron density around the specificity pocket of the APPA-tryptase complex.
Figure 7:
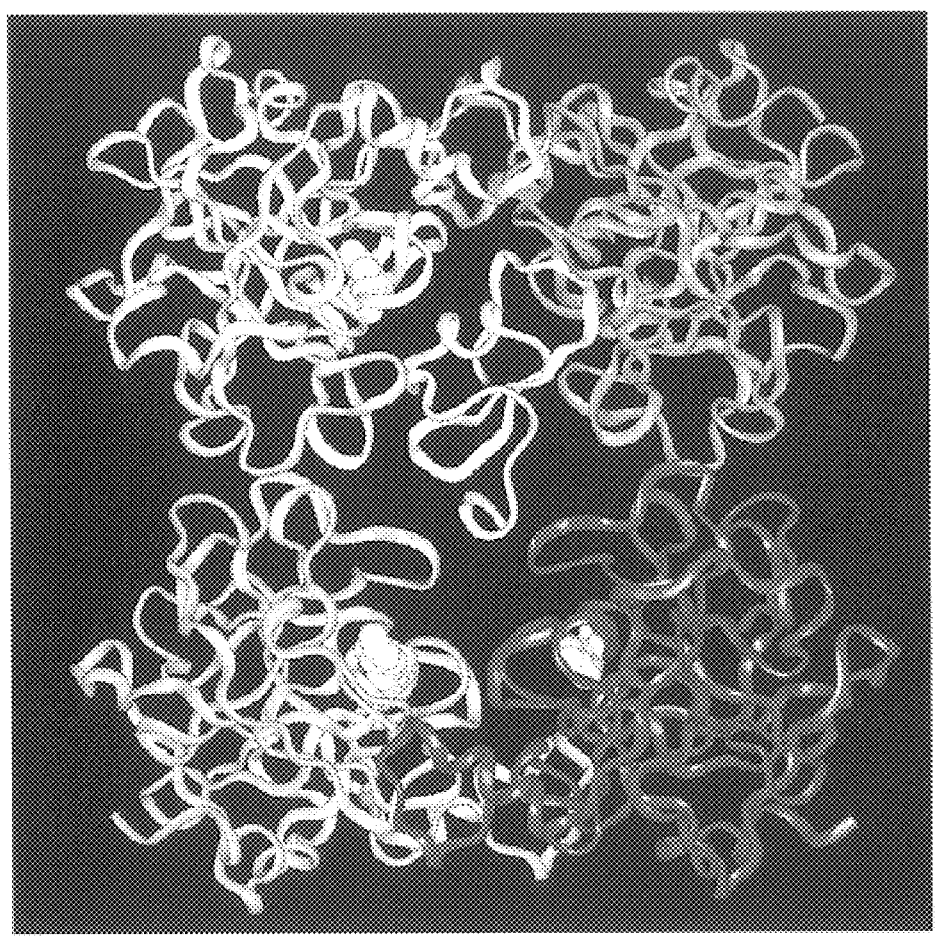
FIG. 7 depicts the experimental structure of the tryptase tetramer, together with an LDTI molecule docked on the monomer.

The amino acid sequence of human β-tryptase (i.e. tryptase II; EC 3.4.21.59) as given in the EMBL/PIR data records (entries M37488/B35863 and M33492/P20231) was used. This sequence was confirmed by cleaving the crystallization material with trypsin and subjecting the resulting fragments to mass spectrometric analysis. The amino acid numbering follows that of chymotrypsinogen (cf. FIG. 4).

Preparation of Bifunctional Tryptase Inhibitors (Examples 4–14)

Example 4

END PRODUCT

Figure 8:
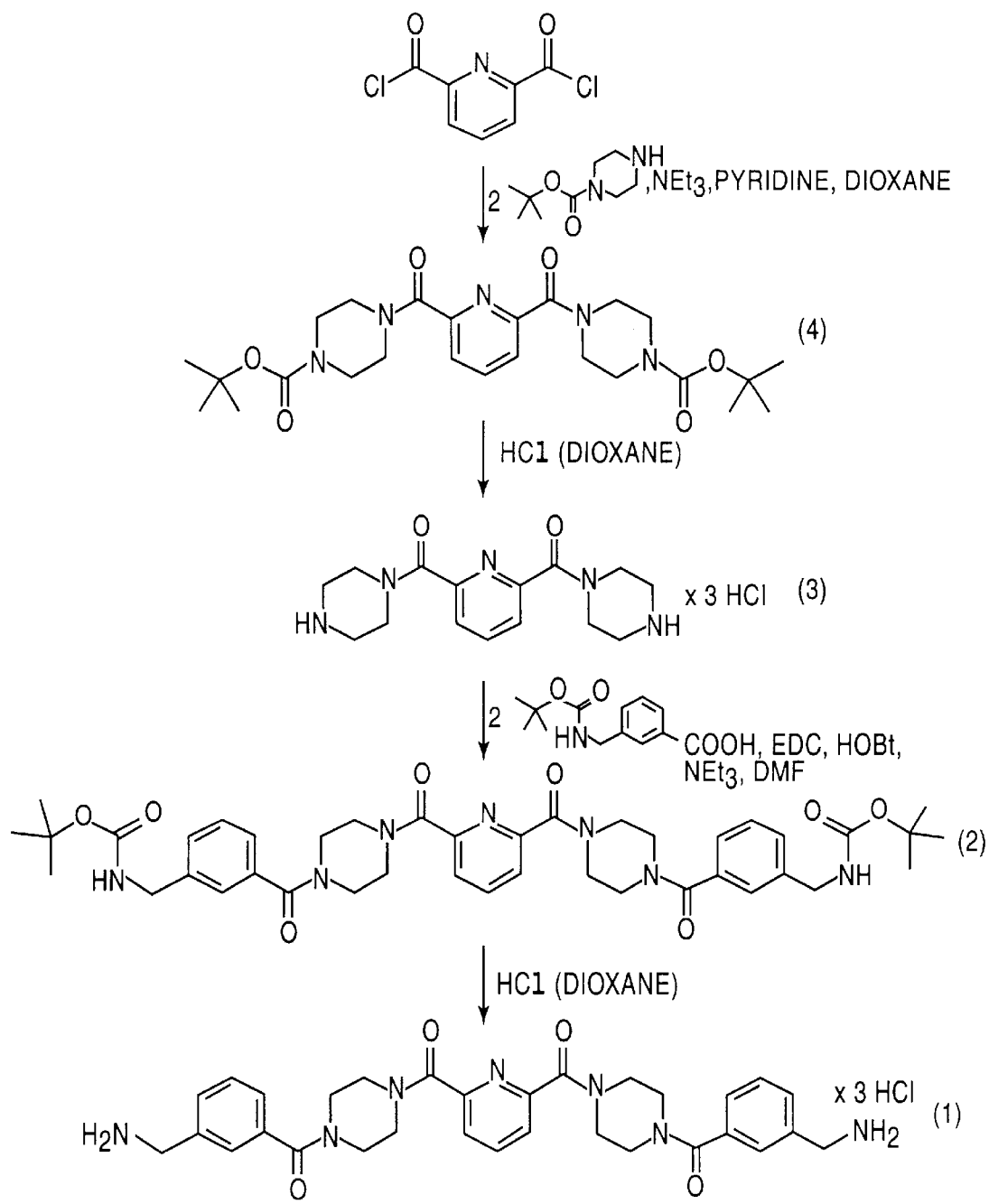
FIGS. 8, 9, 10, 11, 12, 13, 14, 15, 16, 17, 18 and 19 show formula schemes for preparing bifunctional inhibitors according to the invention.

Pyridine-2,6-dicarbobis[4-(3-aminomethylbenzoyl)-1-piperazide] (1) (cf. FIG. 8)

1.3 ml of a 4.8 N solution of HCl in dioxane (6.2 mmol) are added dropwise to a solution of 600 mg (780 μmol) of pyridine-2,6-dicarbobis[4-(3-butyloxycarbonylaminomethylbenzoyl)-1-piperazide] in 7 ml of dioxane. 10 ml of methanol are added to the thick suspension and the mixture is stirred for 2.5 hours. It is then concentrated and the residue is taken up in 25 ml of water and the solution is adjusted to pH=11 (NaOH). The solution is then extracted with 3×20 ml of dichloromethane, and the combined organic phases are dried over MgSO$_4$ and concentrated. The product is dissolved in 2 ml of dioxane, with 0.5 ml of a 4.8 N solution of HCl in dioxane (2.4 mmol) then being added; the suspension is diluted with 15 ml of diethyl ether. The title compound is isolated as hydrochloride having a m.p. of >260° C.

STARTING COMPOUNDS

Pyridine-2,6-dicarbobis[4-(3-tert-butyloxycarbonylaminomethylbenzoyl)-1-piperazide] (2)

1.36 ml (9.7 mmol) of triethylamine, 610 mg (2.42 mmol) of 3-tert-butyloxycarbonylaminomethylbenzoic acid, 330 mg (2.42 mmol) of 1-hydroxybenzotriazole and 460 mg (2.42 mmol) of N-(3-dimethylaminopropyl)-N'-ethyl-carbodiimide hydrochloride (EDCxHCl) are added, one after the other, to a suspension of 500 mg (1.21 mmol) of pyridine-2,6-dicarbobispiperazide trihydrochloride in 15 ml of DMF. After 75 min., the reaction mixture is extensively concentrated, after which 20 ml of water are added to the residue and the resulting solution is adjusted to pH=11 (NaOH). It is then extracted with 3×20 ml of dichloromethane, after which the combined organic phases are dried over MgSO$_4$ and concentrated, and the crude product is chromatographed through silica gel (ethyl acetate/methanol=10:1). The eluate is concentrated and the residue is stirred thoroughly in diethyl ether. 700 mg (75%) of the title compound having a m.p. of 195° C. (frothing at 110° C.) are obtained.

Pyridine-2,6-dicarbobispiperazide (3)

6.8 ml of a 4.8 N solution of HCl in dioxane (16.2 mmol) are added dropwise to a suspension of 2.05 g (4.07 mmol) of pyridine-2,6-dicarbobis-4-tert-butyloxycarbonylpiperazide in 20 ml of dioxane. The suspension is diluted with 10 ml of methanol and the mixture is stirred at room temperature overnight. The solvent is extensively concentrated, after which the suspension is thoroughly stirred with diethyl ether and filtered under a protective gas atmosphere. 1.7 g (100%) of the trihydrochloride of the title compound are obtained. m.p.>260° C.

Pyridine-2,6-dicarbobis-4-tert-butyloxycarbonyl-piperazide (4)

1.0 g (5.0 mmol) of 2,6-pyridinedicarbonyl dichloride in 10 ml of dioxane is added dropwise to a solution of 1.88 g (10.1 mmol) of tert-butyl piperazine-N-carboxylate in 0.82 ml (10.1 mmol) of pyridine, 3.5 ml (25.2 mmol) of triethylamine and 10 ml of dioxane. The mixture is stirred at room temperature overnight, after which the precipitate is filtered off and the mother liquor is concentrated to dryness. The residue is extracted with 3×30 ml of dichloromethane from 30 ml of water. The organic phase, which has been dried over MgSO$_4$, is concentrated and the residue is crystallized from diethyl ether. 2.16 g (90%) of the title compound having a m.p. of 183–186° C. are obtained.

Example 5

END PRODUCTS

Figure 9:
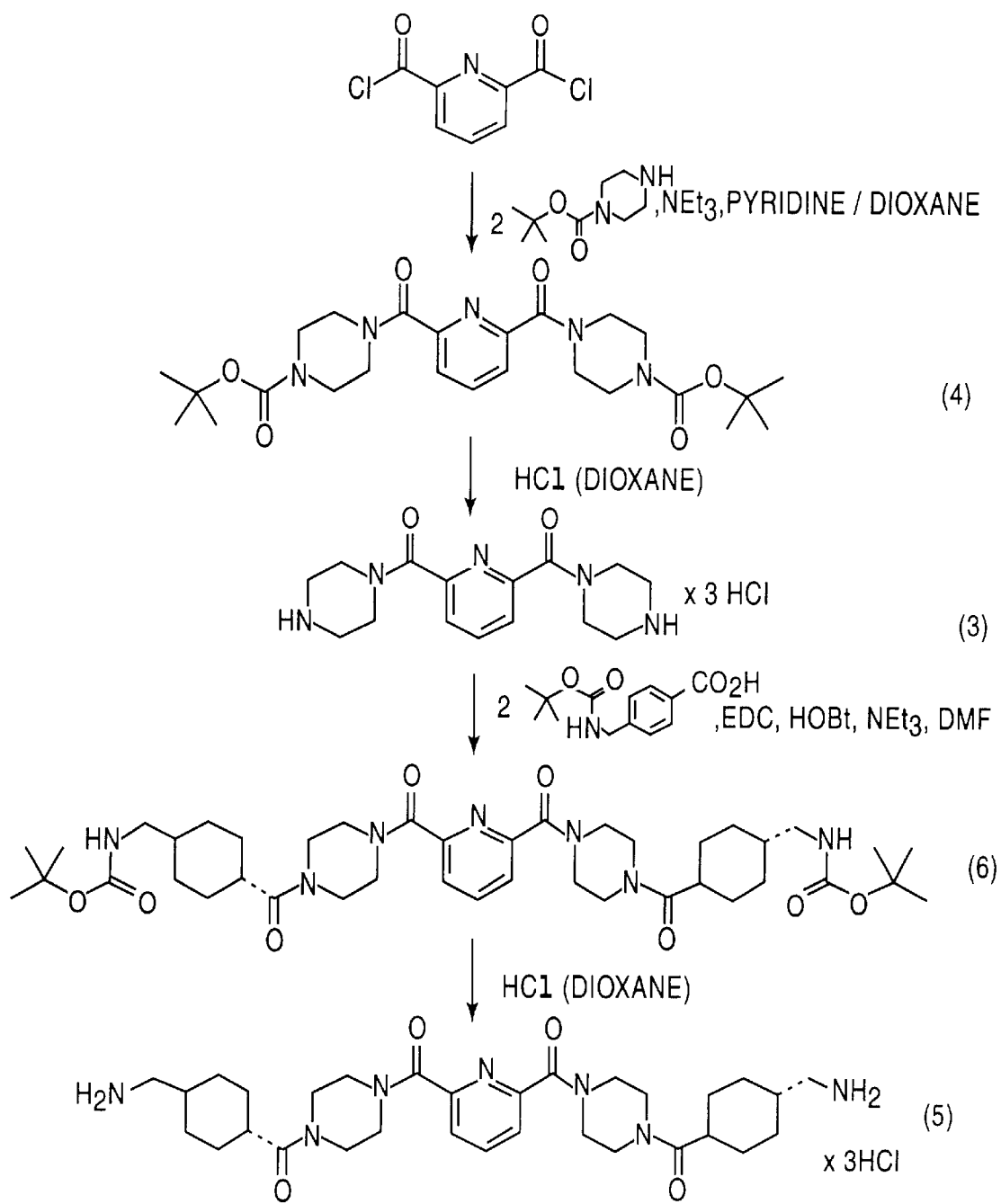

Pyridine-2,6-dicarbobis[4-(trans-4-aminomethylcyclohexanoyl)-1-piperazide] (5) (cf. FIG. 9)

1.06 ml of a 4.6 N solution of HCl in dioxane (5.1 mmol) are added dropwise to a solution of 500 mg (640 μmol) of pyridine-2,6-dicarbobis[4-(trans-4-tert-butyloxycarbonylaminomethylcyclohexylcarbonyl)-1-piperazide] in 10 ml of dioxane. 20 ml of methanol are added to the thick suspension and the whole is stirred at 40° C. for 4 hours. The mixture is concentrated; the residue is then coevaporated with 2×20 ml of toluene and crystallized from diethyl ether. The title compound is isolated as the dihydrochloride having a m.p. of 170° C. (frothing).

Figure 10:
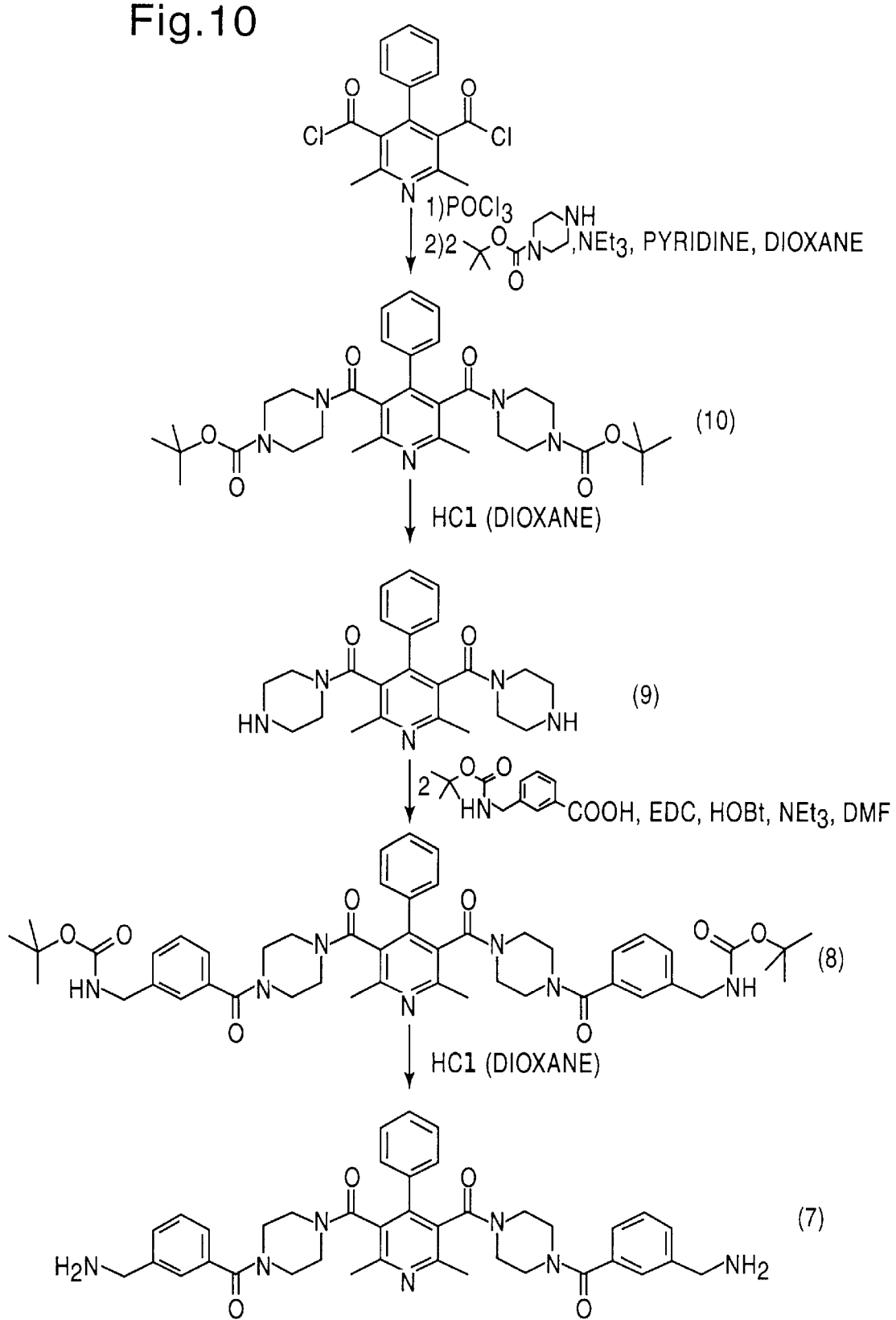

2,6-Dimethyl-4-phenylpyridine-3,5-dicarbobis[4-(3-aminomethylbenzoyl)-1-piperazide] (7) (cf. FIG. 10)

522 μl of a 4.6 N solution of HCl in dioxane (2.4 mmol) are added to a solution of 350 mg (0.4 mmol) of 2,6-dimethyl-4-phenylpyridine-3,5-dicarbobis[4-(3-tert-butyloxycarbonylaminomethylbenzoyl)-1-piperazide] in 5 ml of dioxane and 5 ml of methanol. After the mixture has been stirred overnight at room temperature, a further 200 μl (0.9 mmol) of HCl in dioxane are added and the reaction mixture is heated at 40° C. for 5 hours. The mixture is concentrated, and the residue is stirred up with 5 ml of dioxane and 2 ml of diethyl ether, and the title compound is isolated as dihydrochloride having a m.p. of 250° C. (sintering at 223° C.).

STARTING COMPOUNDS

Pyridine-2,6-dicarbobis[4-(trans-4-tert-butyloxycarbonylaminomethylcyclohexylcarbonyl)-1-piperazide] (6)

1.36 ml (9.7 mmol) of triethylamine, 620 mg (2.42 mmol) of trans-4-tert-butyloxycarbonylaminomethylcyclohexanecarboxylic acid, 330 mg (2.42 mmol) of 1-hydroxybenzotriazole and 460 mg (2.42 mmol) of N-(3-dimethylaminopropyl)-N'-ethylcarbodiimide hydrochloride (EDC×HCl) are added, one after the other, to a suspension of 500 mg (1.21 mmol) of pyridine-2,6-dicarbobispiperazide trihydrochloride in 15 ml of DMF. After 45 min., the reaction mixture is extensively concentrated, after which 20 ml of water are added to the residue and the resulting solution is adjusted to pH=12 (NaOH). It is then extracted with 3×20 ml of dichloromethane, after which the combined organic phases are dried over MgSO$_4$ and concentrated, and the crude product is chromatographed through silica gel (ethyl acetate/methanol/ammonia=10:1:0.5). The eluate is concentrated and the residue is stirred thoroughly in diisopropyl ether. 620 mg (65%) of the title compound, having a m.p. of 200–202° C., are obtained.

2,6-Dimethyl-4-phenylpyridine-3,5-dicarbobis[4-(3-tert-butyloxycarbonylaminomethylbenzoyl)-1-piperazide] (8)

500 μl (4.2 mmol) of triethylamine, 280 mg (1.1 mmol) of 3-tert-butyloxycarbonylaminomethylbenzoic acid, 280 mg (1.1 mmol) of 1-hydroxybenzotriazole and 280 mg (2.1 mmol) of N-(3-dimethylaminopropyl)-N'-ethylcarbodiimide hydrochloride (EDC×HCl) are added, one after the other, to a suspension of 220 mg (0.53 mmol) of 2,6-dimethyl-4-phenylpyridine-3,5-dicarbobis-piperazide in 10 ml of DMF. After 4 hours, the reaction mixture is extensively concentrated after which 30 ml of water are added to the residue and the resulting solution is adjusted to pH=12 (NaOH). It is then extracted with a total of 70 ml of dichloromethane, after which the combined organic phases are dried over MgSO$_4$ and concentrated, and the crude product is chromatographed through silica gel (ethyl acetate/methanol=10:1). The eluate is concentrated and the residue is stirred thoroughly in diisopropyl ether. 446 mg (96%) of the title compound, having a m.p. of 113° C., are obtained.

2,6-Dimethyl-4-phenylpyridine-3,5-dicarbobispiperazide (9)

12.6 ml of a 4.6 N solution of HCl in dioxane (57.6 mmol) are added dropwise to a suspension of 5.87 g (9.6 mmol) of 2,6-dimethyl-4-phenylpyridine-3,5-dicarbobis-4-tert-butyloxycarbonylpiperazide in 20 ml of dioxane and 10 ml of methanol. The mixture is stirred at room temperature for 5 hours. The solvent is concentrated and the residue is thoroughly stirred with 30 ml of diethyl ether and 70 ml of methanol. 4.35 g (94%) of the dihydrochloride of the title compound, having a m.p. of >250° C., are obtained.

2,6-Dimethyl-4-phenylpyridine-3,5-dicarbobis-4-tert-butyloxycarbonylpiperazide (10)

13.0 g (mmol) of dipotassium 2,6-dimethyl-4-phenyl-pyridine-3,5-dicarboxylate are boiled, at 100° C. for 5 hours and under a nitrogen atmosphere, in 80 ml of phosphorus oxychloride. The phosphorus oxychloride is distilled off in vacuo and the residue is coevaporated with 3×50 ml of toluene. A suspension of a crude acid chloride in 200 ml of dioxane is added dropwise, while controlling the temperature (<30° C.), to a solution of 12.8 g (66 mmol) of tert-butyl piperazine-N-carboxylate, 5.3 ml (66 mmol) of pyridine and 46 ml (450 mmol) of triethylamine in 100 ml of dioxane. After one hour, the inorganic salts are filtered off and the filtrate is concentrated. The residue is extracted from 100 ml of water using 3×70 ml of ethyl acetate. The combined organic phases, which have been dried over MgSO$_4$, are concentrated and the residue is chromatographed through silica gel (ethyl acetate/methanol=10:1). 7.13 g (35%) of the title compound are obtained as a yellowish oil.

Example 6

END PRODUCT

Figure 11:
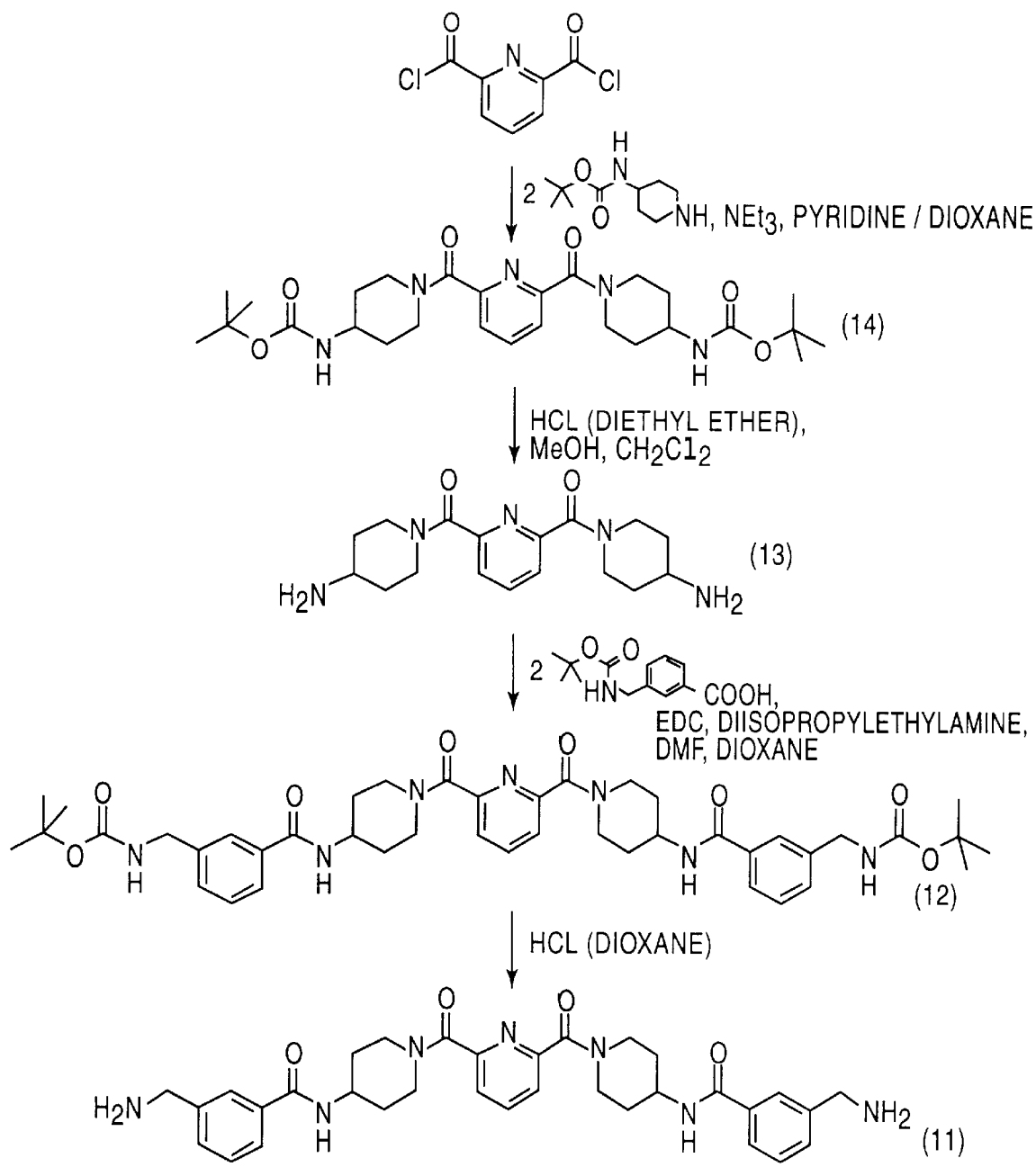

Pyridine-2,6-dicarbobis[4-(3-aminomethylbenzoylamino)-1-piperidide] (11) (cf. FIG. 11)

275 μl of a 4 N solution of HCl in dioxane (1.1 mmol) are added dropwise to a solution of 220 mg (275 vmol) of pyridine-2,6-dicarbobis[4-(3-tert-butyloxycarbonyl-aminomethylbenzoylamino)-1-piperidide] in 5 ml of dioxane. 3 ml of methanol are added to the thick suspension and the whole is stirred for 12 hours. The mixture is concentrated and the residue is coevaporated with 2×20 ml of toluene and crystallized. 130 mg of the title compound, having a m.p. of 230° C. (frothing), are obtained.

STARTING COMPOUNDS

Pyridine-2,6-dicarbobis[4-(3-tert-butyloxycarbonylaminomethylbenzoylamino)-1-piperidide] (12)

342 mg (1.36 mmol) of 3-tert-butyloxycarbonylaminomethylbenzoic acid, 240 μl (1.36 mmol) of Hünig's base, 30 mg of diaminopyridine and 260 mg (1.36 mmol) of N-(3-dimethylaminopropyl)-N'-ethylcarbodiimide hydro-chloride (EDC×HCl) are added, one after the other, to a suspension of 250 mg (0.62 mmol) of pyridine-2,6-dicarbobis(4-amino-1-piperidide) dihydrochloride in 2.5 ml of DMF and 2.5 ml of dioxane. After having been stirred at room temperature for 12 hours, the reaction mixture is concentrated, after which 10 ml of water are added to the residue and the resulting solution is adjusted to pH=3 (0.1 N HCl). It is then extracted with 3×20 ml of dichloromethane, after which the combined organic phases are dried over $MgSO_4$ and concentrated, and the crude product is chromatographed through silica gel (dichloromethane/methanol=19:1). The product-containing eluate is concentrated and the residue is thoroughly stirred in diethyl ether. 280 mg (57%) of the title compound, having a m.p. of 140° C. (frothing, sintering from 120° C. onward) are obtained.

Pyridine-2,6-dicarbobis(4-amino-1-piperidide) (13)

12 ml of a 6 N solution of HCl in diethyl ether (72 mmol) are added dropwise to a solution of 2.0 g (3.76 mmol) of pyridine-2,6-dicarbobis(4-tert-butyl-oxycarbonylamino-1-piperidide) in 10 ml of diethyl ether, 30 ml of methanol and 20 ml of dichloromethane, and the reaction mixture is heated at 40° C. for 2 hours. The solvent is concentrated and the residue is thoroughly stirred with diethyl ether and filtered off under a protective gas atmosphere. 1.52 g (100%) of the dihydrochloride of the title compound are obtained. m.p. 130° C.

Pyridine-2,6-dicarbobis(4-tert-butyloxycarbonylamino-1-piperidide) (14)

850 mg (4.05 mmol) of 2,6-pyridinedicarbonyl dichloride in 10 ml of dioxane are added dropwise to a suspension of 1.67 g (8.08 mmol) of tert-butyl piperidine-N-carboxylate in 0.65 ml (8.08 mmol) of pyridine, 2.8 ml (20 mmol) of triethylamine and 10 ml of dioxane. The mixture is stirred overnight at room temperature and then concentrated. 30 ml of water are added to the residue and the resulting solution is made basic (pH=11) with NaOH. It is then extracted with 3×30 ml of dichloromethane, after which the combined organic phases are dried over $MgSO_4$ and concentrated, and the residue is crystallized from diethyl ether. 2.12 g (99%) of the title compound, having a m.p. of 90° C., are obtained.

Example 7

END PRODUCT

Figure 12:
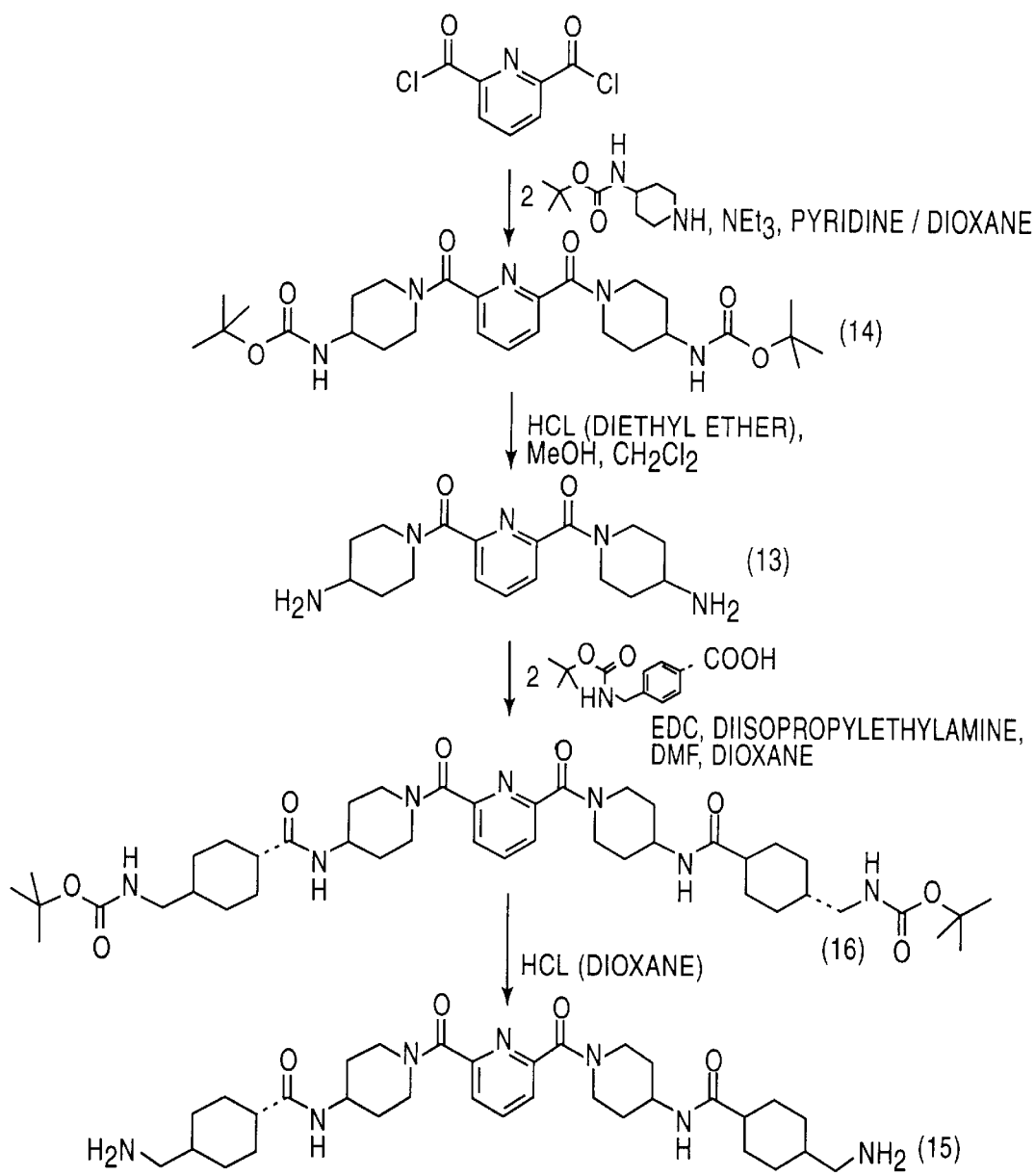
Figure 13:
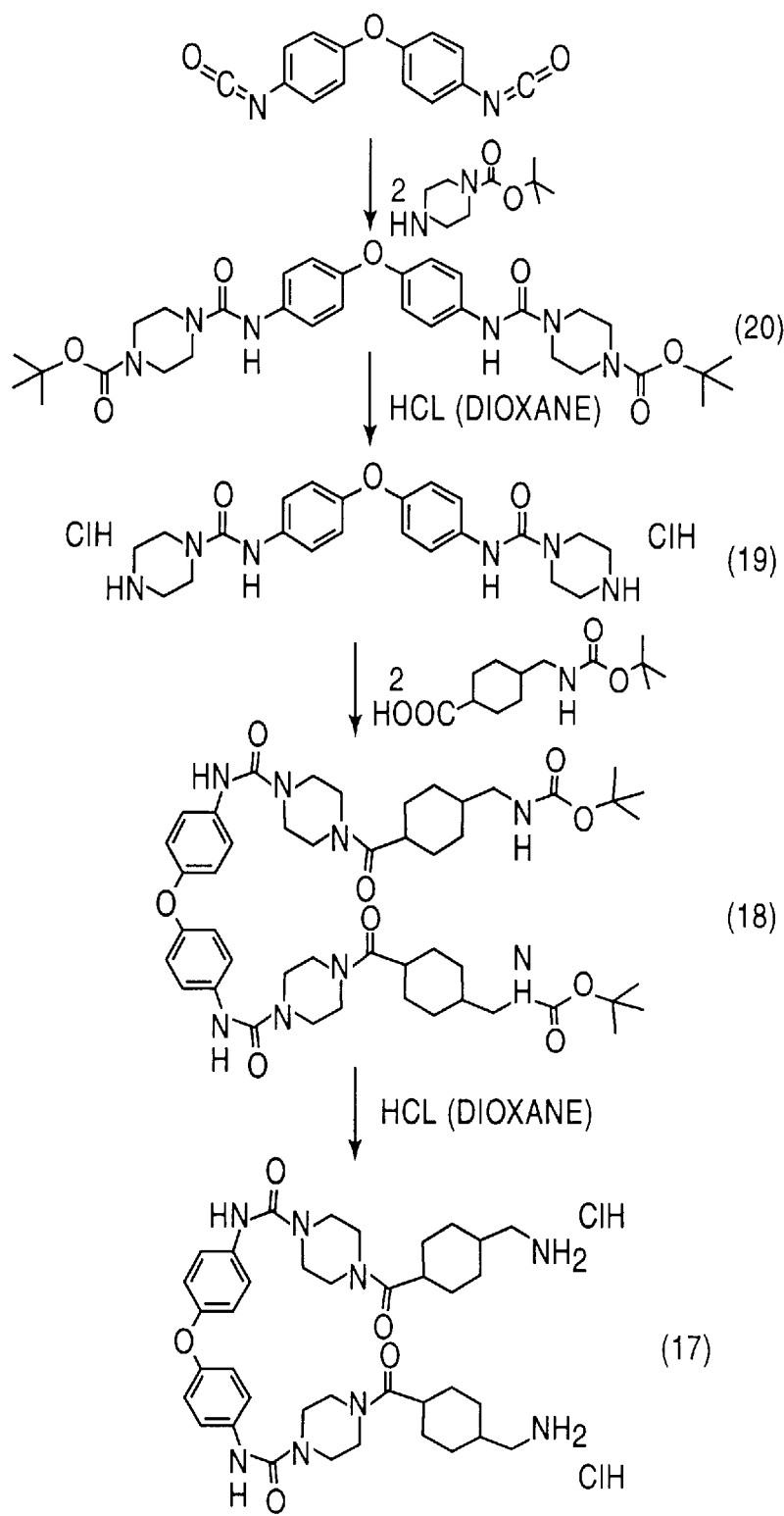

Pyridine-2,6-dicarbobis[4-(4-aminomethylcyclohexylcarbonylamino)-1-piperidide] (15) (cf. FIG. 12)

500 μl of a 4 N solution of HCl in dioxane (2.0 mmol) are added dropwise to a suspension of 160 mg (197 vmol) of pyridine-2,6-dicarbobis[4-(4-tert-butyloxycarbonylaminomethylcyclohexylcarbonylamino)-1-piperidide in 10 ml of dioxane and 2 ml of methanol, and the mixture is stirred at room temperature for 12 hours. It is then concentrated and the residue is coevaporated twice with 50 ml of diethyl ether; the crude product is then thoroughly stirred in diethyl ether. 100 mg of the title compound, having a m.p. of>250° C., are obtained.

STARTING COMPOUNDS

Pyridine-2,6-dicarbobis[4-(4-tert-butyloxycarbonylaminomethylcyclohexylcarbonylamino)-1-piperidide] (16)

350 mg (1.36 mmol) of trans-3-tert-butyloxycarbonyl-aminomethylcyclohexylcarboxylic acid, 240 μl (1.36 mmol) of Hünig's base, 30 mg of diaminopyridine and 260 mg (1.36 mmol) of N-(3-dimethylaminopropyl)-N'-ethylcarbodiimide hydrochloride (EDC×HCl) are added, one after the other, to a suspension of 250 mg (0.62 mmol) of pyridine-2,6-dicarbobis(4-amino-1-piperidide) dihydrochloride in 2.5 ml of DMF and 2.5 ml of dioxane. After having been stirred at room temperature for 12 hours, the reaction mixture is concentrated, after which 10 ml of water are added to the residue and the resulting solution is adjusted to pH=3 (0.1 N HCl). It is then extracted with 3×20 ml of dichloromethane, after which the combined organic phases are dried over $MgSO_4$ and concentrated, and the crude product is chromatographed through silica gel (dichloromethane/methanol=19:1). The product-containing eluate is concentrated and the residue is thoroughly stirred in diethyl ether. 230 mg (46%) of the title compound, having a m.p. of >250° C., are obtained.

Example 8

END PRODUCT bis{4-[4-(4-Aminomethyl)cyclohexanoylpiperazin-1-yl-]-carbonyl}-4,4'-diaminodiphenyl Ether Dihydrochloride (17) (cf. FIG., 13)

Bis{4-[4-(4-tert-butoxycarbonylaminomethyl)cyclo-hexanoylpiperazin-1-yl]carbonyl}-4,4'-diaminodiphenyl ether (0.18 g; 0.2 mmol) is suspended in 4.8 M HCl in dioxane (5 ml). The suspension is stirred at 40–45° C. for 24 hours. After the addition of diethyl ether (25 ml), the mixture is cooled in an ice bath. The product, which has precipitated out, is filtered off with suction, washed several times with diethyl ether and dried in vacuo. Yield: 0.12 g, white amorphous solid.

MS (ESI): 703.4 (100) MH$^+$

STARTING COMPOUNDS bis{4-[4-(4-tert-Butoxycarbonylaminomethyl)cyclo-hexanoylpiperazin-1-yl]carbonyl}-4,4'-diaminodiphenyl Ether (18)

4,4'-Bis(1-piperazinylcarbamoyl)diphenyl ether dihydro-chloride (0.25 g; 0.5 mmol), Boc-tranexamic acid (0.28 g; 1.1 mmol), N-ethyldiisopropylamine (0.2 ml; 1.1 mmol) and 4-dimethylaminopyridine (5 mg) are stirred, at room temperature for 15 minutes, in dimethyl formamide (2.5 ml) and dichloromethane-(2.5 ml). After the addition of N-(3-dimethylamino-propyl)-N'-ethylcarbodiimide hydrochloride (0.21 g; 1.1 mmol), the reaction mixture is stirred at 40° C. for 24 hours. The solvent is stripped off completely in vacuo. The residue is chromatographed on silica gel (dichloromethane:methanol—9:1). The product fraction is collected and the solvent is stripped off completely in vacuo. Yield: 0.18 g, white amorphous solid.

MS (ESI): 903.1 (100) MH$^+$ 4,4'-bis(1-Piperazinylcarbamoyl)diphenyl Ether Dihydro-chloride (19)

4,4'-Bis(4-(tert-butyloxycarbonyl)-1-piperazinyl-carbamoyl]diphenyl ether (6.4 g; 10.2 mmol) is suspended in 4.8 M HCl in dioxane (50 ml). The suspension is stirred at 40–45° C. for 22 hours. After the addition of diethyl ether (100 ml), the mixture is cooled in an ice bath. The product, which has precipitated out, is filtered off with suction, washed several times with diethyl ether and dried in vacuo. Yield: 4.65 g, white amorphous solid.

MS (APCI): 425.0 (100) MH+

4,4'-bis[4-(tert-Butyloxycarbonyl)-1-piperazinyl-carbamoyl]diphenyl Ether (20)

A solution of 4,4'-oxybis(phenyl isocyanate) (2.52 g, 10 mmol) in dichloromethane (25 ml) is added dropwise, at room temperature, to a stirred solution of 1-tert-butoxycarbonylpiperazine (4.10 g; 22 mmol) in dichloromethane (50 ml). After the addition has come to an end, the mixture is stirred at room temperature for a further 3 hours. The product, which has precipitated out, is filtered off with suction, washed several times with hexane and dried in vacuo. Yield: 6.20 g of a white amorphous solid.

MS (EI): 625.5 (12) MH$^+$; 271.2 (26); 118.2 (42); 187.1 (100)

Example 9

END PRODUCT

Figure 14:
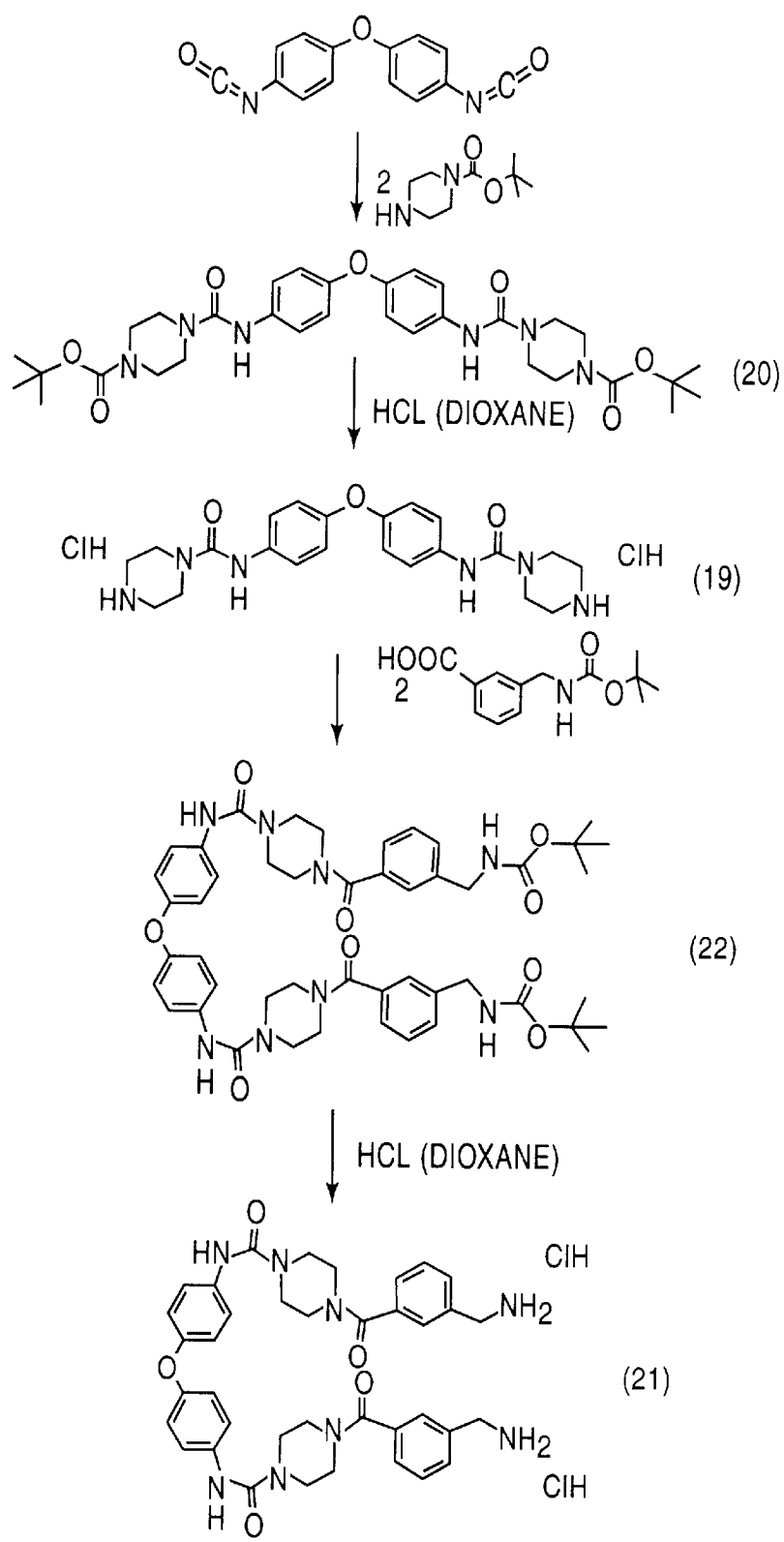

Bis{4-[4-(3-Aminomethyl)benzoylpiperazin-1-yl]-carbonyl}-4,4'-diaminodiphenyl Ether Dihydrochloride (21) (cf. FIG. 14)

Bis{4-[4-(3-tert-butoxycarbonylaminomethyl)benzoyl-piperazin-1-yl]carbonyl}-4,4'-diaminodiphenyl ether (0.31 g; 0.35 mmol) is stirred, at 40–45° C. for 24 hours, in 4.8 M HCl in dioxane (5 ml). After the addition of diethyl ether (25 ml), the mixture is cooled in an ice bath. The product, which has precipitated out, is filtered off with suction, washed several times with diethyl ether and dried in vacuo. Yield: 0.19 g, white amorphous solid.

MS (ESI): 691.2 (100) M$^+$

STARTING COMPOUNDS bis(4-[4-(3-tert-Butoxycarbonylaminomethyl)benzoyl-piperazin-1-yl]carbonyl)-4,4'-diaminodiphenyl Ether (22)

4,4'-Bis(1-piperazinylcarbamoyl)diphenyl ether dihydrochloride (0.25 g; 0.5 mmol), 3-(tert-butoxycarbonyl-aminomethyl)benzoic acid (0.28 g; 1.1 mmol), N-ethyldiisopropylamine (0.2 ml; 1.1 mmol) and 4-dimethylaminopyridine (30 mg) are stirred, at room temperature for 15 minutes, in dimethyl formamide (2.5 ml) and dioxane (2.5 ml). After the addition of N-(3-dimethylaminopropyl)-N'-ethylcarbodiimide hydrochloride (0.21 g; 1.1 mmol), the reaction mixture is stirred at room temperature for 24 hours. The solvent is stripped off completely in vacuo. The residue is chromatographed on silica gel (dichloromethane:methanol—9:1). The product fraction is collected and the solvent is stripped off completely in vacuo. Yield: 0.32 g, viscous oil.

MS (ESI): 890.8, M$^+$; 791.2, MH-Boc$^+$

Example 10

Figure 15:
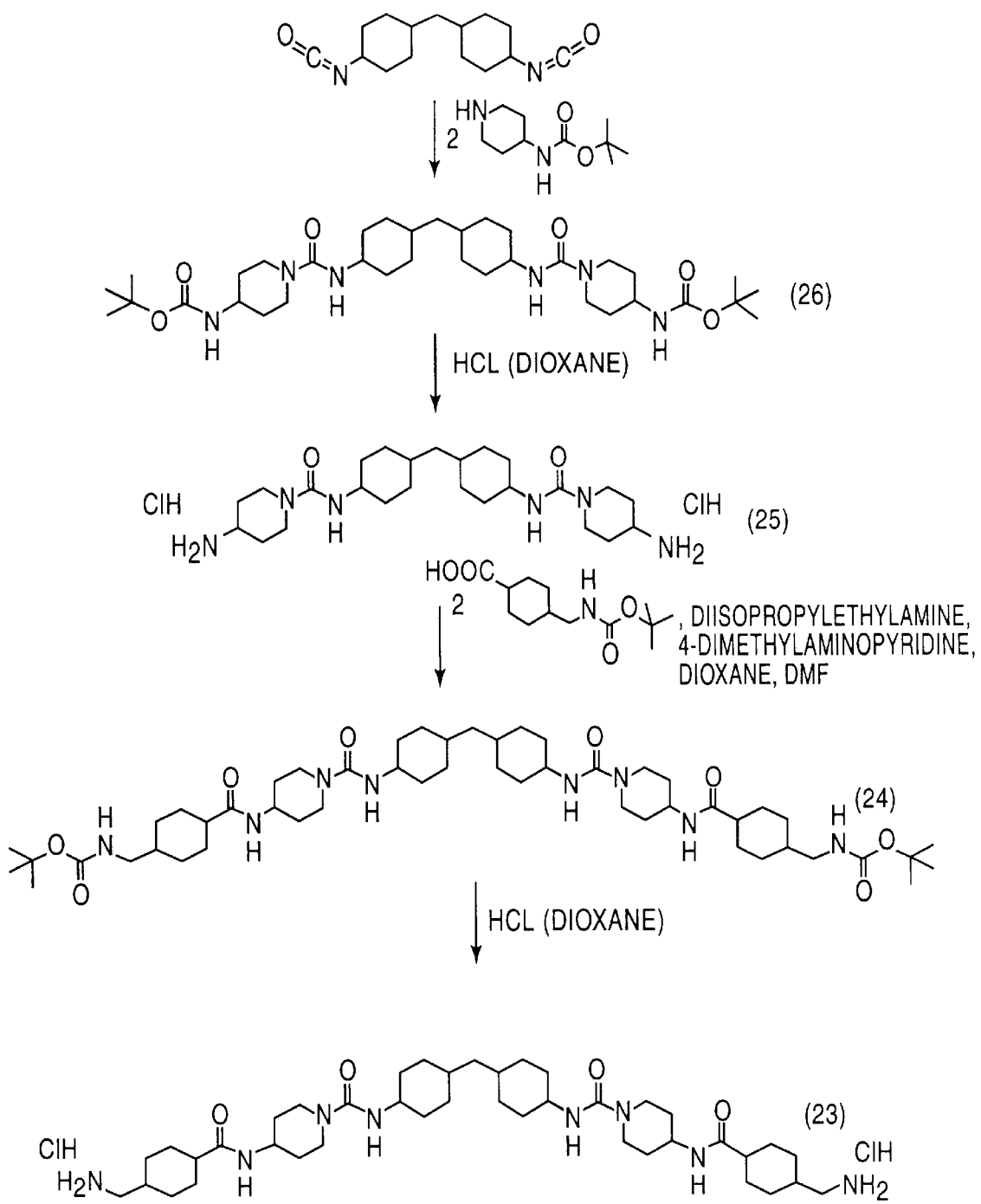

END PRODUCT di{4-[4-(4-Aminomethyl)cyclohexanoylamino]piperidin-1-ylcarbamoyl}cyclohexylmethane Dihydrochloride (23) (cf. FIG. 15)

Di{4-[4-(4-tert-butoxycarbonylaminomethyl)cyclo-hexanoylamino]piperidin-1-ylcarbamoyl}cyclohexylmethane (0.65 g; 0.7 mmol) is stirred, at 40–45°c for 24 hours, in 4.8 M HCl in dioxane (7 ml). After the addition of diethyl ether (50 ml), the mixture is cooled in an ice bath. The product, which has precipitated out, is filtered off with suction, washed several times with diethyl ether and dried in vacuo. Yield: 0.26 g, white amorphous solid.

MS (ESI): 741.5 (100) MH$^+$

STARTING COMPOUNDS di{4-[4-(4-tert-Butoxycarbonylaminomethyl)cyclo-exanoylamino]piperidin-1-ylcarbamoyl)cyclohexylmethane (24)

Di[4-(4-aminopiperidin-1-ylcarbamoyl)]cyclohexylmethane dihydrochloride (0.54 g; 1.0 mmol), Boc-tranexamic acid (0.57 g; 2.2 mmol), N-ethyldiisopropylamine (0.38 ml; 2.2 mmol) and 4-dimethylaminopyridine (30 mg) are stirred, at room temperature for 15 minutes, in dimethyl formamide (5 ml) and dioxane (5 ml). After the addition of N-(3-dimethylaminopropyl)-N'-ethylcarbodiimide hydrochloride (0.43 g; 2.2 mmol), the reaction mixture is stirred at 40° C. for 48 hours. The solvent is completely stripped off in vacuo. The residue is chromatographed on silica gel (dichloromethane:methanol; 9:1). The product fraction is collected and the solvent is stripped off completely in vacuo. Yield: 0.65 g, viscous oil, which was subjected to further reaction without any characterization.

di[4-(4-Aminopiperidin-1-ylcarbamoyl)]cyclohexylmethane Dihydrochloride (25)

Di(4-[4-(tert-butoxycarbamoyl)piperidin-1-yl-carbamoyl]}cyclohexylmethane (4.90 g; 7.0 mmol) is suspended in 4.8 M HCl in dioxane (50 ml). The suspension is stirred at 40–4–5° C. for 48 hours. After the addition of diethyl ether (100 ml), the mixture is cooled in an ice bath. The product, which has precipitated out, is filtered off with suction, washed several times with diethyl ether and dried in vacuo. Yield: 4.10 g, white amorphous solid.

MS(EI): 463.4 (100) MH$^+$ di{4-[4-(tert-Butoxycarbamoyl)piperidin-1-yl-carbamoyl]}cyclohexylmethane (26)

A solution of dicyclohexylmethane-4,4'-diisocyanate (1.90 g; 7.3 mmol) in dichloromethane (10 ml) is added dropwise, at room temperature, to the stirred solution of 4-tert-butoxycarbamoylpiperidine (3.20 g; 16.0 mmol) in dichloromethane (30 ml). After the addition has come to an end, the mixture is stirred at room temperature for a further three hours. The product, which has precipitated out, is filtered off with suction, washed several times with hexane and dried in vacuo. Yield: 4.10 g, white amorphous solid.

MS(ESI): 685.3 (57) MNa$^+$; 663.2 (100) MH$^+$

Example 11

Figure 16:
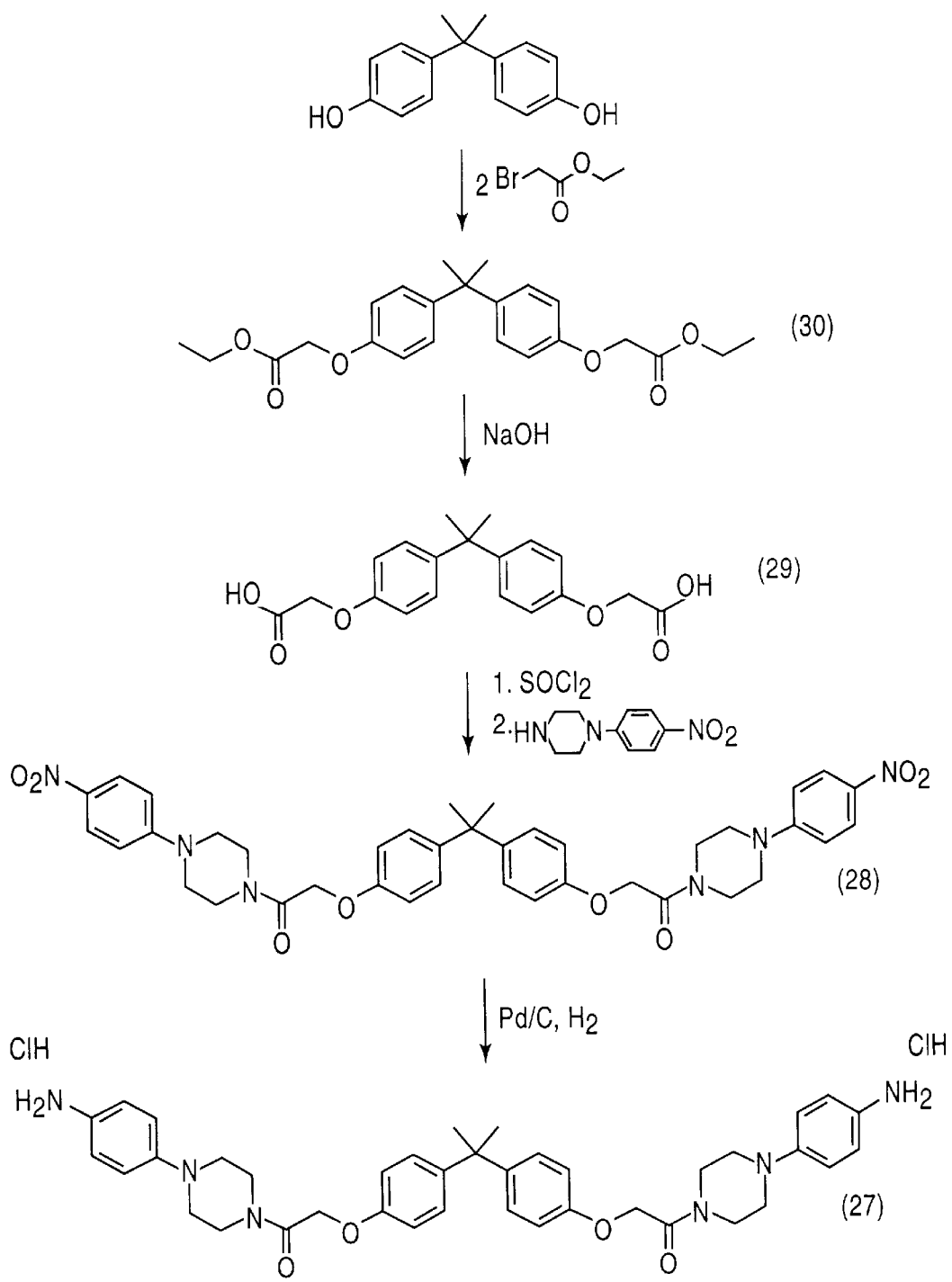

END PRODUCT 2,2-bis{4-[4-(4-Aminophenyl)-1-piperazinylcarbonyl-methoxy]phenyl}propane Dihydrochloride (27) (cf. FIG. 16)

0.65 g of 2,2-bis{4-[4-(4-nitrophenyl)-1-piperazinyl-carbonylmethoxy]phenyl}propane is dissolved in 60 ml of glacial acetic acid, and 0.2 g of palladium charcoal (10%) is added. The mixture is hydrogenated in a bypass apparatus until the starting product can no longer be detected (TLC). The catalyst is filtered off with suction through celite and the filtrate is evaporated down to dryness in vacuo on a rotary evaporator. The residue is dissolved in dichloromethane and the solution is washed with NaHCO$_3$ solution, dried over Na$_2$SO$_4$, filtered and concentrated once again. The residue is chromatographed through a silica gel column using a mixture consisting of ethyl acetate/methanol/NH$_4$OH (25%), in the ratio 90:8:2, as the mobile phase. The chromatographically pure fractions are combined and concentrated, and the residue is dissolved in dichloromethane. Following the addition of ethereal hydrochloric acid, the solution is concentrated and the residue is subsequently distilled twice with dichloromethane and then triturated with ethyl acetate/isopropanol. The precipitate is filtered off with suction, washed and then dried under high vacuum. 0.32 g of the title compound, having a m.p., with decomposition, from 182° C., is obtained.

STARTING COMPOUNDS 2,2-bis(4-[4-(4-Nitrophenyl)-1-piperazinylcarbonyl-methoxy]phenyl)propane (28)

2.5 g of 4-[4-carboxymethoxyphenyl)-1-methylethyl]-phenoxyacetic acid are suspended in toluene, and 1.6 ml of thionyl chloride are added. The mixture is heated under reflux for 5 hours and, after cooling, is concentrated on a rotary evaporator. The residue is subsequently distilled twice with toluene and the resulting crude diacid chloride is then dissolved in 50 ml of abs. dioxane. 2.95 g of 1-(4-nitrophenyl)piperazine, 2 ml of triethylamine and a spatula tip of 4-dimethylaminopyridine are added one after the other. The mixture is stirred at 50° C. for 2.5 h. Following cooling, water is added to the mixture and the pH is adjusted to 9 with dilute sodium hydroxide solution. The product, which has separated out, is caused to crystallize by grinding, and the crystals are then filtered off with suction, washed with water and dried over calcium chloride. 4.7 g of the title compound, having a m.p., with decomposition, from 165° C., are obtained.

4-[1-(4-Carboxymethoxyphenyl)-1-methylethyl]phenoxy-acetic Acid (29)

6.7 g of ethyl 4-[1-(4-ethoxycarbonylmethoxyphenyl)-1-methylethyl]phenoxyacetate are dissolved in 20 ml of methanol, and 16.7 g of 10% strength sodium hydroxide solution are added. The mixture is heated to boiling under reflux for 3 hours, after which it is cooled down and the methanol is then distilled off on a rotary evaporator. The residue is diluted with water and acidified to pH 2 with 2 N HCl; the colorless precipitate is then filtered off with suction, washed with water and dried in vacuo over calcium chloride. 5.5 g of the title compound, having a m.p. of 177–179° C., are obtained.

Ethyl 4-[1-(4-Ethoxycarbonylmethoxyphenyl)-1-methyl-ethyl]phenoxyacetate (30)

A mixture of 10 g of 4,4'-isopropylidenediphenol, 10.7 ml of ethyl bromoacetate, 15.2 g of potassium carbonate and 1 spatula tip of 18-crown-6 in 180 ml of acetone is heated to boiling under reflux for 4 hours. The solid is then removed by filtering off with suction and the filtrate is concentrated in vacuo and 100 ml of diisopropyl ether are added to the residue. The precipitate is filtered off with suction, washed with a little diisopropyl ether and dried. 15.5 g of the title compound, having a m.p. of 69–71° C., are obtained.

Example 12

Figure 17:
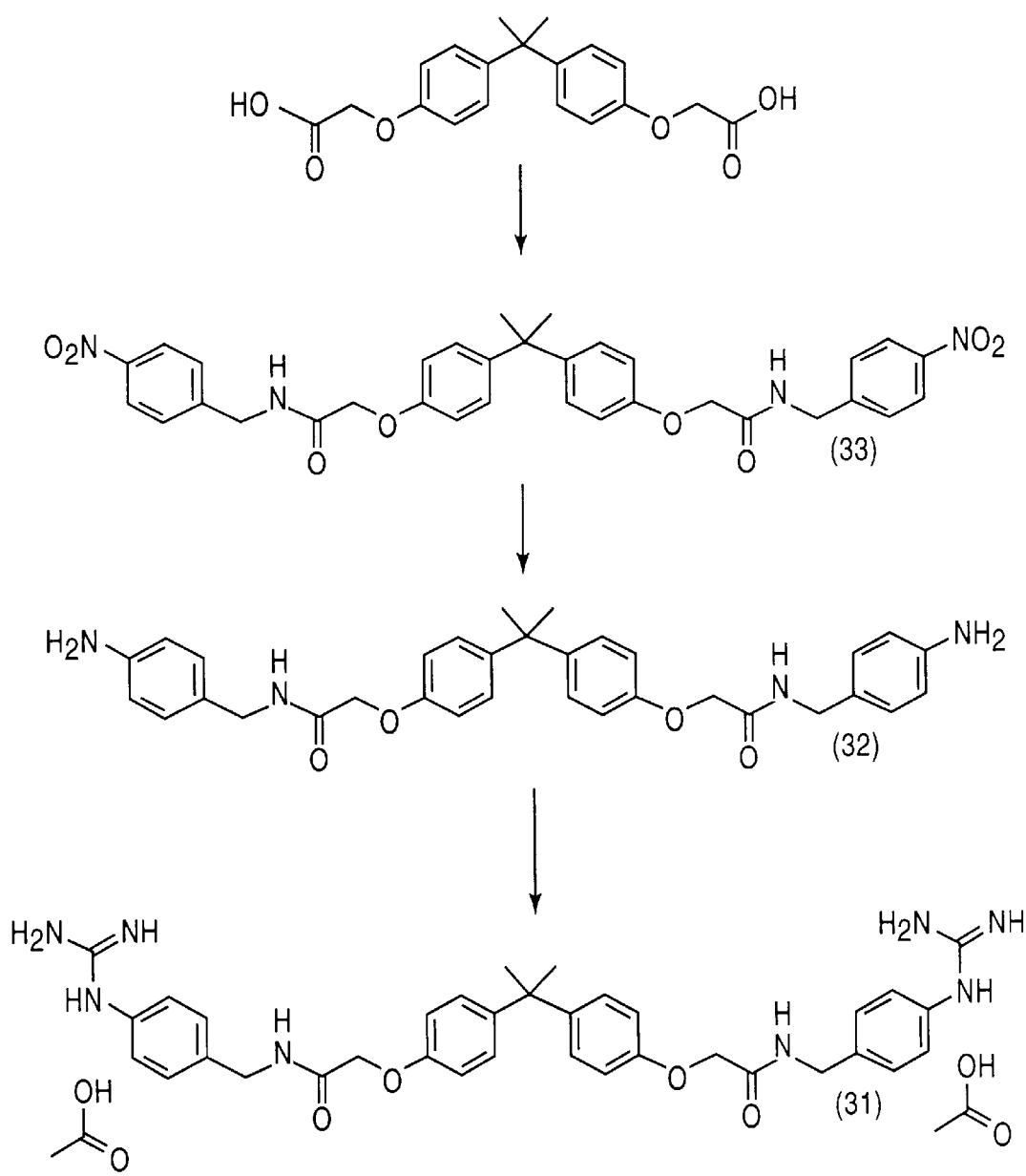

END PRODUCT 2,2-bis-[4-(4-Guanidinylbenzylamino)carbonylmethoxy-phenyl]propane Dihydroacetate (31) (cf. FIG. 17)

0.88 g of 1,3-bis(benzyloxycarbonyl)-2-methyliso-thiourea, 0.68 g of mercury(II) chloride and 0.69 g of triethylamine are added, one after the other, while stirring, to 0.63 g of 2,2-bis-[4-(4-aminobenzylamino)-carbonylmethoxyphenyl]propane in 10 ml of abs. DMF. The mixture is stirred at room temperature for 3 h and is then diluted with ethyl acetate; the precipitate which results is removed by filtering off with suction and the filtrate is washed once with a 5% strength soda solution and twice with water. The solution is dried over magnesium sulfate and filtered with suction, and the filtrate is evaporated to dryness in vacuo. The oil is chromatographed through a silica gel column using a mixture consisting of dichloromethane/ethanol, 95:5. The chromatographically pure fractions are combined and concentrated, and the residue (0.9 g) is dissolved in a mixture consisting of 60 ml of tetrahydrofuran, 3 ml of methanol and 1 ml of glacial acetic acid. After 0.3 g of palladium charcoal (10%) has been added, the mixture is hydrogenated in a bypass apparatus until the starting compound can no longer be detected. The catalyst is removed by filtering off with suction and the filtrate is evaporated to dryness. The viscous oil which remains is stirred up with THF and the resulting precipitate is filtered off with suction, washed with THF and diethyl ether and dried in vacuo at 80° C. 0.35 g of the title compound, having a m.p. of 1350 (decomposition), is obtained.

STARTING COMPOUNDS 2,2-bis-[4-(4-Aminobenzylamino) carbonylmethoxyphenyl]-propane (32)

1.8 g of 2,2-bis-[4-(4-nitrobenzylamino)carbonyl-methoxyphenyl]propane are dissolved in 300 ml of THF and, after addition of 0.5 g of palladium charcoal (10%), are hydrogenated in a bypass apparatus until the starting compound can no longer be detected (TLC). After the catalyst has been filtered off with suction, the filtrate is concentrated to dryness in vacuo and the residue is chromatographed through a silica gel column using a mixture of dichloromethane/ethanol, 95:5. The chromatographically pure fractions are combined and concentrated, and the residue is dried under high vacuum. 1.05 g of the title compound are obtained in the form of a solidified foam.

2,2-bis-[4-(4-Nitrobenzylamino)carbonylmethoxyphenyl]-propane (33)

1.5 ml of thionyl chloride are added to 2 g of 4-[1-(4-carboxymethoxyphenyl)-1-methylethyl]phenoxyacetic acid in 100 ml of toluene, and the mixture is heated to boiling under reflux for 5 h. After cooling, it is concentrated on a rotary evaporator and the residue is subsequently distilled twice with toluene. The resulting diacid chloride is dissolved in 40 ml of abs. dioxane, after which 2.2 g of 4-nitrobenzylamine hydrochloride are added; 3.5 ml of triethylamine are then added dropwise. The mixture is stirred at 50° C. for 2 h and then concentrated in vacuo. The precipitate which is obtained after adding water is filtered off with suction and dried in vacuo and, for further purification, chromatographed through a silica gel column using ethy-lacetate. The chromatographically pure fractions are combined, concentrated and dried. 1.25 g of the title compound are obtained as a solidified foam.

Example 13

Figure 18:
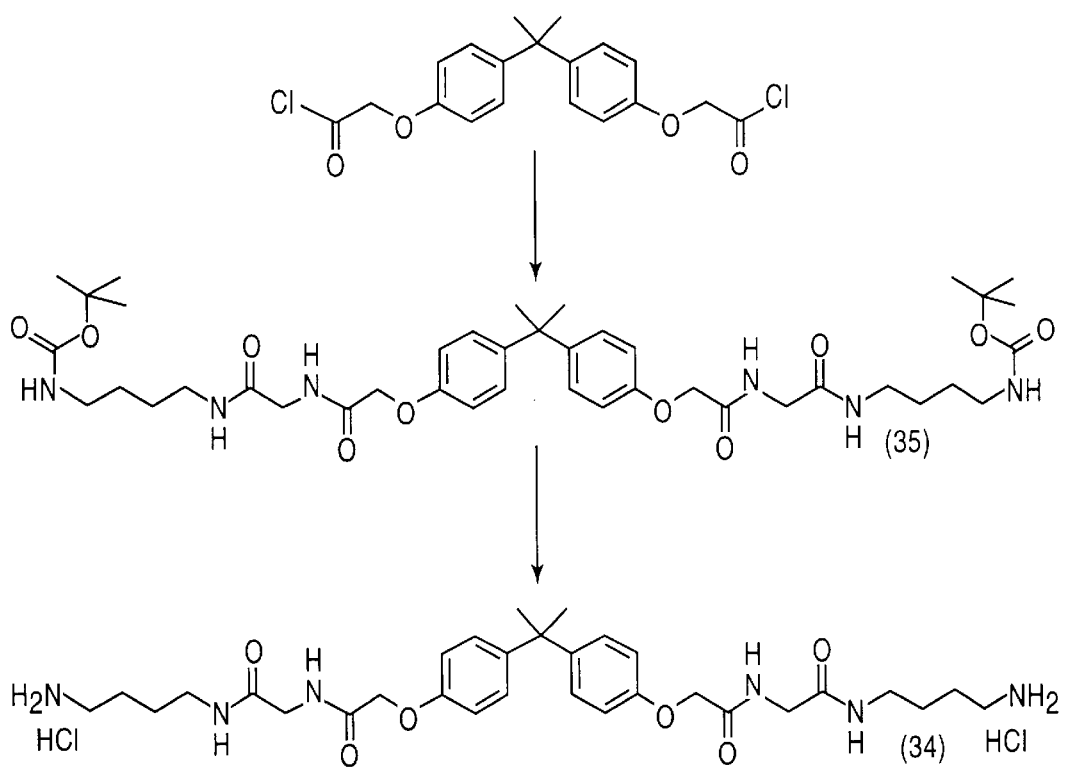

END PRODUCT 2,2-bis-[4-(10-Amino-3,6-diaza-2,5-dioxodecyloxy)-phenyl]propane Dihydrochloride (34) (cf. FIG. 18)

0.77 g of 2,2-bis-{4-[10-(tert-butoxycarbonylamino)-3,6-diaza-2,5-dioxodecyloxy]phenyl}propane is dissolved in 10 ml of abs. dioxane, and 2 ml of an approx. 4.8 M solution of hydrogen chloride in dioxane are added to this solution. The mixture is stirred overnight and the resulting precipitate is then filtered off with suction, washed with dioxane and then with diethyl ether and dried in vacuo at 80° C. 0.58 g of the title compound, having a m.p. of 173° C. (decomposition), is obtained.

STARTING COMPOUNDS 2-bis-[4-(10-(tert-Butoxycarbonylamino)-3,6-diaza-2,5-dioxodecyloxy]phenyl}propane (35)

0.67 g of 2,2-bis-(4-chlorocarbonylmethoxyphenyl)-propane (prepared in analogy with Example 33) in 5 ml of abs. dioxane is added dropwise, while stirring, to a solution of 0.85 g of N-[4-(tert-butoxycarbonylamino)butyl] glycineamide and 0.42 g of triethylamine in 10 ml of abs. dioxane. The mixture is stirred overnight and concentrated in vacuo, and the residue is partitioned between water and ethyl acetate. The organic phase is washed twice with water, dried over magnesium sulfate and concentrated. The residue is chromatographed through a silica gel column using a mixture of dichloromethane/ethanol, 95:5. The chromatographically pure fractions are combined and concentrated, and the residue is crystallized using diethyl ether/2-propanol. It is filtered off with suction, washed with diethyl ether and dried in vacuo. 0.77 g of the title compound, having a m.p. of 59° C. (decomposition), is obtained.

Example 14

Figure 19:
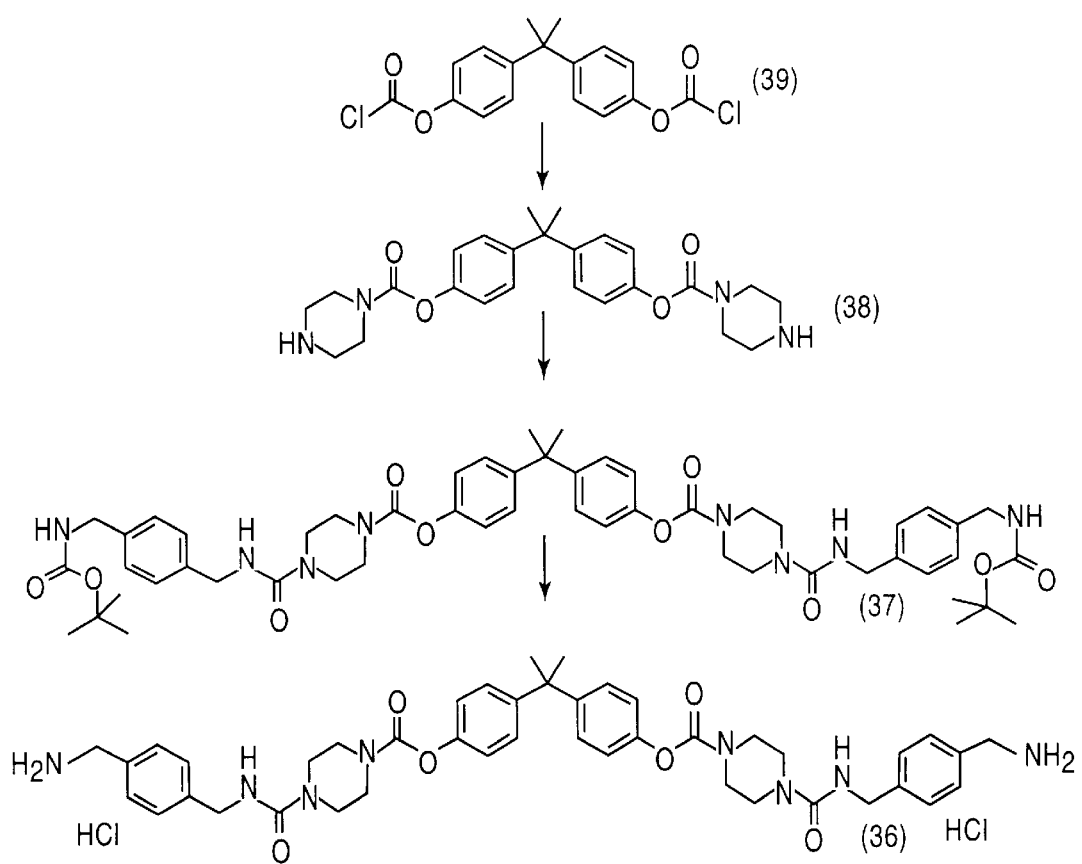

END PRODUCT 2,2-bis-(4-[4-(4-Aminomethylbenzylcarbamoyl)-1-piperazinylcarbonyloxy]phenyl)propane Dihydrochloride (36) (cf. FIG. 19)

0.14 g of 2,2-bis-{4-[4-(4-tert-butoxycarbonylamino-methylbenzylcarbamoyl)-1-piperazinylcarbonyloxy]-phenyl}propane is dissolved in 2 ml of abs. dioxane, and 2 ml of an approx. 20% solution of hydrogen chloride in dioxane is added to this solution. The mixture is stirred overnight and the precipitate is filtered off with suction, washed twice with diethyl ether and dried in vacuo. 0.08 g of the title compound, having a m.p. of from 250° C. (decomposition), is obtained.

STARTING COMPOUNDS 2,2-bis-(4-[4-(4-tert-Butoxycarbonylaminomethylbenzyl-carbamoyl)-1-piperazinylcarbonyloxy]phenyl)propane (37)

0.2 g of 2,2-bis[4-(1-piperazinylcarbonyloxy)phenyl]-propane dihydrochloride and 0.66 ml of diisopropyl-ethylamine are dissolved in 5 ml of dichloromethane, and 0.4 ml of a 20% strength solution of phosgene in toluene is then added to this solution. After the mixture has been stirred at room temperature for 30 min, 0.18 g of 4-(tert-butoxycarbonylaminomethyl)-benzylamine is added and the mixture is stirred for a further 30 min. Water is then added and the phases are separated; the organic phase is then washed a further two times with water. After the organic phase has been dried over magnesium sulfate, it is concentrated on a rotary evaporator. The residue is chromatographed through a silica gel column using dichloro-methane/methanol, 95:5, as the mobile phase. The chromatographically pure fractions are combined and evaporated to dryness in vacuo. 0.17 g of the title compound is obtained as a solidified foam.

2,2-bis[4-(1-Piperazinylcarbonyloxy)phenyl]propane Dihydrochloride (38)

8.3 g of 2,2-bis[4-(4-tert-butoxycarbonyl-1-piperazinylcarbonyloxy)phenyl]propane dihydrochloride are dissolved in 50 ml of abs. dioxane, and 9.5 ml of an approx. 20% solution of hydrogen chloride in dioxane are added to this solution while stirring. The mixture is stirred overnight, after which it is diluted with toluene and the precipitate is filtered off with suction. After drying in vacuo, 5.7 g of the title compound, having a m.p. of from 200° C. (decomposition), are obtained.

2,2-bis[4-(4-tert-Butoxycarbonyl-1-piperazinyl-carbonyloxy)phenyl]propane (39)

5 g of bisphenol A bis(chloroformate) are dissolved in 50 ml of dichloromethane, and 7.3 ml of diisopropyl-ethylamine and 6.6 g of 1-tert-butoxycarbonylpiperazine are added while cooling with ice. The mixture is stirred at room temperature for 1 h and then extracted three times with an ice-cold 0.5 N solution of hydrochloric acid and twice with 1 N sodium hydroxide solution. After having been dried with magnesium sulfate, it is then evaporated on a rotary evaporator and the solid is dried in vacuo. 8.4 g of the title compound, having a m.p. of 171–172° C., are obtained.

Example 15

Biological Investigations

The documented pathophysiological effects of mast cell tryptase are brought about directly by the enzymic activity of the protease. Accordingly, they are reduced or blocked by inhibitors which inhibit the enzymatic activity of the tryptase. The equilibrium dissociation constant $K_i$ of the enzyme-inhibitor complex is a suitable measure of the affinity of a reversible inhibitor for the target protease. This $K_i$ value can be determined by measuring the effect of the inhibitor on the tryptase-induced cleavage of a chromogenic peptide-p-nitroanilide substrate.

Methodology

The dissociation constants of the tryptase-inhibitor complexes are determined under equilibrium conditions in accordance with the general recommendations of Bieth (Bieth JG, Pathophysiological interpretation of kinetic constants of protease inhibitors, Bull. Europ. Physiopath. Resp. 16:183–195, 1980) and the methods of Sommerhoff et al. (Sommerhoff CP et al., A. Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is prepared in a pure state from lung tissue; the specific activity of the isolated protease, determined by means of titration, is normally 85% of the theoretical value. Constant quantities of tryptase are incubated with increasing quantities of the inhibitors in the presence of 50 μg of heparin/ml for stabilizing the protease. After the equilibrium has been established between the reaction partners, the remaining enzyme activity is determined after adding the peptide-p-nitroanilide substrate tos-Gly-Pro-Arg-pNA, the cleavage of which is monitored at 405 nm over a period of 3 min. Alternatively, the residual enzymic activity can also be determined using fluorogenic substrates. The apparent dissociation constants $K_{iapp}$ (i.e. in the presence of substrate) are subsequently ascertained by nonlinear regression by fitting the enzyme rates to the general equation for reversible inhibitors (Morrison JF, Kinetics of the reversible inhibition of enzyme-catalysed reactions by tight-binding inhibitors, Biochim. Biophys. Acta 185, 269–286, 1969):

$$V_1/V_0 = 131 \{E_t + I_t + K_{iapp} - [(E_t + I_t + K_{iapp})^2 - 4E_tI_t]^{1/2}\}/2E_t$$

In this equation, $V_1$ and $V_0$ are the rates in the presence and absence of the inhibitor, respectively, and $E_t$ and $l_t$ are the concentrations of the tryptase and of the inhibitor.

The apparent dissociation constants which were determined for the compounds according to the invention are given in Table A below, in which the numbers of the compounds correspond to the numbers of the compounds in the examples.

TABLE A

| Inhibition of human tryptase | |
|---|---|
| Compound | $K_{iapp}$ (μM) |
| 1 | 3 |
| 11 | 0.03 |
| 15 | 3 |
| 17 | 22 |
| 21 | 0.1 |
| 23 | 0.8 |
| 31 | 0.2 |
| 34 | 2 |
| 36 | 0.028 |

What is claimed is:

1. A method for determining tryptase in a biological sample, comprising obtaining a biological sample suspected of containing tryptase, incubating said biological sample with a tryptase inhibitor, and determining any complex formed between said tryptase inhibitor and any tryptase in said biological sample, wherein said tryptase inhibitor is a compound of formula I

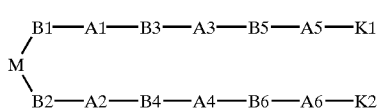

wherein
A1 and A2 are each independently selected from the group consisting of —O— and —NH—C(O)—,
A3 and A4 are each independently selected from the group consisting of —C(O)—NH— and

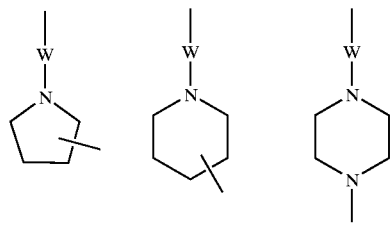

where W is the group —C(O)— or a bond,
A5 and A6 are each independently selected from the group consisting of —C(O)—, —C(O)—NH—, —NH—C(O)— and a bond,
M is selected from one of the following groups:

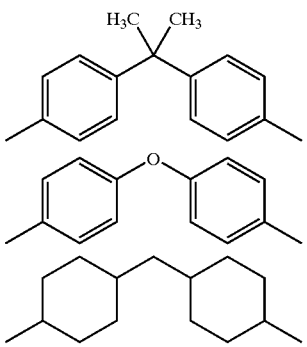

K1 is -B7-(C(O))$_m$-B9-X1 or -B7-(C(O))$_m$-B9-Z1-B11-X1,
K2 is -B8-(C(O))$_p$-B10-X2 or -B8-(C(O))$_p$-B10-Z2-B12-X2,
B1, B2, B3, B4, B5 and B6 are each independently selected from the group consisting of a bond and —CH$_2$—,
B7, B8, B9, B10, B11 and B12 are each independently selected from the group consisting of a bond and 1–2C-alkylene,
m is 0 or 1,
p is 0 or 1,
X1 and X2 are each independently selected from the group consisting of amino, amidino and guanidino, and
Z1 and Z2 are each independently selected from the group consisting of 1,4-phenylene, 1,3-phenylene, 1,4-cyclohexylene or 1,4-piperazinylene, wherein 24 to 40 bonds are present on a direct route between terminal nitrogen atoms, and
a pharmaceutically acceptable salt of said compound wherein compounds in which at least one to twelve of the variables B1, B2, B3, B4, B5, B6, B7, B8, B9, B10, B11 or B12 is a bond resulting in the direct linkage of two heteroatoms or two carbonyl groups are excluded.

2. The method according to claim 1, wherein said biological sample is obtained from a patient suspected of having an allergic or inflammatory disease.

3. The method according to claim 1, wherein said tryptase inhibitor is selected from the group consisting of:
bis{4-[4-(4-aminomethylcyclohexanoyl)piperazin-1-yl]carbonyl}4,4'-diaminodiphenyl ether,
bis{4-[4-(3-aminomethyl)benzoylpiperazin-1-yl]carbonyl}4,4'-diaminodiphenyl ether,
di{4-[4-(4-aminomethyl)cyclohexanoylamino]piperidin-1-ylcarbamoyl}cyclohexylmethane,
2,2-bis[4-(4-guanidinylbenzylamino)carbonylmethoxyphenyl]propane,
2,2-bis[4-(10-amino-3,6-diaza-2,5-dioxodecyloxyphenyl]propane, and
2,2-bis{4-[4-(4-aminomethylbenzylcarbamoyl)-1-piperazinylcarbonyloxy]phenyl}propane, and
a salt thereof.

4. A method for identifying potential tryptase inhibitors, comprising:
obtaining and inhibiting purified tryptase,
crystallizing the resulting inhibited, purified tryptase,
analyzing the structure of the inhibited, purified-tryptase using X-ray structural analysis, and
identifying a tryptase inhibitor with functional groups which bind to active sites on tryptase identified using said X-ray structural analysis.

* * * * *

SEQUENCE LISTING

<160> NUMBER OF SEQ ID NOS: 7

<210> SEQ ID NO 1
<211> LENGTH: 245
<212> TYPE: PRT
<213> ORGANISM: Homo sapiens

<400> SEQUENCE: 1

```
Ile Val Gly Gly Gln Glu Ala Pro Arg Ser Lys Trp Pro Trp Gln Val
 1               5                  10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
 65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys Pro
                245
```

<210> SEQ ID NO 2
<211> LENGTH: 223
<212> TYPE: PRT
<213> ORGANISM: Bos taurus

<400> SEQUENCE: 2

```
Ile Val Gly Gly Tyr Thr Cys Gly Ala Asn Thr Val Pro Tyr Gln Val
 1               5                  10                  15

Ser Leu Asn Ser Gly Tyr His Phe Cys Gly Gly Ser Leu Ile Asn Ser
                20                  25                  30

Gln Trp Val Val Ser Ala Ala His Cys Tyr Lys Ser Gly Ile Gln Val
            35                  40                  45

Arg Leu Gly Glu Asp Asn Ile Asn Val Val Glu Gly Asn Glu Gln Phe
        50                  55                  60
```

```
Ile Ser Ala Ser Lys Ser Ile Val His Pro Ser Tyr Asn Ser Asn Thr
 65                  70                  75                  80

Leu Asn Asn Asp Ile Met Leu Ile Lys Leu Lys Ser Ala Ala Ser Leu
                 85                  90                  95

Asn Ser Arg Val Ala Ser Ile Ser Leu Pro Thr Ser Cys Ala Ser Ala
            100                 105                 110

Gly Thr Gln Cys Leu Ile Ser Gly Trp Gly Asn Thr Lys Ser Ser Gly
        115                 120                 125

Thr Ser Tyr Pro Asp Val Leu Lys Cys Leu Lys Ala Pro Ile Leu Ser
130                 135                 140

Asp Ser Cys Lys Ser Ala Tyr Pro Gly Gln Ile Thr Ser Asn Met
145                 150                 155                 160

Phe Cys Ala Gly Tyr Leu Glu Gly Gly Lys Asp Ser Cys Gln Gly Asp
                165                 170                 175

Ser Gly Gly Pro Val Val Cys Ser Gly Lys Leu Gln Gly Ile Val Ser
            180                 185                 190

Trp Gly Ser Gly Cys Ala Gln Lys Asn Lys Pro Gly Val Tyr Thr Lys
        195                 200                 205

Val Cys Asn Tyr Val Ser Trp Ile Lys Gln Thr Ile Ala Ser Asn
210                 215                 220

<210> SEQ ID NO 3
<211> LENGTH: 230
<212> TYPE: PRT
<213> ORGANISM: Bos taurus

<400> SEQUENCE: 3

Ile Val Asn Gly Glu Glu Ala Val Pro Gly Ser Trp Pro Trp Gln Val
  1               5                  10                  15

Ser Leu Gln Asp Lys Thr Gly Phe His Phe Cys Gly Gly Ser Leu Ile
             20                  25                  30

Asn Glu Asn Trp Val Val Thr Ala Ala His Cys Gly Val Thr Thr Ser
         35                  40                  45

Asp Val Val Ala Gly Glu Phe Asp Gln Gly Ser Ser Ser Glu Lys
 50                  55                  60

Ile Gln Lys Leu Lys Ile Ala Lys Val Phe Lys Asn Ser Lys Tyr Asn
 65                  70                  75                  80

Ser Leu Thr Ile Asn Asn Asp Ile Thr Leu Leu Lys Leu Ser Thr Ala
                 85                  90                  95

Ala Ser Phe Ser Gln Thr Val Ser Ala Val Cys Leu Pro Ser Ala Ser
            100                 105                 110

Asp Asp Phe Ala Ala Gly Thr Thr Cys Val Thr Thr Gly Trp Gly Leu
        115                 120                 125

Thr Arg Tyr Thr Asn Ala Asn Thr Pro Asp Arg Leu Gln Gln Ala Ser
130                 135                 140

Leu Pro Leu Leu Ser Asn Thr Asn Cys Lys Lys Tyr Trp Gly Thr Lys
145                 150                 155                 160

Ile Lys Asp Ala Met Ile Cys Ala Gly Ala Ser Gly Val Ser Ser Cys
                165                 170                 175

Met Gly Asp Ser Gly Gly Pro Leu Val Cys Lys Lys Asn Gly Ala Trp
            180                 185                 190

Thr Leu Val Gly Ile Val Ser Trp Gly Ser Ser Thr Cys Ser Thr Ser
        195                 200                 205
```

-continued

Thr Pro Gly Val Tyr Ala Arg Val Thr Ala Leu Val Asn Trp Val Gln
    210                 215                 220

Gln Thr Leu Ala Ala Asn
225                 230

<210> SEQ ID NO 4
<211> LENGTH: 244
<212> TYPE: PRT
<213> ORGANISM: Homo sapiens

<400> SEQUENCE: 4

Ile Val Gly Gly Gln Glu Ala Pro Arg Ser Lys Trp Pro Trp Gln Val
  1               5                  10                  15

Ser Leu Arg Val His Gly Pro Tyr Trp Met His Phe Cys Gly Gly Ser
               20                  25                  30

Leu Ile His Pro Gln Trp Val Leu Thr Ala Ala His Cys Val Gly Pro
           35                  40                  45

Asp Val Lys Asp Leu Ala Ala Leu Arg Val Gln Leu Arg Glu Gln His
       50                  55                  60

Leu Tyr Tyr Gln Asp Gln Leu Leu Pro Val Ser Arg Ile Ile Val His
 65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys

<210> SEQ ID NO 5
<211> LENGTH: 244
<212> TYPE: PRT
<213> ORGANISM: Homo sapiens

<400> SEQUENCE: 5

Ile Val Gly Gly Gln Glu Ala Pro Arg Ser Lys Trp Pro Trp Gln Val
  1               5                  10                  15

Ser Leu Arg Val His Gly Pro Tyr Trp Met His Phe Cys Gly Gly Ser
               20                  25                  30

Leu Ile His Pro Gln Trp Val Leu Thr Ala Ala His Cys Val Gly Pro
           35                  40                  45

-continued

```
Asp Val Lys Asp Leu Ala Ala Leu Arg Val Gln Leu Arg Glu Gln His
 50                  55                  60

Leu Tyr Tyr Gln Asp Gln Leu Leu Pro Val Ser Arg Ile Ile Val His
 65                  70                  75                  80

Pro Gln Phe Tyr Thr Ala Gln Ile Gly Ala Asp Ile Ala Leu Leu Glu
                 85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
            115                 120                 125

Gly Trp Gly Asp Val Asp Asn Asp Glu Arg Leu Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
            195                 200                 205

Ala Gly Val Val Ser Trp Gly Glu Gly Cys Ala Gln Pro Asn Arg Pro
210                 215                 220

Gly Ile Tyr Thr Arg Val Thr Tyr Tyr Leu Asp Trp Ile His His Tyr
225                 230                 235                 240

Val Pro Lys Lys
```

<210> SEQ ID NO 6
<211> LENGTH: 244
<212> TYPE: PRT
<213> ORGANISM: Homo sapiens

<400> SEQUENCE: 6

```
Ile Val Gly Gly Gln Glu Ala Pro Arg Ser Lys Trp Pro Trp Gln Val
 1               5                  10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
 50                  55                  60

Leu Tyr Tyr Gln Asp Gln Leu Leu Pro Val Ser Arg Ile Ile Val His
 65                  70                  75                  80

Pro Gln Phe Tyr Thr Ala Gln Ile Gly Ala Asp Ile Ala Leu Leu Glu
                 85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
            115                 120                 125

Gly Trp Gly Asp Val Asp Asn Asp Glu Arg Leu Pro Pro Phe Pro
130                 135                 140

Leu Lys Gln Val Lys Val Pro Ile Met Glu Asn His Ile Cys Asp Ala
145                 150                 155                 160
```

```
Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys

<210> SEQ ID NO 7
<211> LENGTH: 244
<212> TYPE: PRT
<213> ORGANISM: Homo sapiens

<400> SEQUENCE: 7

Ile Val Gly Gly Gln Glu Ala Pro Arg Ser Lys Trp Pro Trp Gln Val
 1               5                  10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys
```